United States Patent
Jayant et al.

(10) Patent No.: US 10,309,924 B2
(45) Date of Patent: Jun. 4, 2019

(54) FLOATING GATE BASED SENSOR APPARATUS AND RELATED FLOATING GATE BASED SENSOR APPLICATIONS

(71) Applicant: CORNELL UNIVERSITY, Ithaca, NY (US)

(72) Inventors: Krishna Jayant, Ithaca, NY (US); Edwin C. Kan, Ithaca, NY (US)

(73) Assignee: Cornell University, Ithaca, NY (US)

(*) Notice: Subject to any disclaimer, the term of this patent is extended or adjusted under 35 U.S.C. 154(b) by 549 days.

(21) Appl. No.: 14/896,010

(22) PCT Filed: Jun. 9, 2014

(86) PCT No.: PCT/US2014/041507
§ 371 (c)(1),
(2) Date: Dec. 4, 2015

(87) PCT Pub. No.: WO2014/197891
PCT Pub. Date: Dec. 11, 2014

(65) Prior Publication Data
US 2016/0131613 A1    May 12, 2016

Related U.S. Application Data

(60) Provisional application No. 61/896,748, filed on Oct. 29, 2013, provisional application No. 61/896,813, (Continued)

(51) Int. Cl.
*G01N 27/414* (2006.01)
*C12Q 1/6869* (2018.01)
(Continued)

(52) U.S. Cl.
CPC ....... *G01N 27/4145* (2013.01); *C12Q 1/6869* (2013.01); *C12Q 1/703* (2013.01);
(Continued)

(58) Field of Classification Search
CPC . C12Q 1/6869; C12Q 1/703; H01L 29/42328; G01N 27/4145
See application file for complete search history.

(56) References Cited

U.S. PATENT DOCUMENTS 6,953,958 B2    10/2005    Baxter et al.
7,053,439 B2    5/2006    Kan et al.
(Continued)

FOREIGN PATENT DOCUMENTS

WO    2008128745    10/2008
WO    2012036679    3/2012
(Continued)

OTHER PUBLICATIONS

Chen, Baozhen, Integrated Bioassays for Screening Chemical and Biological Species, Iowa State University, 2010, pp. 1-102.
(Continued)

*Primary Examiner* — Narayan K Bhat
(74) *Attorney, Agent, or Firm* — Perkins Coie LLP

(57) ABSTRACT

A floating gate based sensor apparatus includes at least two separate electrical bias components with respect to a floating gate based sensor surface within the floating gate based sensor apparatus. By including the at least two electrical bias components, the floating gate based sensor apparatus provides enhanced capabilities for biomaterial and non-biomaterial detection and manipulation while using the floating gate based sensor apparatus.

27 Claims, 35 Drawing Sheets
Specification includes a Sequence Listing.

Related U.S. Application Data filed on Oct. 29, 2013, provisional application No. 61/832,218, filed on Jun. 7, 2013.

(51) Int. Cl.
*C12Q 1/70* (2006.01)
*H01L 29/423* (2006.01)

(52) U.S. Cl.
CPC ... *G01N 27/4146* (2013.01); *H01L 29/42328* (2013.01); *H01L 29/42364* (2013.01); *C12Q 2600/158* (2013.01)

(56) References Cited

U.S. PATENT DOCUMENTS

| | | | |
|---|---|---|---|
| 7,125,478 B2 | 10/2006 | Selvaganapathy et al. | |
| 7,399,398 B2 | 7/2008 | Rakestraw et al. | |
| 7,462,512 B2 | 12/2008 | Levon et al. | |
| 7,470,962 B2 | 12/2008 | Baumann et al. | |
| 7,535,232 B2 * | 5/2009 | Barbaro | G01N 27/4145 324/109 |
| 7,649,358 B2 | 1/2010 | Toumazou et al. | |
| 7,931,791 B2 | 4/2011 | Tolley et al. | |
| 7,960,776 B2 | 6/2011 | Kim et al. | |
| 8,143,908 B2 | 3/2012 | Uenleubayir et al. | |
| 8,349,167 B2 | 1/2013 | Rothberg et al. | |
| 8,519,345 B2 | 8/2013 | Arsalan et al. | |
| 2004/0122475 A1 | 6/2004 | Myrick et al. | |
| 2004/0266076 A1 | 12/2004 | Doris et al. | |
| 2006/0038222 A1 | 2/2006 | Kan et al. | |
| 2008/0094074 A1 | 4/2008 | Kim et al. | |
| 2010/0096266 A1 | 4/2010 | Kim et al. | |
| 2010/0194408 A1 | 8/2010 | Sturmer et al. | |
| 2010/0194409 A1 | 8/2010 | Gao et al. | |
| 2011/0208457 A1 | 8/2011 | Merz et al. | |
| 2013/0264206 A1 | 10/2013 | Eom et al. | |
| 2013/0273664 A1 | 10/2013 | Toumazou et al. | |

FOREIGN PATENT DOCUMENTS

| | | |
|---|---|---|
| WO | 2013158021 | 10/2013 |
| WO | 2013165375 | 11/2013 |

OTHER PUBLICATIONS

Pandey, Santosh, et al., Novel Neuromorphic CMOS Device Array for Biochemical Charge Sensing, Department of Electrical and Compute Engineering, Iowa State University, 30th Annual International IEEE EMBS Conference Vancouver, British Columbia, Canada, Aug. 20-24, 2008, pp. 2291-2294.

Jacquot, Blake C., et al., Non-Faradaic electrochemical detection of protein interactions by integrated neuromorphic CMOS sensors, Biosensors and Bioelectronics 23 (2008) 1503-1511.

Shen, Nick Y., et al., Integration of chemical sensing and electrowetting actuation on chemoreceptive neuron MOS (CνMOS) transistors, Sensors and Actuators B 102 (2004) 35-43.

Tareq, MD. Obaej, Floating Gate Metal-Oxide-Semiconductor Based Gas Sensor, University of Manitoba, Winnipeg, 2014, pp. 1-110.

Boutet, Paul-Antoine and Manen, Samuel, Low power CMOS potentiostat for three electrodes amperometric chemical sensor, 2011 Faible Tension Faible Consommation (FTFC), pp. 15-18.

Li, Yang-Guo and Haider, Mohammad Rafiqul, A Low-power Neuromorphic CMOS Sensor Circuit for the Implanted Biomolecular Detections, Department of Electrical and Computer Engineering, The University of Alabama at Birmingham, 2013, pp. 1-4.

Liu, Yaling, et al., Manipulation of nanoparticles and biomolecules by electric field and surface tension, Comput. Methods Appl. Mech. Engrg. 197 (2008)2156-2172.

International Search Report Form PCT/ISA/220, International Application No. PCT/US14/41507, pp. 1-12, dated Dec. 9, 2014.

\* cited by examiner $$I = I_0 \frac{kV_{FG}}{U_T} (e^{\frac{-V_S}{U_T}} - e^{\frac{-V_D}{U_T}})$$ DRAIN CURRENT IN SUBTHRESHOLD

WHERE $U_T$ IS THE THERMAL VOLTAGE $$K = \frac{C_{OX}}{C_{OX} + C_{dep}}$$ CHANNEL COUPLING COEFFICIENT $$I = \frac{\mu C_{OX} W}{2L} (V_{FG} - V_{TFG})^2$$ DRAIN CURRENT IN SATURATION $$V_{FG} = \frac{Q}{C_T} + \frac{C_{gs}}{C_T} V_S + \frac{C_{gd}}{C_T} V_D + \frac{C_{CG}}{C_T} V_{CG} + \frac{C_{SG}}{C_T} V_{SG}$$ FLOATING GATE POTENTIAL $$C_T = (\frac{C_{OX} * C_{dep}}{C_{OX} + C_{dep}}) + C_b + C_{gs} + C_{gd} + C_{CG} + C_{SG}$$ TOTAL FLOATING GATE CAPACITANCE $$S = \frac{U_T * \ln(10)}{K} (\frac{C_T}{C_{SG}})$$ SUBTHRESHOLD SLOPE $$A_C = \frac{\frac{W_{SG} L_{SG} * \varepsilon_{ax}}{t_{ax}} // C_{dl}}{\frac{W_{CG} L_{CG} * \varepsilon_{ax}}{t_{ax}}}$$ CAPACITIVE AMPLIFICATION RATIO $$\Delta V_{TCG} = \frac{-Q}{C_T} - \frac{C_{gs}}{C_T} V_S - \frac{C_{gd}}{C_T} V_D - A_C V_{SG}$$ SHIFT IN THRESHOLD VOLTAGE SEEN FROM CONTROL GATE

FIG. 4

SEQUENCE LISTING

<160> NUMBER OF SEQ ID NOS: 15

<210> SEQ ID NO 1
<211> LENGTH: 20
<212> TYPE: DNA
<213> ORGANISM: Artificial Sequence
<220> FEATURE:

<223> OTHER INFORMATION: Description of Artificial Sequence: Synthetic
      probe

<400> SEQUENCE: 1
cataggcctt ggaacctatg                                                   20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
cataggttcc aaggcctatg                                                   20

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
gcatctgggc tataaaggg cgtcg                                              25

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
cgacgccctt ttatagccca gatgc                                             25

<210> SEQ ID NO 5
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 5
gcatctgggc tataaaggg cgtcggtatc caaggttccg gatacgag                     48

<210> SEQ ID NO 6
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ctcgtatccg gaaccttgga taccgacgcc cttttatagc ccagatgc                    48

<210> SEQ ID NO 7
<211> LENGTH: 49
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 7
ctcattgatg gtctcttttt ttttggatcc gcatgacatt cgccgtaag         49

<210> SEQ ID NO 8
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ctcattgatg gtctcttttt tttcttacgg cgaatgaccg aatcagcct         49

<210> SEQ ID NO 9
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ctcattgatg gtctcttttt tttaggctga ttcggttcat gcggatcca         49

<210> SEQ ID NO 10
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
tggatccgca tgacattcgc cgtaagtttt tcaatctatc ccattctgc         49

<210> SEQ ID NO 11
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
cttacggcga atgaccgaat cagcctttt tcaatctatc ccattctgc         49

<210> SEQ ID NO 12
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
aggctgattc ggttcatgcg gatccatttt tcaatctatc ccattctgc         49

<210> SEQ ID NO 13
<211> LENGTH: 50
<212> TYPE: DNA
<213> ORGANISM: Human immunodeficiency virus

<400> SEQUENCE: 13

```
tgttaaaaga gaccatcaat gaggaagctg cagaatggga tagattgcat            50

<210> SEQ ID NO 14
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 14
ttcctcattg atggtctctt ttaacatttt t                                31

<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 15
tttttatgca atctatccca ttctgcagc                                   29
```

FLOATING GATE BASED SENSOR APPARATUS AND RELATED FLOATING GATE BASED SENSOR APPLICATIONS

CROSS-REFERENCE TO RELATED APPLICATIONS

This application is related to, and derives priority from, U.S. Provisional Patent Applications: (1) Ser. No. 61/832,218, filed 7 Jun. 2013; (2) Ser. No. 61/896,748, filed 29 Oct. 2013; and (3) Ser. No. 61/896,813, filed 29 Oct. 2013. Each of the foregoing United States Provisional Patent Applications is titled Electrochemical Sensor Apparatus, Methods and Applications, and each of the foregoing United States Provisional Patent Applications is incorporated herein fully by reference.

STATEMENT REGARDING FEDERALLY SPONSORED RESEARCH OR DEVELOPMENT

This invention was made with government support under grant number DMR 0520404 awarded by the National Science Foundation. The government has certain rights in the invention.

SEQUENCE LISTING

The instant application contains a Sequence Listing which has been filed electronically in ASCII format and is hereby incorporated by reference in its entirety. Said ASCII copy, created on Nov. 19, 2018, is named 078554-8091_US00_SL.txt and is 3,836 bytes in size.

BACKGROUND

Field of the Invention

Embodiments relate generally to floating gate based sensor apparatus and related analytical methods and applications. More particularly embodiments relate to floating gate based sensor apparatus and related analytical methods and applications with enhanced capabilities.

Description of the Related Art

Advances in biophysical analytical biotechnology are often predicated upon an ability to detect, separate and/or manipulate individual biomaterial components such as but not limited to cells, cell components and bio-macromolecules, further such as but not limited to proteins and nucleic acids.

Given that advances in biophysical analytical biotechnology are likely to continue to evolve, desirable are enhanced abilities to detect, separate and/or manipulate individual biomaterial components such as but not limited to cells, cell components and bio-macromolecules, further such as but not limited to proteins and nucleic acids.

SUMMARY

Embodiments include a floating gate based sensor apparatus useful in detecting and manipulating individual biomaterials (and non-biomaterials), as well as several biomaterial (and non-biomaterial) detection and manipulation applications for using the floating gate based sensor apparatus for detecting and manipulating individual biomaterials (and non-biomaterials).

In a most general sense, a floating gate based sensor apparatus in accordance with the embodiments utilizes at least two separate electrical biasing sources with respect to a floating gate or alternative sensor gate electrically coupled to the floating gate upon which may be detected and/or manipulated a biomaterial in accordance with the embodiments. In that regard, embodiments in particular illustrate: (1) a floating gate bias (or an alternative electrically coupled sensing gate bias) of a floating gate (or alternative sensing gate) with respect to a semiconductor substrate through a control gate modulated tunneling dielectric to floating gate charge injection mechanism; in conjunction with (2) a reference electrode bias of a liquid sample with respect to the floating gate (or alternative electrically coupled sensing gate) within the floating gate based sensor apparatus.

Within the context of the embodiments as described further below a "floating gate based sensor surface" is intended as a floating gate surface, a dielectric material clad floating gate surface, a sensing gate surface or a dielectric material clad sensing gate surface. Thus, a floating gate based sensor surface may comprise a material selected from the group including but not limited to dielectric materials (i.e., such as but not limited to silicon oxide dielectric materials, silicon nitride dielectric materials and silicon oxynitride dielectric materials) and conductor materials (i.e., such as but not limited to metal conductor materials and polysilicon conductor materials).

The embodiments are not in particular limited to the foregoing floating gate based sensor apparatus configuration that includes a control gate electrical bias component and a reference electrode electrical bias component, but may rather include a minimum of two control gate bias components rather than a control gate bias component and a reference electrode bias component. As well a minimum of two reference electrodes biases may be used in place of the two control gate biases. With respect to the biasing by at least two electrical bias components within the floating gate based sensor apparatus in accordance with the embodiments, such electrical bias by each of the independent two electrical bias components may independently be an AC bias or a DC bias.

Within the embodiments, a floating gate based sensor apparatus may be viewed as a sensor apparatus whose operation is predicated upon operation of a dual gate (i.e., floating gate and control gate) non-volatile field effect transistor from which may under certain circumstances be comprised or fabricated the floating gate based sensor apparatus. In general, a dual gate non-volatile field effect transistor comprises in layered succession: (1) a semiconductor substrate including a source region and a drain region separated by a channel region; (2) a tunneling dielectric located at least in-part upon the channel region of the semiconductor substrate; (3) a floating gate located at least in-part upon the tunneling dielectric; (4) an intergate dielectric located at least in-part upon floating gate; and (5) a control gate located at least in-part upon the intergate dielectric. In operation of such a dual gate non-volatile field effect transistor structure an electrical bias imposed upon the control gate with respect to the source region, the drain region and the semiconductor substrate induces a charge within the floating gate with respect to the semiconductor substrate predicated upon tunneling of charge carriers from the semiconductor substrate into the floating gate through the tunneling dielectric. A floating gate based sensor structure used within a floating gate based sensor apparatus further refines the foregoing dual gate non-volatile field effect transistor structure in a fashion such that: (1) at least a portion of a control gate is separated from at least a portion of a floating gate; and (2) at least the portion of the floating gate separated from at least the portion of the control gate (or an aerially related electrically coupled component) is used as a sensor surface within a liquid sample chamber which includes a sample liquid that is desired to be analyzed using the floating gate based sensor apparatus in accordance with the embodiments.

Within the context of the embodiments, any of the foregoing semiconductor substrate, tunneling dielectric, control gate, intergate dielectric and control gate may be formed using methods and materials, and to dimensions, that are otherwise generally conventional and within the context of functional limitations required to provide functional and operative embodiments.

Within the embodiments as described further below, a floating gate based sensor apparatus uses at least two electrical bias components with respect to a floating gate, or a sensing gate which may additionally be coupled to the floating gate.

Within the embodiments it is useful to differentiate: (1) a floating gate based sensor apparatus as described above that uses an extended and remote portion of a floating gate (or a related at least partially aligned coupled component) as a sensor surface; with (2) an ion sensitive field effect transistor (ISFET). In that regard, rather than using a floating gate based component as a sensor surface, an ISFET uses a gate dielectric as a sensor surface. The foregoing distinction between an ISFET and a floating gate based sensor structure or floating gate based sensor apparatus is intended as a governing definition of the embodiments described herein even under circumstances where related field effect transistor structures are alternatively described.

As is understood by a person skilled in then art, by virtue of the at least two separate bias components within the floating gate based sensor apparatus in accordance with the embodiments a method in accordance with the embodiments in particular potentially provides for determination of multiple and potentially interrelated properties of a biomaterial (or a non-biomaterial) with respect to a sensor surface. Such multiple and potentially interrelated properties may include, but are not necessarily limited to: (1) an affinity of a biomaterial (or a non-biomaterial) for the floating gate based sensor surface; and (2) an orientation of the biomaterial (or the non-biomaterial) with respect to the floating gate based sensor surface.

A particular apparatus in accordance with the embodiments includes a floating gate based sensor apparatus comprising a floating gate based sensor surface located within a liquid sample chamber over a substrate and adapted for electrical bias with at least two separate electrical bias components within the floating gate based sensor apparatus.

A particular sensing method in accordance with the embodiments includes introducing a liquid sample containing at least one analyte into a liquid sample chamber within a sensor apparatus comprising a floating gate based sensor surface located within the liquid sample chamber in-turn located over a substrate, the floating gate based sensor surface having at least two separate electrical biases with at least two separate electrical bias components within the sensor apparatus. This particular method also includes measuring at least two parameters of the at least one analyte within the liquid sample as a function of the at least two electrical bias with the at least two separate electrical bias components.

A particular method in accordance with the embodiments includes a method for electrochemical gating. The method utilizes a sensor apparatus comprising a floating gate based sensor surface located within a liquid sample chamber over a substrate and electrically biased with at least two separate electrical bias components within the sensor apparatus, wherein the two separate electrical bias components comprise: (i) a control gate bias within the sensor apparatus that electrically biases the floating gate based sensor surface with respect to the substrate; and (ii) a reference electrode bias that electrically biases a sample within the liquid chamber with respect to the floating gate based sensor surface.

A particular method in accordance with the embodiments includes a method for detecting a nucleic acid molecule in a sample. The method comprising the steps of: (i) providing a sensor apparatus comprising a floating gate based sensor surface located within a liquid sample chamber over a substrate and electrically biased with at least two separate electrical bias components within the sensor apparatus, wherein the floating gate is at least partially coated with poly-l-lysine; (ii) exposing the sensor apparatus to the sample; and (iii) measuring a change in floating gate potential ($V_{FG}$), wherein a change in $V_{FG}$ indicates the presence of a nucleic acid in the sample.

A particular method in accordance with the embodiments includes a method for reversibly immobilizing a nucleic acid molecule. The method comprising the steps of: (i) providing a sensor apparatus comprising a floating gate based sensor surface located within a liquid sample chamber over a substrate and electrically biased with at least two separate electrical bias components within the sensor apparatus, wherein the floating gate is at least partially coated with poly-l-lysine; and (ii) exposing the nucleic acid molecule to the sensor apparatus. Within the embodiments as described further below, the method can further include the step of injecting a charge, where the charge injection results in desorption of the adsorbed nucleic acid molecule.

A particular method in accordance with the embodiments includes a method for detecting a target nucleic acid in a sample. The method includes the steps of: (i) providing a nucleic acid oligonucleotide, wherein at least a portion of the nucleic acid oligonucleotide is complementary to at least a portion of the target nucleic acid; (ii) incubating the nucleic acid oligonucleotide with the sample under conditions suitable for the nucleic acid oligonucleotide to anneal to target nucleic acid, resulting in a double-stranded nucleic acid molecule; and (iii) detecting, using a sensor apparatus, the presence of the double-stranded nucleic acid molecule, wherein the sensor apparatus comprises a floating gate based sensor surface located within a liquid sample chamber over a substrate and electrically biased with at least two separate electrical bias components within the sensor apparatus, wherein the floating gate is at least partially coated with poly-l-lysine.

Within the embodiments of the method as described herein, it is often useful to conjugate the nucleic acid oligonucleotide to a detection probe such as a gold nanoparticle.

A particular method in accordance with the embodiments includes a method for measuring a change in the surface area of a cell, the method includes the steps of: (i) providing a sensor apparatus comprising a floating gate based sensor surface located within a liquid sample chamber over a substrate and electrically biased with at least two separate electrical bias components within the sensor apparatus; (ii) providing a plurality of cells; and (iii) monitoring, using the sensor apparatus, a change in surface potential of the plurality of cells, wherein a change in surface potential indicates a change in the surface area of the plurality of cells.

According to an embodiment, the floating gate can at least partially be coated with poly-l-lysine.

Within the embodiments of the method as described herein, it is often useful to introduce an agent to the plurality of cells, where the agent can, for example, induce exocytosis of the plurality of cells.

BRIEF DESCRIPTION OF THE DRAWINGS

The objects, features and advantages of the embodiments are understood within the context of the Detailed Description of the Non-Limiting Embodiments, as set forth below. The Detailed Description of the Non-Limiting Embodiments is understood within the context of the accompanying drawings, that form a material part of this disclosure, wherein:

FIG. 4 shows a series of governing equations for determining an ion sensitive field effect transistor structure performance in accordance with the embodiments.

The size of the ion is 5 Å. As the valency increases, the counter ion decay is more abrupt but results in a saturation of charge density at the interface. (c) Potential distribution for varying valency. (d) Role of varying the hydrated ion size. As the ionic radius increases the maximum achievable charge density at the interface reduces due to the steric effect.

Figure 9:
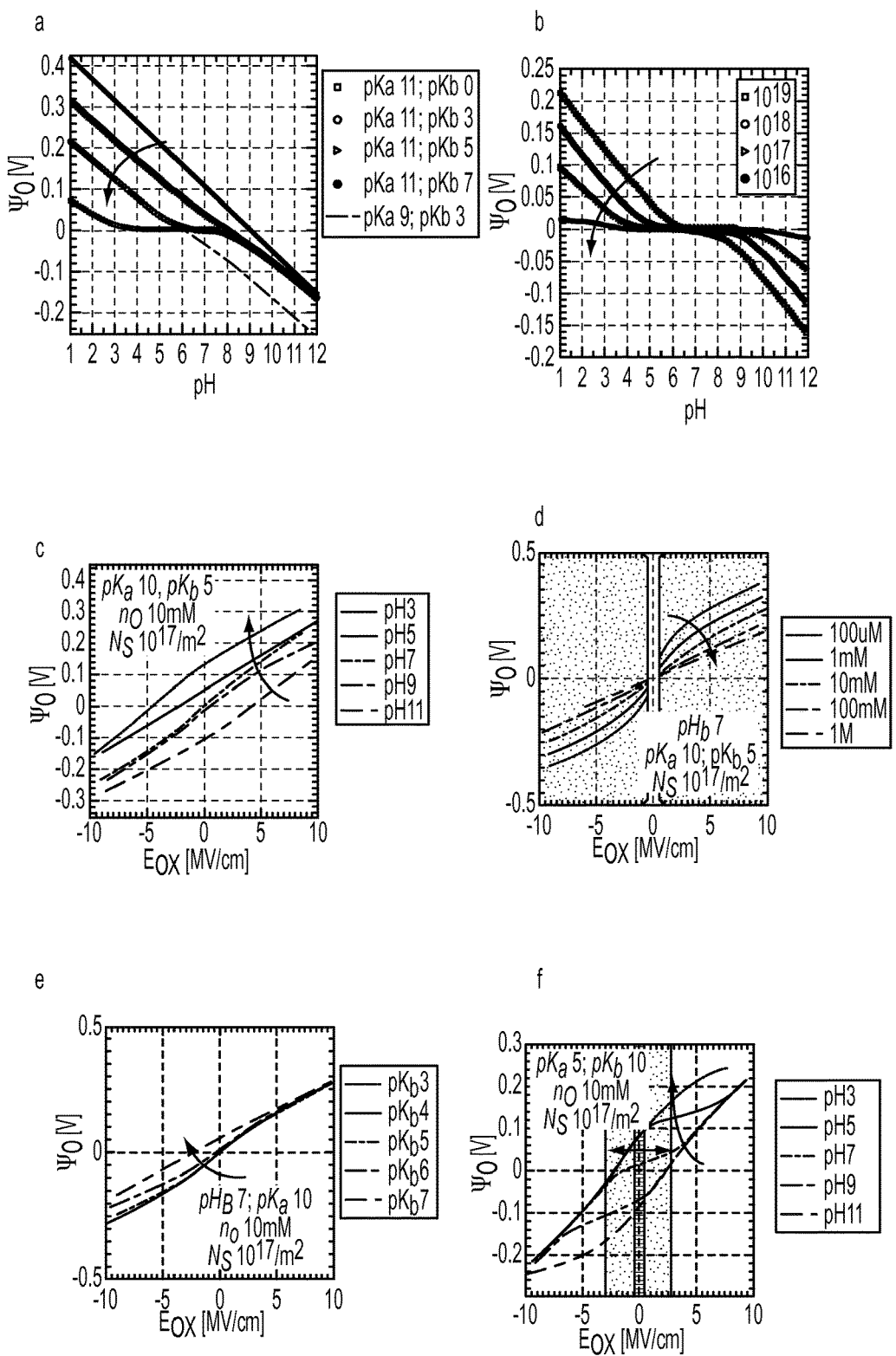

FIG. 9 shows (a) variation in $\psi_O$ as a function of $pH_B$ for variations in ΔpK. As ΔpK increases (arrow) the slope becomes more non-Nernstian (lower than 60 mV/pH). (b) $\psi_O$ vs. $pH_B$ for variations in surface site density in $m^{-2}$. The relative flattening in the response increases as $N_S$ decreases (arrow). (c) $\psi_O$ vs. $E_{OX}$ for varying $pH_B$. Solid arrow represents direction of decreasing $pH_B$. When $pH_B$ is in the range between the 2PK's, the surface buffering is low with $pH_{PZC}$~7. Here $pK_a=10$ and $pK_b=5$. The lightly shaded region represents the $E_{OX}$ range used in this study and the dark shaded region represents the fields applicable during readout. (d) $\psi_O$ vs. $E_{OX}$ for varying salinity $n_O$. The unshaded region represents field during readout. Solid arrow represents the direction of increasing $n_O$. The maximum modulation in $\psi_O$ occurs for lower $n_O$. At the zero $E_{OX}$ condition, the surface sensitivity to varying $n_O$ is negligible. An applied positive or negative $E_{OX}$ can tune $\psi_O$ to be sensitive to changes in $n_O$. (e) $\psi_O$ vs. $E_{OX}$ for varying $pK_b$. $\psi_O$ is affected only in the $-E_{OX}$ region. Solid arrow represents the direction of increasing $pK_b$ (f) $\psi_O$ vs. $E_{OX}$ for varying $pH_B$ with $pK_a$ and $pK_b$ flipped. Solid arrow represents the direction of increasing $pH_B$. Maximal buffering is observed in the range between the 2pK's.

Figure 10:
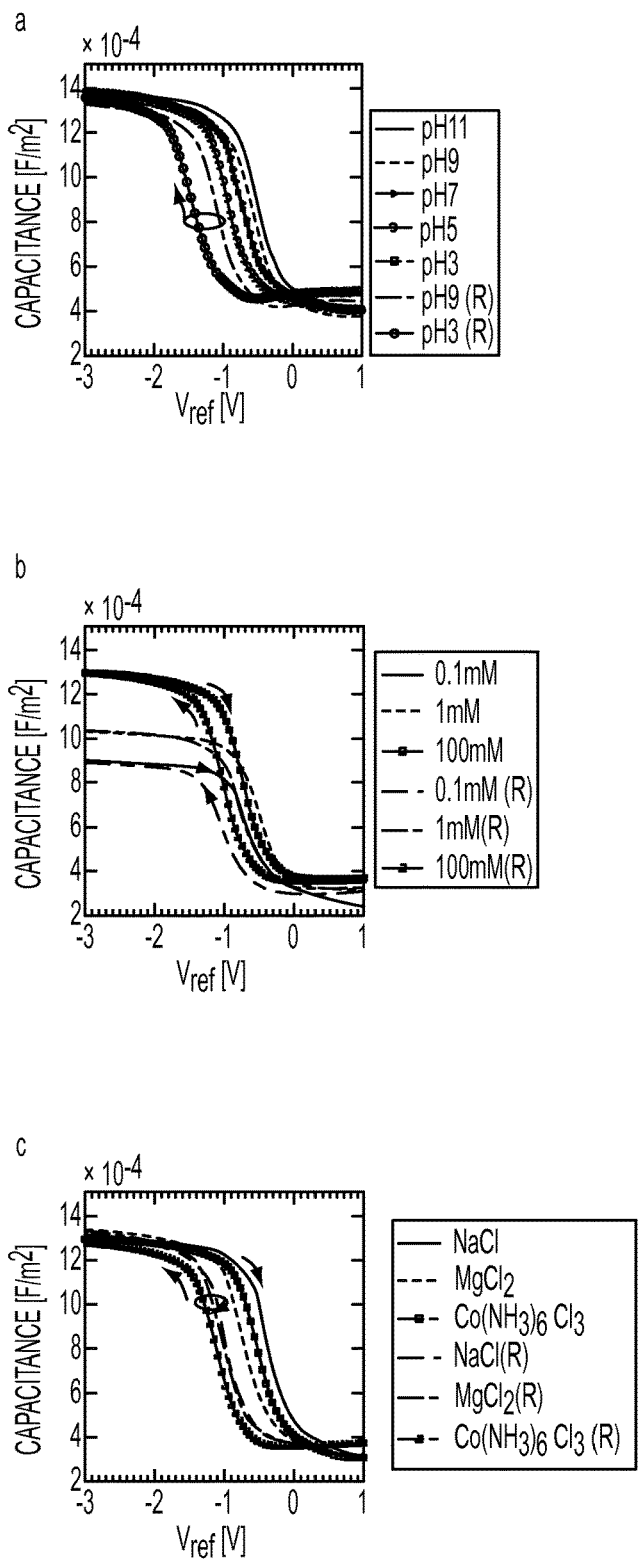

FIG. 10 shows experimental CV analyses depicting $V_{FB}$ shifts for, (a) varying $pH_B$. A strong $pH_B$-dependent hysteresis is observed while performing cyclic sweeps. A lowering in $V_{FB}$ is observed when the reference electrode is swept from positive to negative voltages implying a net positive remnant surface charge (b) varying bulk ion concentration ($n_O$). The hysteretic window is insensitive to pH while the accumulation region capacitance is dependent on $n_O$ and (c) varying cationic valency (z). Varying (z) influences the double layer composition which further influences $\sigma_O$. Divalent cations shift the $V_{FB}$ lower while trivalent ions induce a slight increase. $C_{DL}$ is lower for the trivalent cations. Here (R) denotes the reverse sweep in (a-c).

Figure 11:
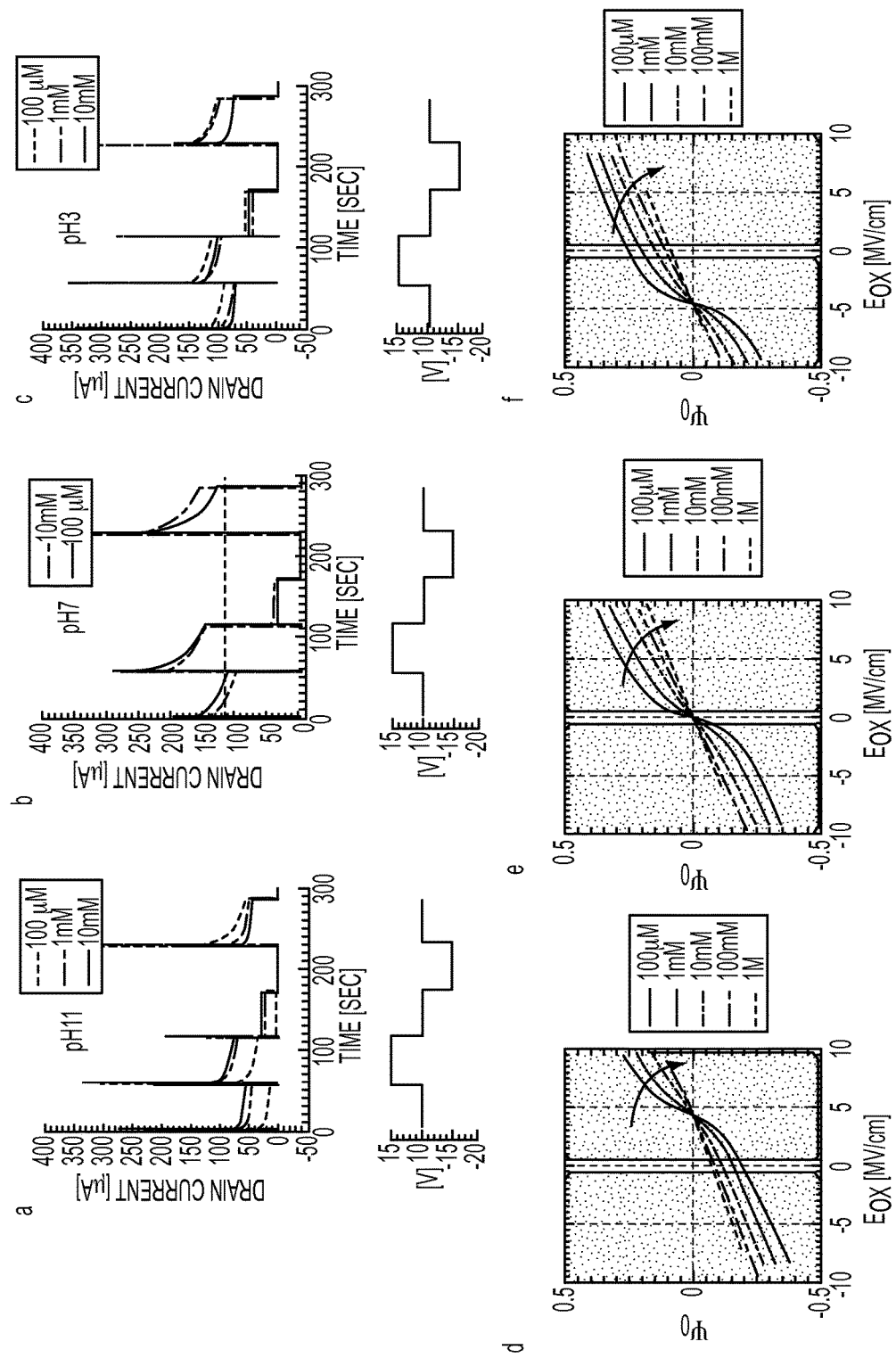

FIG. 11 shows transient recordings under CG pulse trains. Drain current output as a function of varying $n_O$ at (a) $pH_B=11$, (b) $pH_B=7$ and (c) $pH_B=3$. The pulse train amplitude and duration are shown under each figure. Calculated $\psi_O$ as a function of $E_{OX}$ for varying $n_O$ (d) $pH_B=11$, (e) $pH_B=7$ and (f) $pH_B=3$, using $pK_a=10$ and $pK_b=5$. At $pH_B=11$, $\psi_O$ is net negative for $E_{SG\_OX}$ close to $0 \frac{MV}{cm}$ and becomes more negative with decreasing $n_O$. This is reflected in the current levels during the transient recordings. At $pH_B=7$ the current levels flip when $E_{SG\_OX}$ is switched from positive to negative since $\psi_O$ is positive at the positive $E_{OX}$ and negative at negative $F_{OX}$. At $pH_B=3$, $\psi_O$ is net positive and increases with decreasing $n_O$. In all three cases, the drain current is higher between 230-285 seconds than the initial state between 0 and 60 seconds. This is attributed to net positive charge due to field-induced protonation which remains after the negative gating pulse is relaxed. This is similar to the observed hysteresis in FIG. 10. The un-shaded regions in (d-f) represent the fields during readout. Solid arrows in (d-f) represent the direction of increasing $n_O$.

Figure 12:
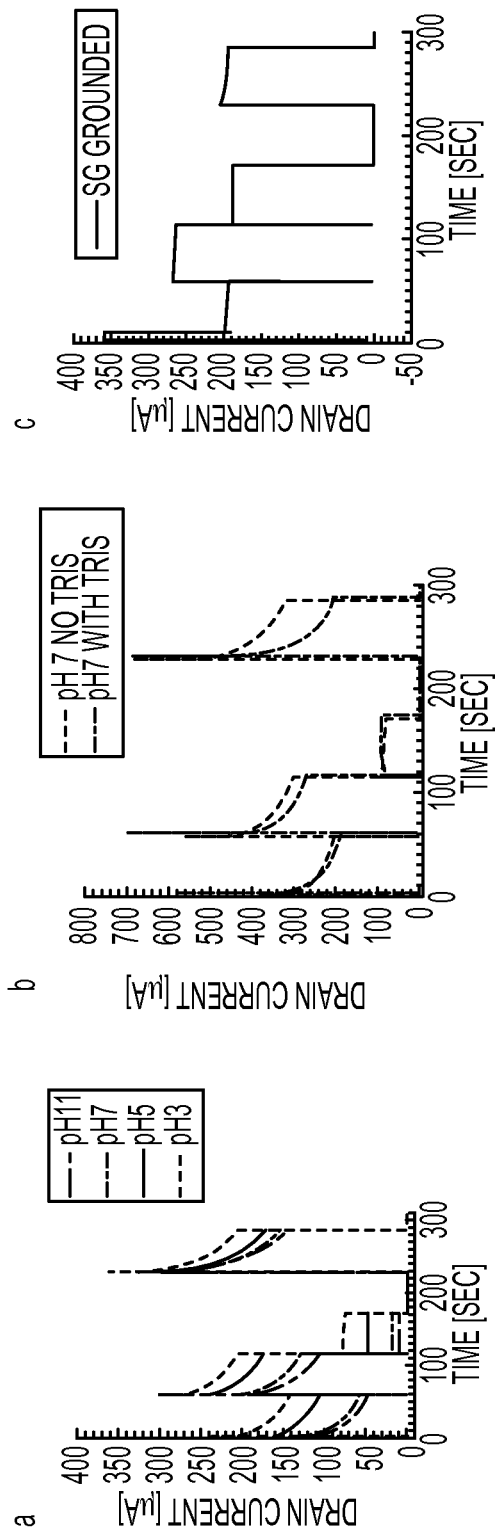

FIG. 12 shows (a) high resolution transient recording showing variation in drain current for the CG pulse train (described in the main body) for variations in $pH_B$. The increase in the current levels after the application of $-15V$ on the CG is attributed to surface protonation resulting in a remnant positive $\psi_O$. (b) Effect of adding a competing solution buffer (Tris buffer) at $pH_{B7}$. The current level after the application of $-15V$ does not increase to the same extent as before owing to scarcity of available protons, (c) transient current with the SG directly probed and CG pulsed. The current levels before and after the $+15V$ and $-15V$ CG pulse remain the same, indicating a charge neutral FG condition.

Figure 13:
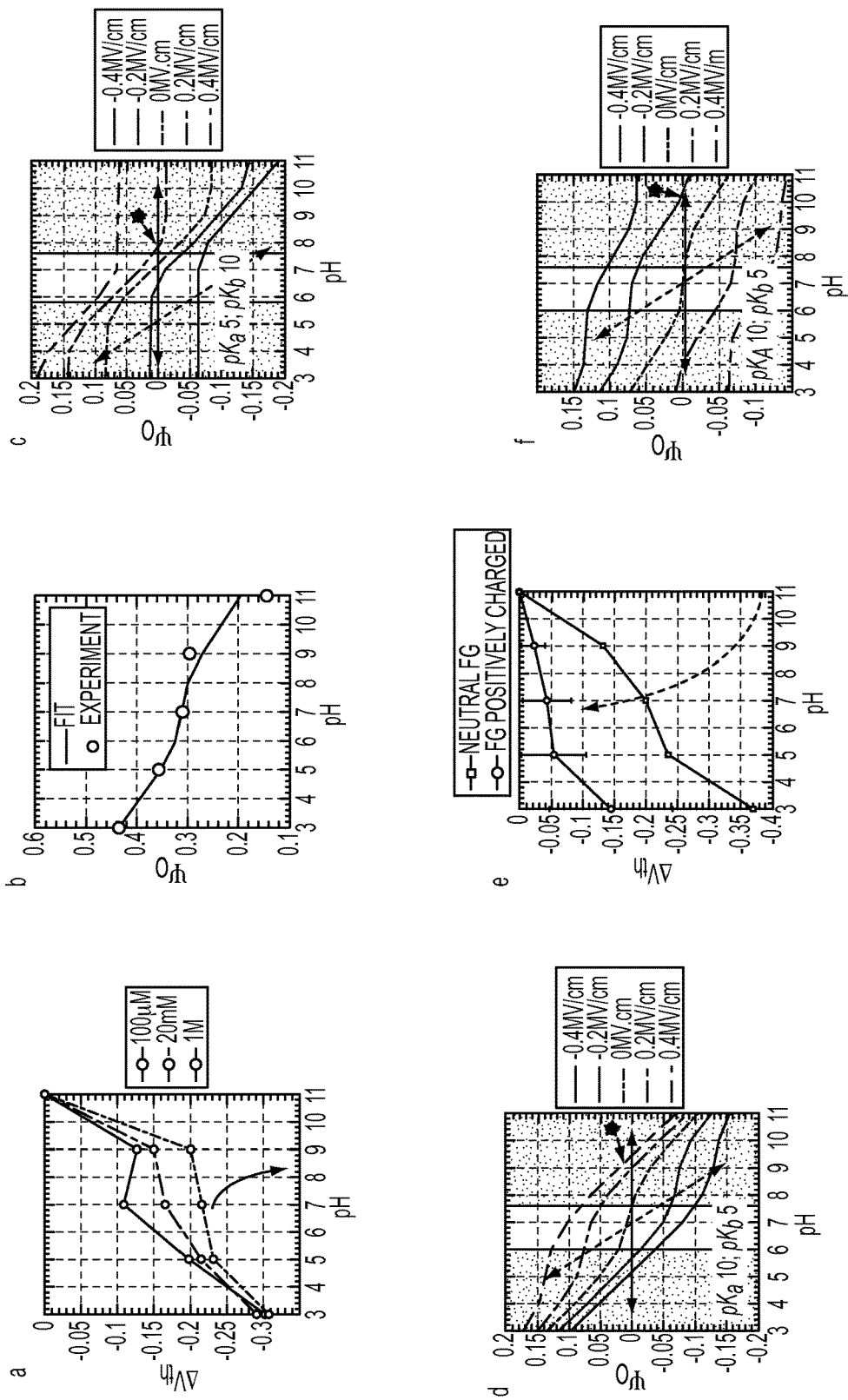

FIG. 13 shows (a) $\Delta V_{th}$ (representative of $\psi_O$) as a function of $pH_B$ for varying $n_O$. The slope of the $pH_B$ response reduces in the range between pK's while it increases at extreme $pH_B$ values. Cations are presumed to contribute to the slight increase in $\psi_O$ at high $pH_B$. Arrow indicates increasing order of $n_O$ (b) Theoretical fit to the experimental $pH_B$ response reveals $\Delta pK$ of 5 for a given surface site density of $10^{17}$ m$^{-2}$. $\psi_O$ vs. $pH_B$ for varying $E_{OX}$ with (c) $pK_a<pK_b$ and (d) $pK_a>pK_b$. Both responses indicate a shift in $pH_{PZC}$ (star) towards higher $pH_B$ as $E_{OX}$ is increased while the pH insensitive region shifts towards higher $pH_B$(c) and lower $pH_B$ (d), with increasing $E_{OX}$ respectively. This is primarily due to the different ionization states of the surface dependent on the choice of $pK_a$ and $pK_b$. (e) Experimentally extracted $pH_B$ response as a function of positive $E_{OX}$ in the SG oxide, achieved by $+Q_{FG}$. Results show the pH insensitive region shifts towards lower $pH_B$. Error bar represents average over 3 experimental runs. (f) $\psi_O$ vs. $pH_B$ for varying $E_{OX}$ with $pK_a>pK_b$ and lower $N_s$ ($5 \times 10^{16}$ m$^{-2}$). The modulation in $pH_{PZC}$ is a lot more exaggerated.

Figure 14:
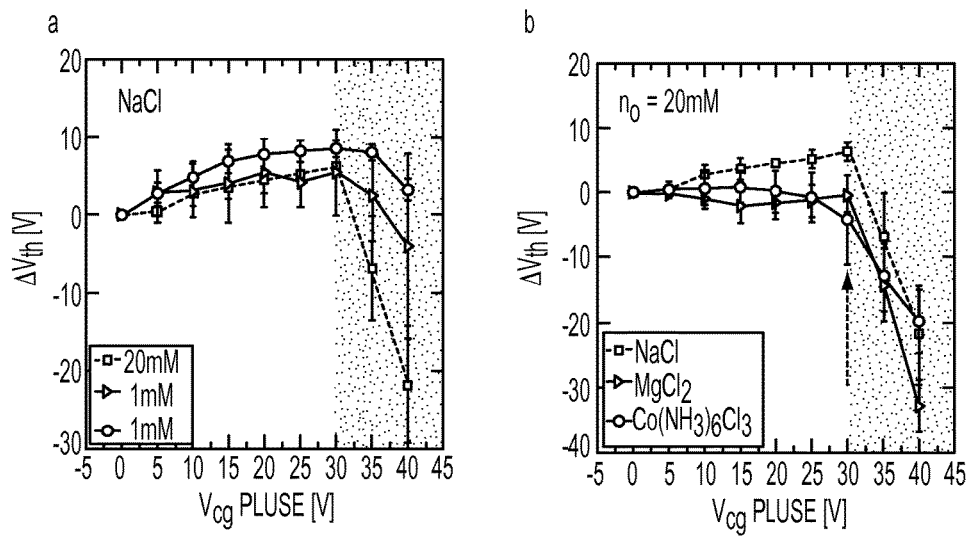

FIG. 14 shows $\Delta V_{th\_CG}$ as a function of the CG pulse amplitude for variations in (a) $n_O$ for a NaCl electrolyte and (b) cationic valency for floating gate based sensor structure with an amplification ratio of 20 at a bulk $n_O$ of 20 mM. An initial increase in $\Delta V_{th}$ at low to moderate CG voltages is attributed to surface deprotonation and a net remnant negative $\psi_O$. Due to asymmetric CG and SG capacitances, $V_{FG}$ is pulled closer to $V_{REF}$. This ensures that at sufficiently high $V_{CG}$ the $V_{FG}$ does not rise much which leads to large $E_{CG\_OX}$ for FN tunneling. Reduction in $n_O$ and $C_{DL}$ weakens the coupling between the FG and $V_{REF}$, causing $E_{CG\_OX}$ and net $Q_{FG}$ to reduce. Varying cationic valency indicates more pronounced shifts in $\Delta V_{th\_CG}$ around the knee point (i.e. where tunneling begins) especially with trivalent salts in comparison to mono and divalent salts. A decrease in the overall $\Delta V_{th\_CG}$ with trivalent salts upon tunneling is consistent with the notion that $C_{DL}$ is also decreasing. Error bars represent an average over 3 experimental runs.

Figure 15:
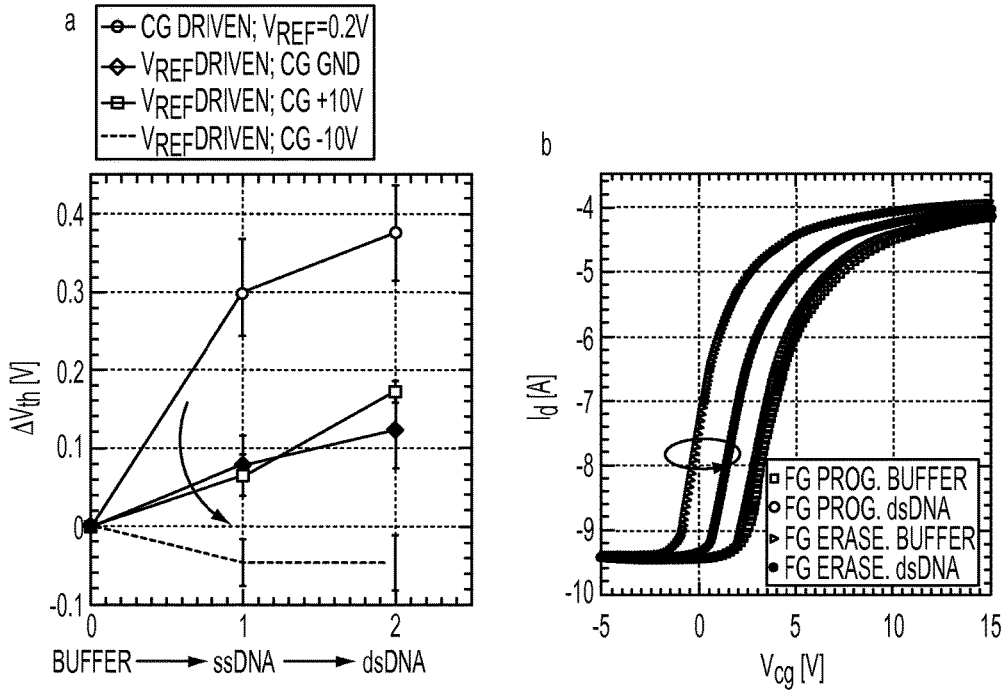

FIG. 15 shows (a) a comparison between reference electrode and CG readouts during DNA immobilization and hybridization. A $+10V$ CG bias during $V_{REF}$ readout renders a $+E_{SG\_OX}$ in the SG oxide while a $-10V$ renders a $-E_{SG\_OX}$ CG driven readout with $V_{REF}$ at 0.2V shows a larger $\psi_O$ shift prior to hybridization mainly due to different $E_{SG\_OX}$ conditions. During hybridization however $\Delta\psi_O$ (~60 mV) is only marginally different between CG and $V_{REF}$ readout. At $-E_{SG\_OX}$ conditions a slight reversal and diminished $\psi_O$ is observed suggesting that the underlying field affects the net charge at the interface. At such field magnitude (0.05 V/nm) DNA desorption does not occur but the ionic screening can be perturbed. FIG. 15(b) shows the effect of electron and hole injection into the FG prior to dsDNA (24mer) addition. With electrons injected, a very small shift in $V_{th\_CG}$ is observed, which for the given capacitive ratio of $-15$ implies a $\psi_O$ shift of approximately 10~15 mV. With hole storage the shift in $\psi_O$ is ~150 mV.

Figure 16:
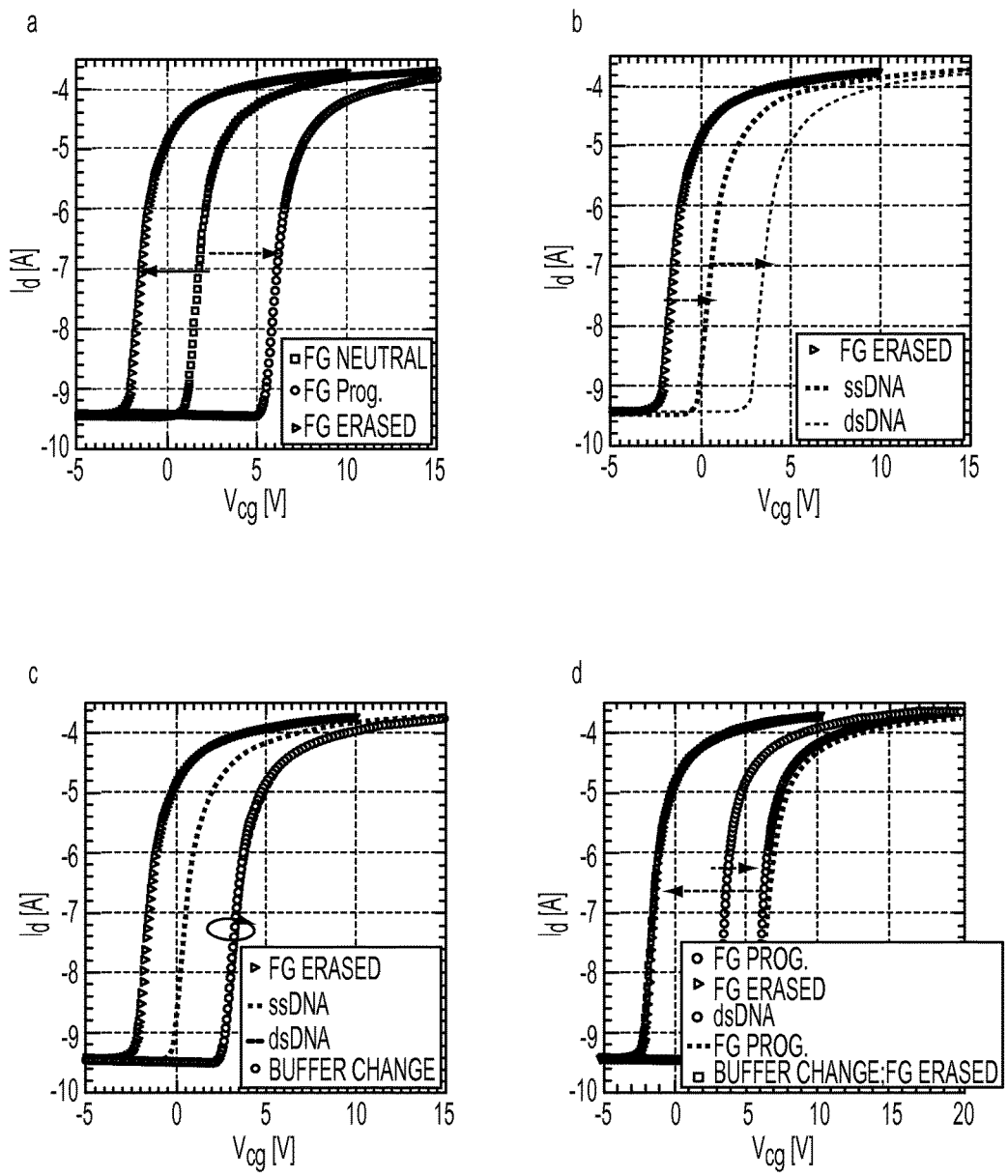
Figure 17:
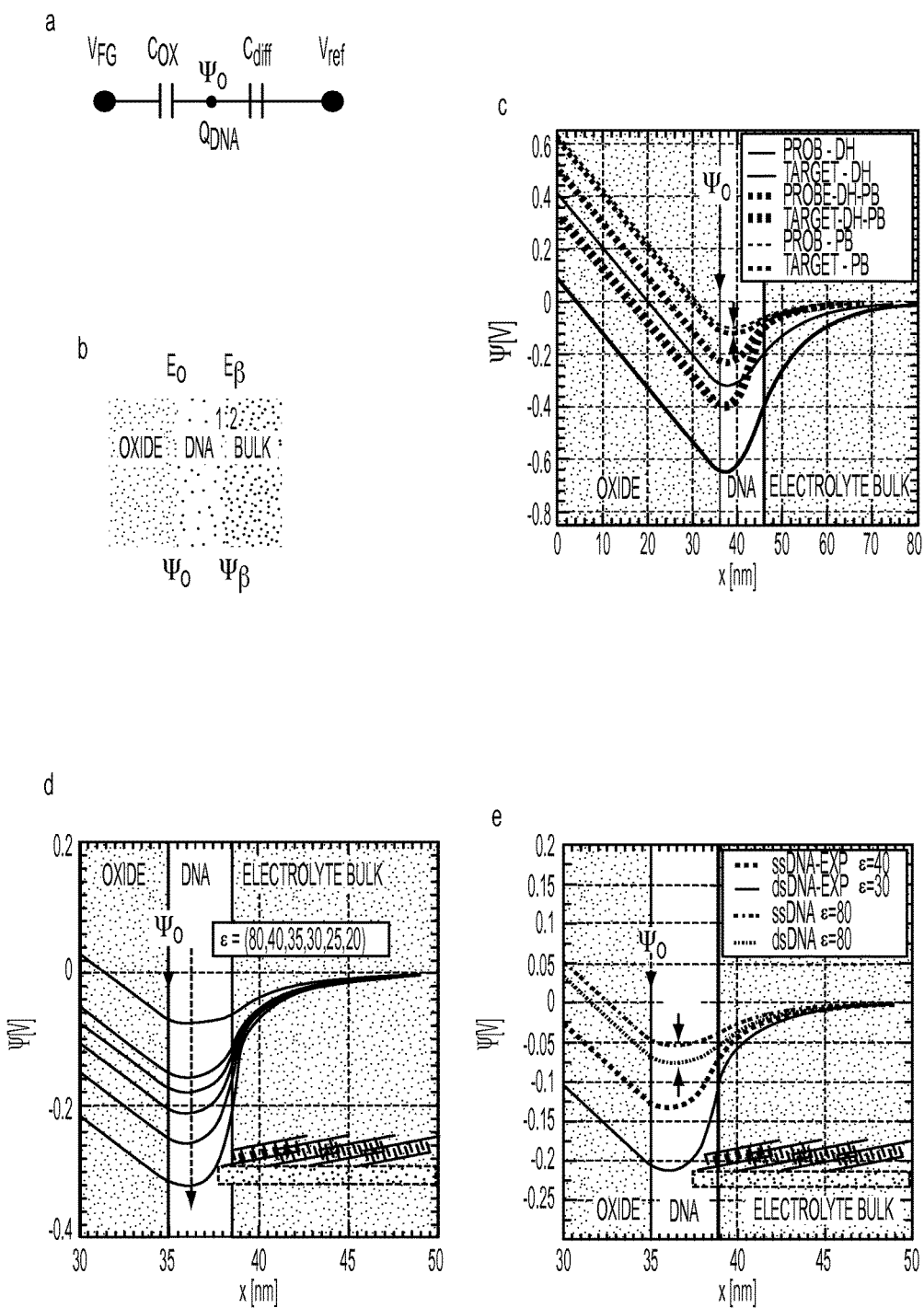

FIG. 16 shows (a) The floating gate based sensor structure with a poly-l-lsyine-coated sensing gate is exposed to buffer and subsequent tunneling operations are performed. Red (dotted) arrow indicates programming while the black (solid) arrow indicates erase. (b) DNA strands C1 and C2 are added to the chip under the erased conditions (electron tunneled out) which results in marked $V_{th\_CG}$ shifts (c) buffer exchange after step (b) indicates an unchanged surface state. (d) Programming (electron tunneled in) the device after step (c) indicates the SG surface state is now similar to when pure buffer was present. Subsequent buffer exchange and erasing creates a refreshed interface FIG. 17 shows (a) simplified capacitive model representing the FG-DNA interface (b) DNA-SG model representing the various interfaces, potentials and fields. $\psi_O$, $\psi_\beta$ represent the potentials at the SG interface and DNA-electrolyte interface respectively. $E_O$ and $E_\beta$ are the respective fields across the SG interface and DNA electrolyte interface respectively. The numbers 1 and 2 represent the discontinuity in E-field across the DNA electrolyte interface due to permittivity differences (c) Potential profile across the capacitive network shown in (a) for various ionic screening models within the DNA membrane. Debye Huckel (DH) screening represents the linearized Poisson Boltzmann (PB) approximation. Notice that when ionic screening within and outside the membrane is both low, the $\psi_O$ shift is maximum. The nonlinear PB approximation results in a much lower shift in $\psi_O$. (d) Potential profile including the partition energy barrier to account for the ion charge density within the DNA membrane. The self energy of ions ($\Delta G_m$) is lowered in the DNA membrane represented by varying $\varepsilon_{eff}$. This leads to a lower charge density within the DNA membrane and larger change in $\psi_O$. The inset depicts the orientation of DNA considered in the simulation. (e) Comparison of ($\Delta\psi_O$) hybridization signals between a PB approximation with $\varepsilon_{eff}=80$ and an approximate extracted for CG driven experimental data. Experimental evidence indicates tight packing of DNA at the surface resulting in ion exclusion and a more pronounced $\psi_O$ shift.

Figure 18:
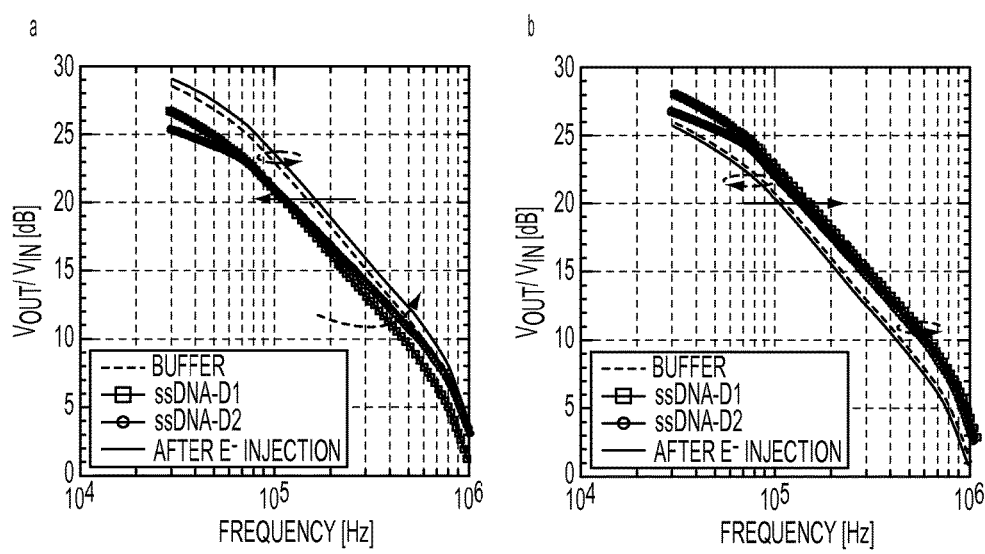

FIG. 18 shows (a) DNA strands D1 and D2 are added to the chip in sequence and the frequency response before and after hybridization is monitored. A clear relaxation is observed ($Z_1$) after hybridization, indicating dispersion mechanisms are possibly tied to the structure and stiffness of the DNA strand. Charge injection is shown to refresh the surface with a recovery of impedance. (b) Step (a) repeated for strands C1 and C2 showing the molecular weight dependence on the formation of $Z_1$ which is very weak. The initial shift in $P_1$ is attributed to shift in resistance due to an inefficient relaxation at extremely small molecular length scales.

Figure 19:
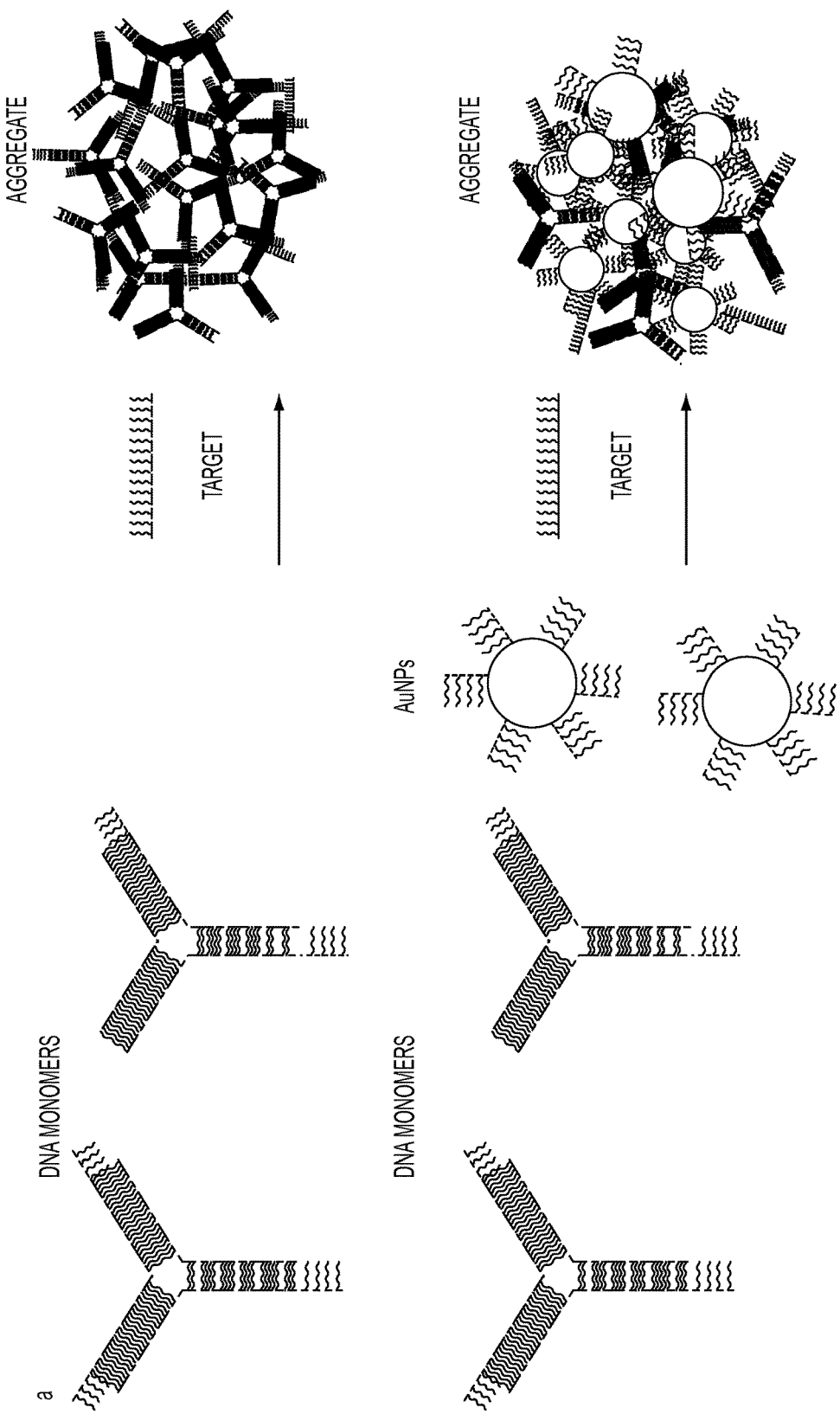

FIG. 19 shows self-assembly of Y-DNA monomers tagged with probe sequences when target DNA is introduced, where aggregation is detected through impedance spectroscopy performed on a floating gate based sensor apparatus.

Figure 20:
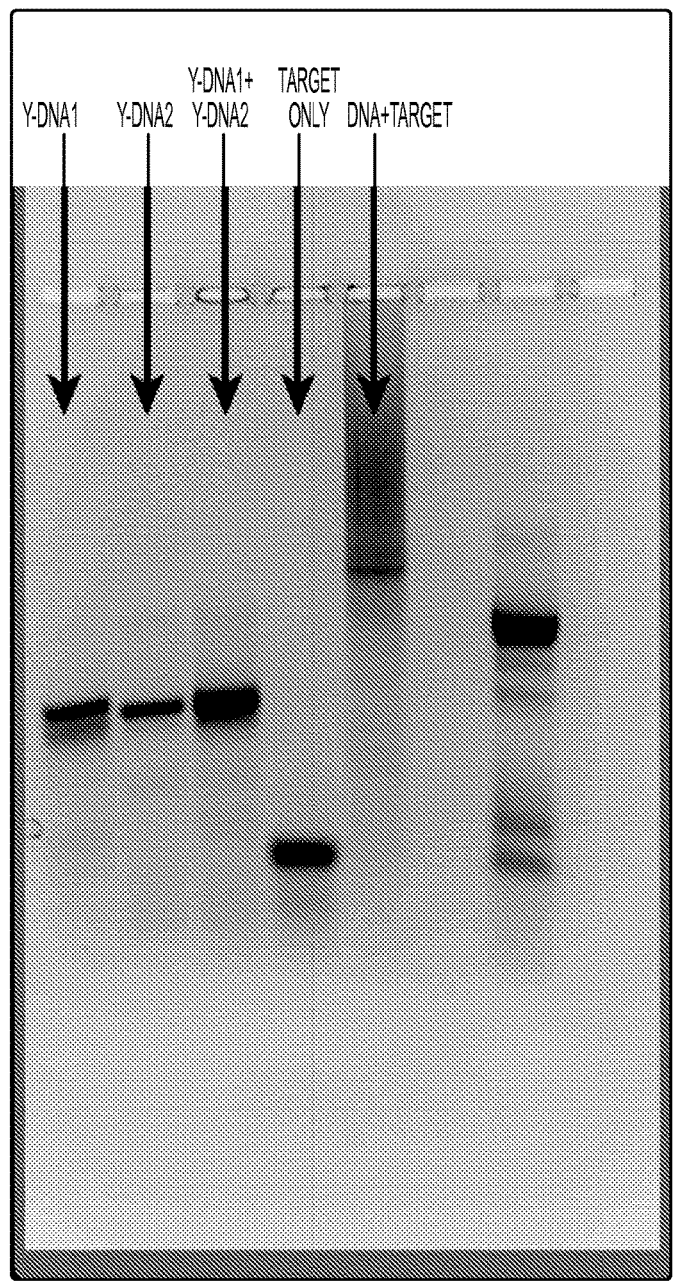
Figure 20:
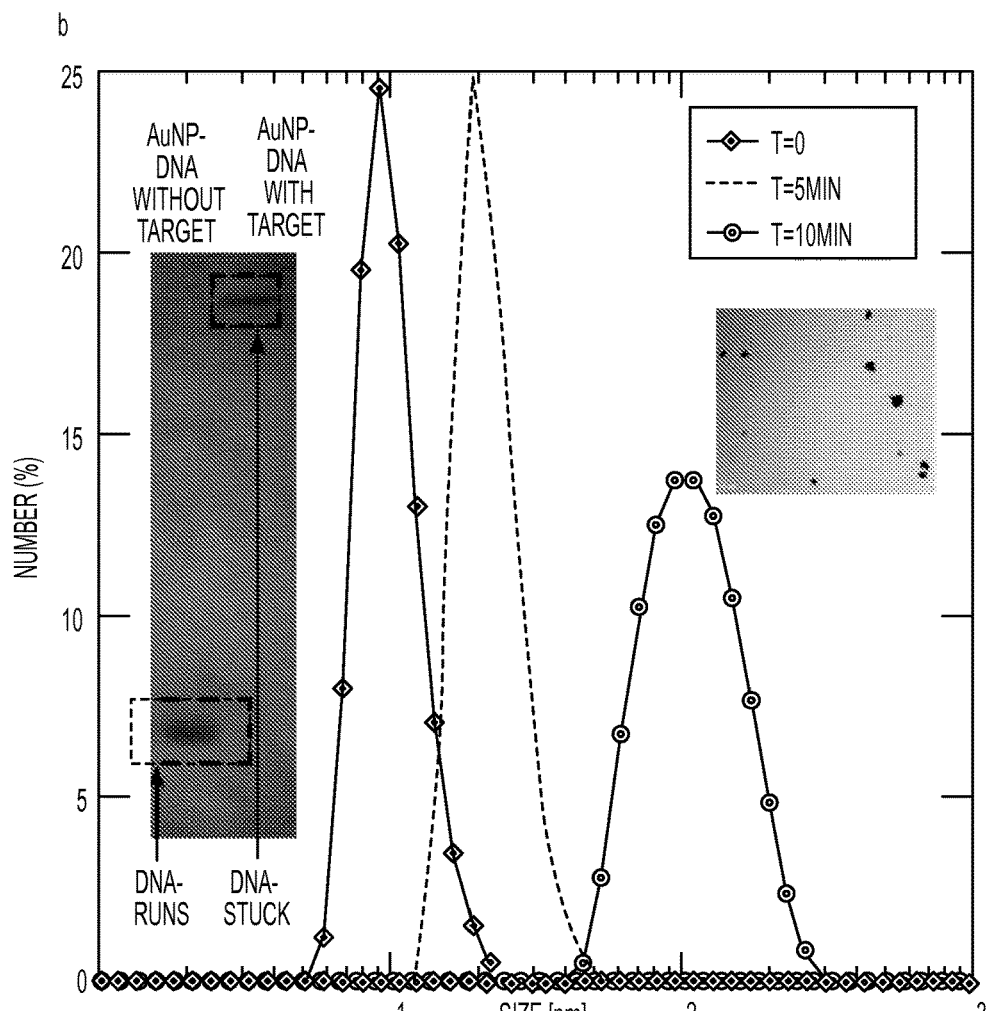

FIG. 20 shows (a) Gel electrophoresis study of Y-DNA aggregation shows a large smear as pathogen is added indicating aggregation. Absence of target results in a clear run (b) DLS study of Y-DNA-aggregation shows a time dependent increase in aggregate size reaching ~15 nm. (c) Gel electrophoresis study of Y-DNA-AuNP aggregation shows DNA stuck with target present confirming increased aggregation. Absence of target or addition of mismatched target results in a clear run. Lowering in background salinity reduces the aggregation effect. (d) DLS measurement of the AuNP-Y-DNA mixture after target treatment. Gel electrophoresis (inset) once again shows aggregates stuck in well after target treatment.

Figure 21:
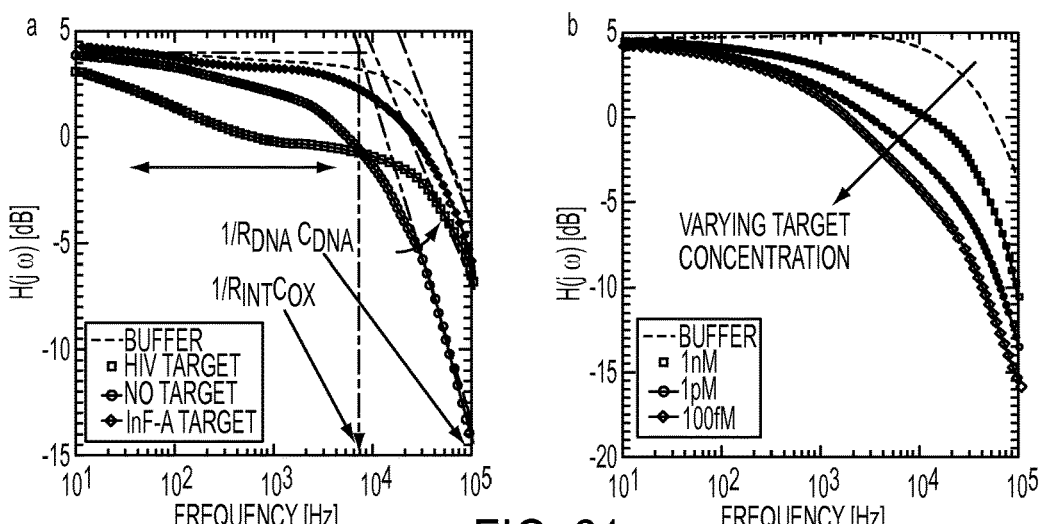

FIG. 21 shows (a) frequency response of Y-DNA-target hybridization. Buffer represents 500 mM saline without Y-DNA. Addition of Y-DNA w/o target increases RDNA. Notice a clear relaxation in the presence of target (green horizontal arrow). Time constants depict the dependence on CDNA and RDNA (b) LOD for Y-DNA mixtures shows an increase in RDNA as target concentration decreases, synonymous with low aggregate count and increased surface coverage by un-reacted monomers. (c) Quasi-static I-V response measured from the reference electrode, with the negligible and erratic shifts in VTH as a function of increasing target concentration implying screening limited responses.

Figure 22:
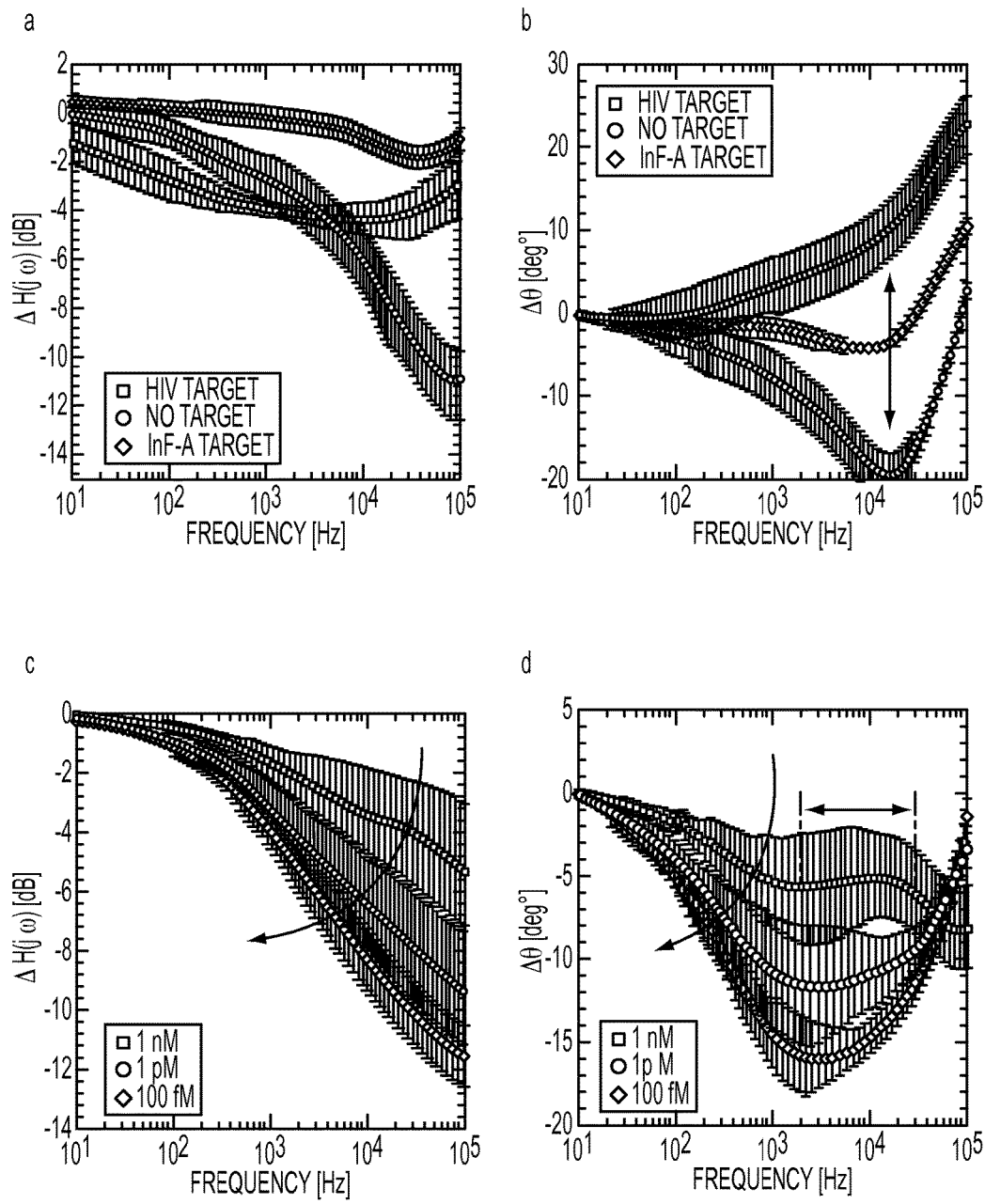

FIG. 22 shows (a and b) ex-situ magnitude and phase under varying target conditions; and (c and d) effect of varying target concentration keeping the Y-DNA concentration fixed. At low target concentrations P1 is determined by the unreacted monomers. As target concentration increases aggregates form reducing RDNA and P1 moves out. A relaxation is subsequently observed (green arrow in (d)) indicative of aggregate detection due to increased polarizability.

Figure 23:
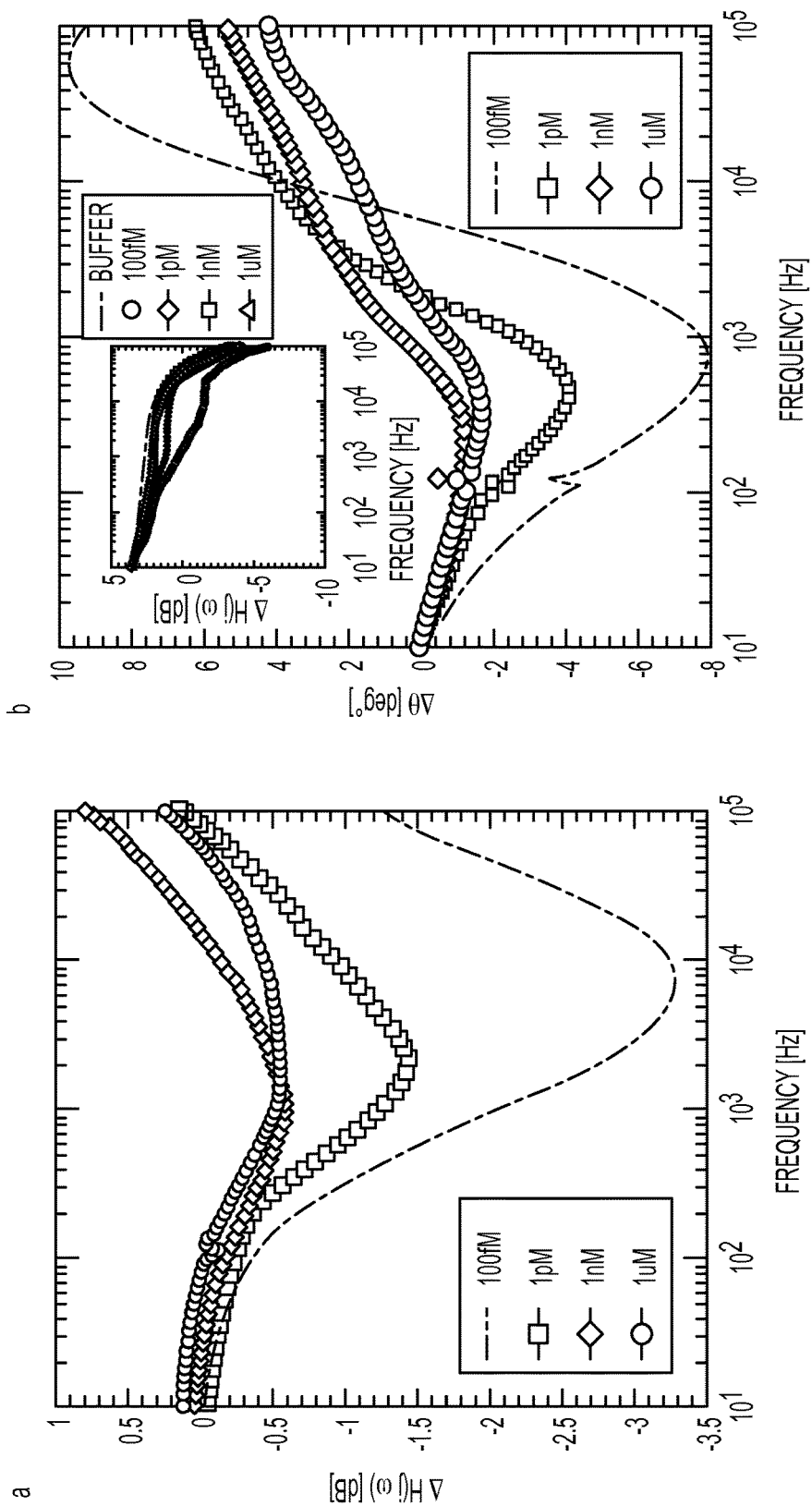

FIG. 23 shows ex-situ (a) magnitude and (b) phase shift for varying target concentration for Y-DNA monomers with AuNP tags. The P1-Z1 response is more dramatic and occurs at lower frequencies indicative of larger size aggregates and a more pronounced shift in the relaxation time constant. Inset in (b) depicts the transfer function amplitude characteristic prior to baseline subtraction. A relaxation is observed even for 100 fM target concentrations (red).

Figure 24:
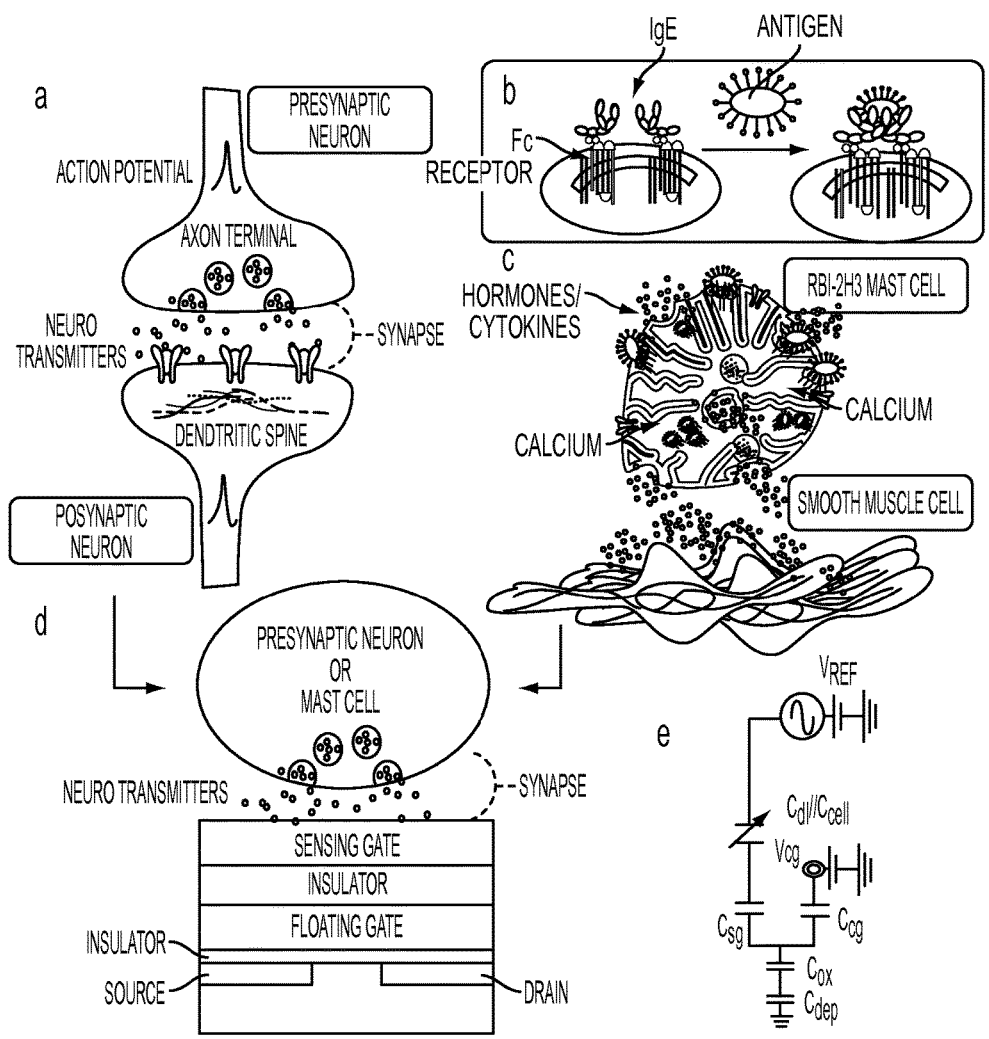

FIG. 24 shows (a) a schematic of a neural synapse showing the post-synaptic and pre-synaptic nerve endings. An action potential in the pre-synaptic cell terminates with the fusion of vesicles and release of neurotransmitters (exocytosis) which impinge on the post-synaptic cell receptors. When the intracellular potential of the postsynaptic cell crosses a certain threshold the neuron fires inducing further electrical activity; (b) Cross-linking of the IgE upon antigenic stimulation, receptor clustering accelerates degranulation (c) Schematic of IgE sensitized mast cell degranulation by DNP BSA resulting in clear morphological change and hormonal release which subsequently stimulates smooth muscle cells through a receptor effector function (d) Replacing the post-synaptic neuron and smooth muscle cell with the floating gate based sensor apparatus effectively creates a cell-transistor biosensor in which the SG effectively serves as an electronic analogue of a synapse and receptor respectively (e) Circuit schematic of the floating gate based transistor with capacitively coupled control (CG) and sensing gates (SG) to a common floating gate (FG). The CG and SG serves as threshold weights and after a certain threshold (VTH) is reached the transistor turns on.

Figure 25:
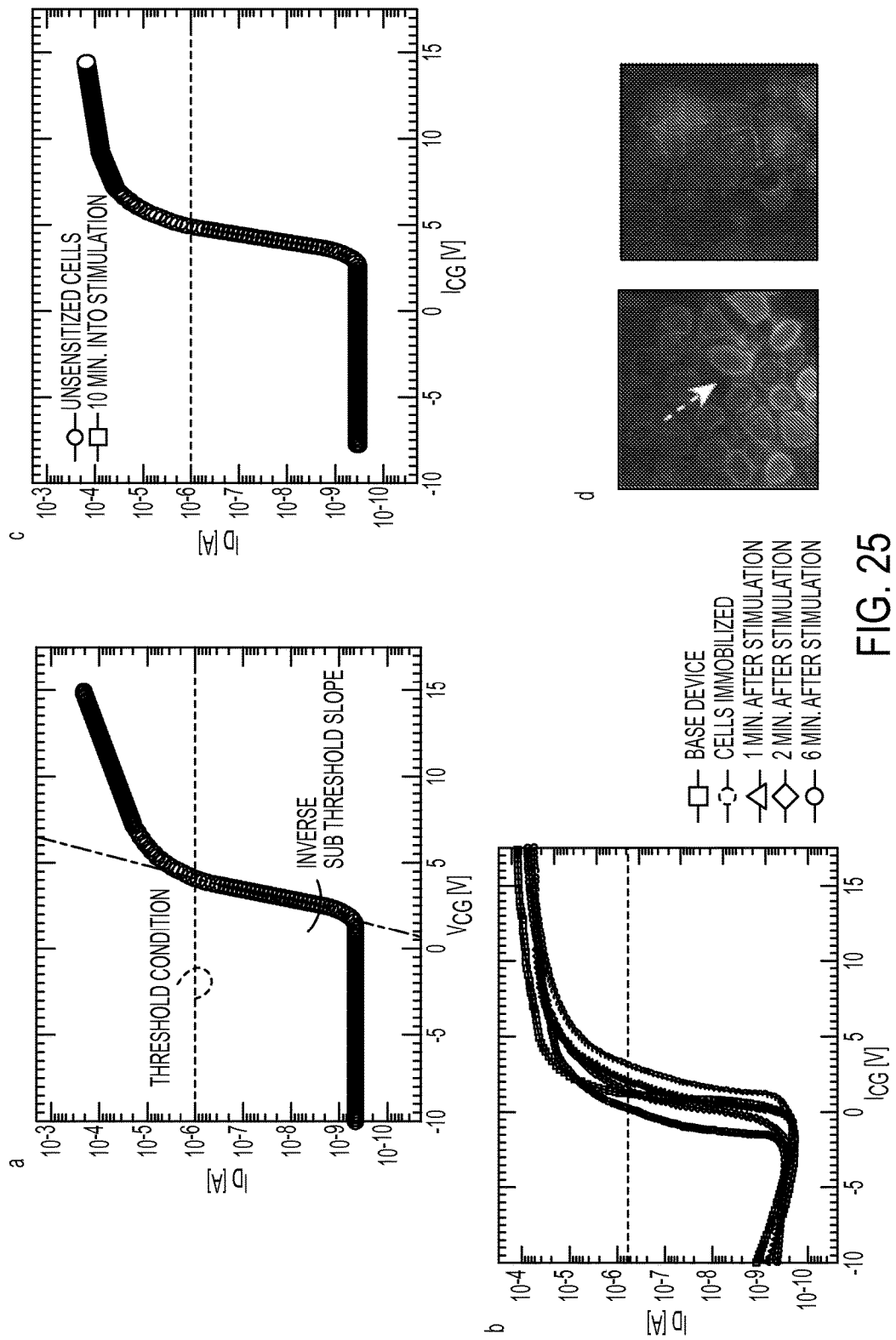
Figure 25:
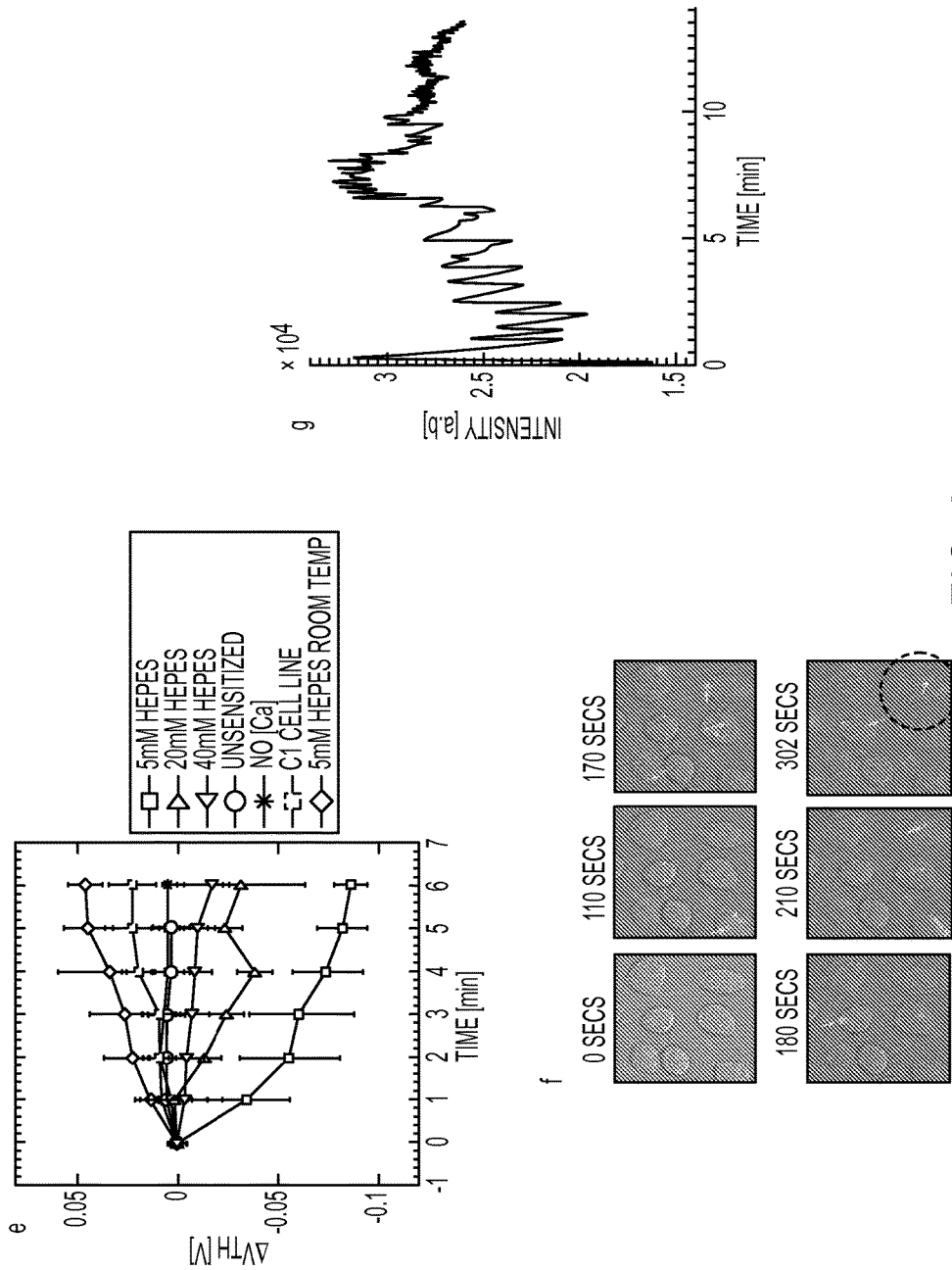

FIG. 25 shows (a) auasi-static IV response of the floating gate based sensor apparatus operated from the CG. The VTH is calibrated at constant current of 1 µA, while the subthreshold slope is indicative of capacitance loading at the SG. (b) IV response to IgE sensitized mast cell degranulation upon antigenic addition. Notice a clear reduction in VTH as degranulation proceeds with a more positive surface potential evolution. (c) Unsensitized cells show no shift in VTH as degranulation proceeds. (d) Fluorescent images of IgE sensitized mast cells (arrow) before (left) and after (right) stimulation. Clustering of IgE receptors is clearly observed along with morphological change. (e) Surface potential shifts as function of time after mast cell stimulation with DNP BSA under various conditions. (f) Time lapse confocal imaging of FITC-dextran labeled mast cells after stimulation with DNP-BSA. FITC-dextran uptake occurs overnight. Fluorescence is quenched due to the low pH inside the vesicle. Upon release into the extracellular space the fluorescence recovers (green flash). The time stamps reveal a heightened detection of release events (white arrows) a few minutes after antigen addition. (g) Energy density indicative of fluorescent intensity for each subsequent time stamp indicates similar kinetics to (e).

Figure 26:
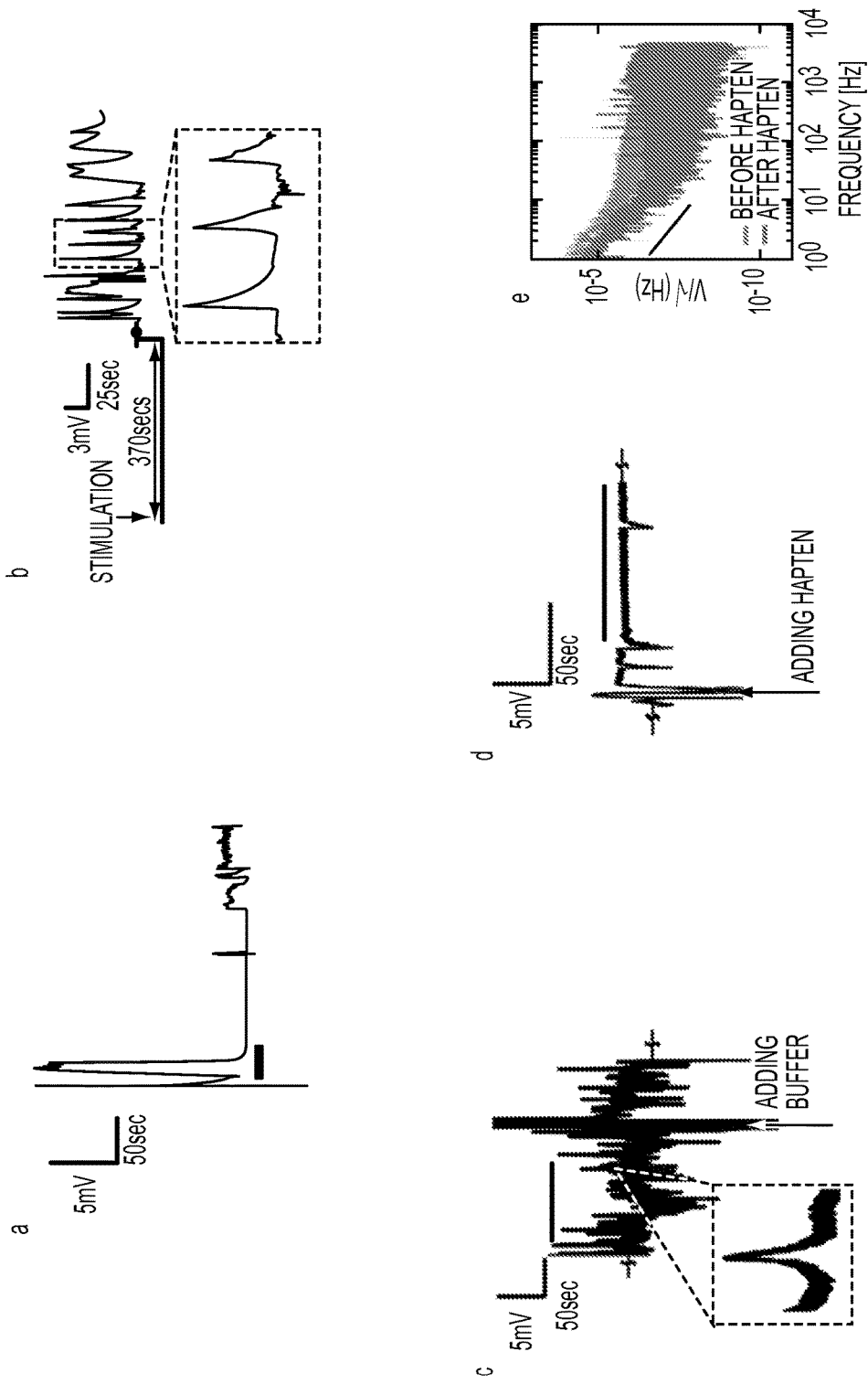

FIG. 26 shows mast cell transient responses: (a) Immobilized mast cells response to antigenic stimulation by DNP BSA in tyrodes solution. Antigen addition (represented by the grey bar) is followed by a period of inactivity for approximately 2~3 minutes after which activity begins to ensue. (b) Typical transient surface potential fluctuations approximately 5 minutes after stimulation depicts sharp rise and gradual recovery in surface potential over the time course of seconds. (c) Adding tyrodes solution to stimulated mast cells (green arrow) results in persistent activity. The cells are not displaced during addition of various stimulants. Notice (inset) typical rise and fall patterns in surface potential. (d) Monovalent hapten added subsequently (green arrow) to the recording shown in (c). A reduction in activity and collapses of the signal to basal noise level is immediately observed. This indicates that a dominant contribution to surface charging is IgE aggregation induced signalling. (e) PSD analysis of a 100 second portion of (c) and (d) clearly shows a reduction in the Nyquist-Johnson noise upon hapten addition. A slight reduction in 1/f noise and a more significant decrease in thermal noise indicate that the cell activity which introduces a resistive "cell adhesion" component of noise due to uptake and release of ions and mediators at the interface has reduced.

Figure 27:
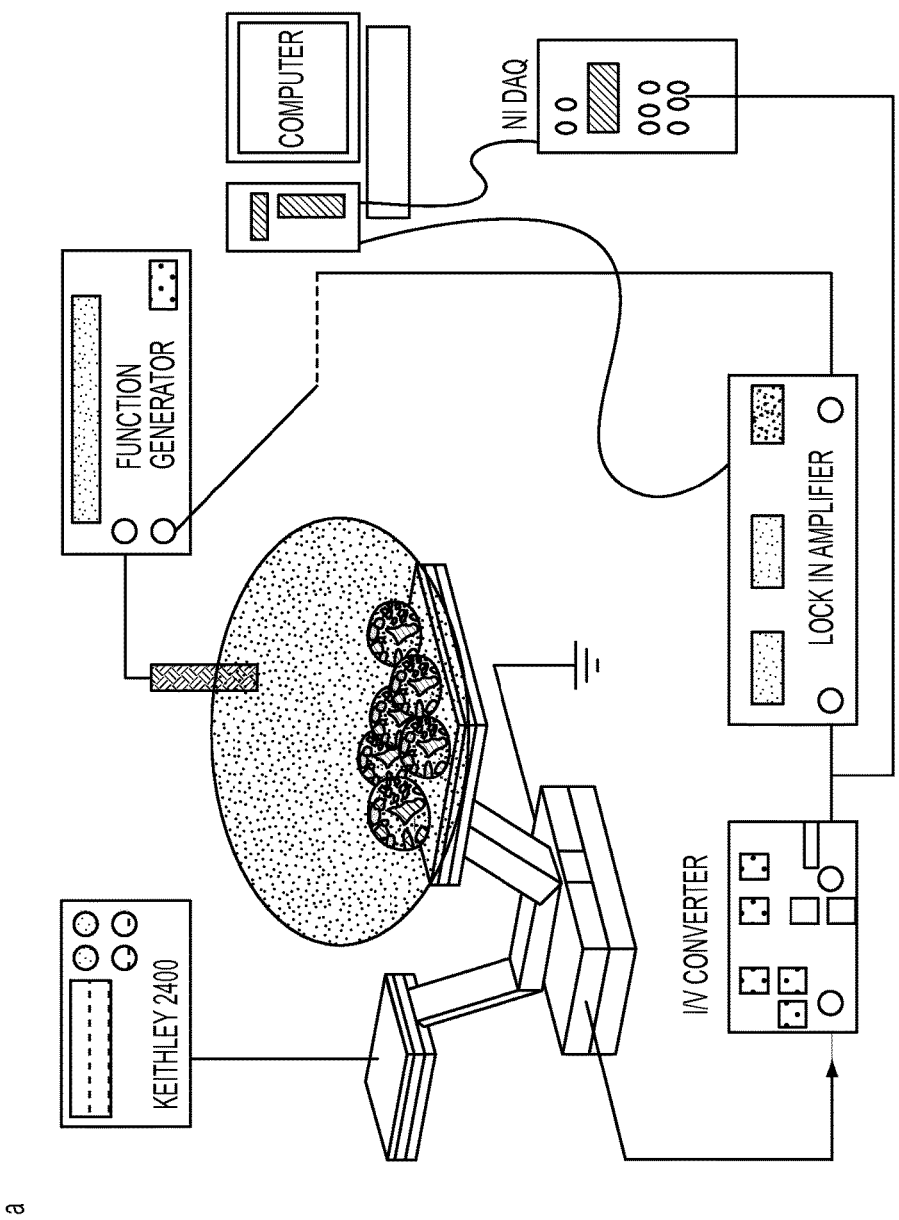
Figure 27:
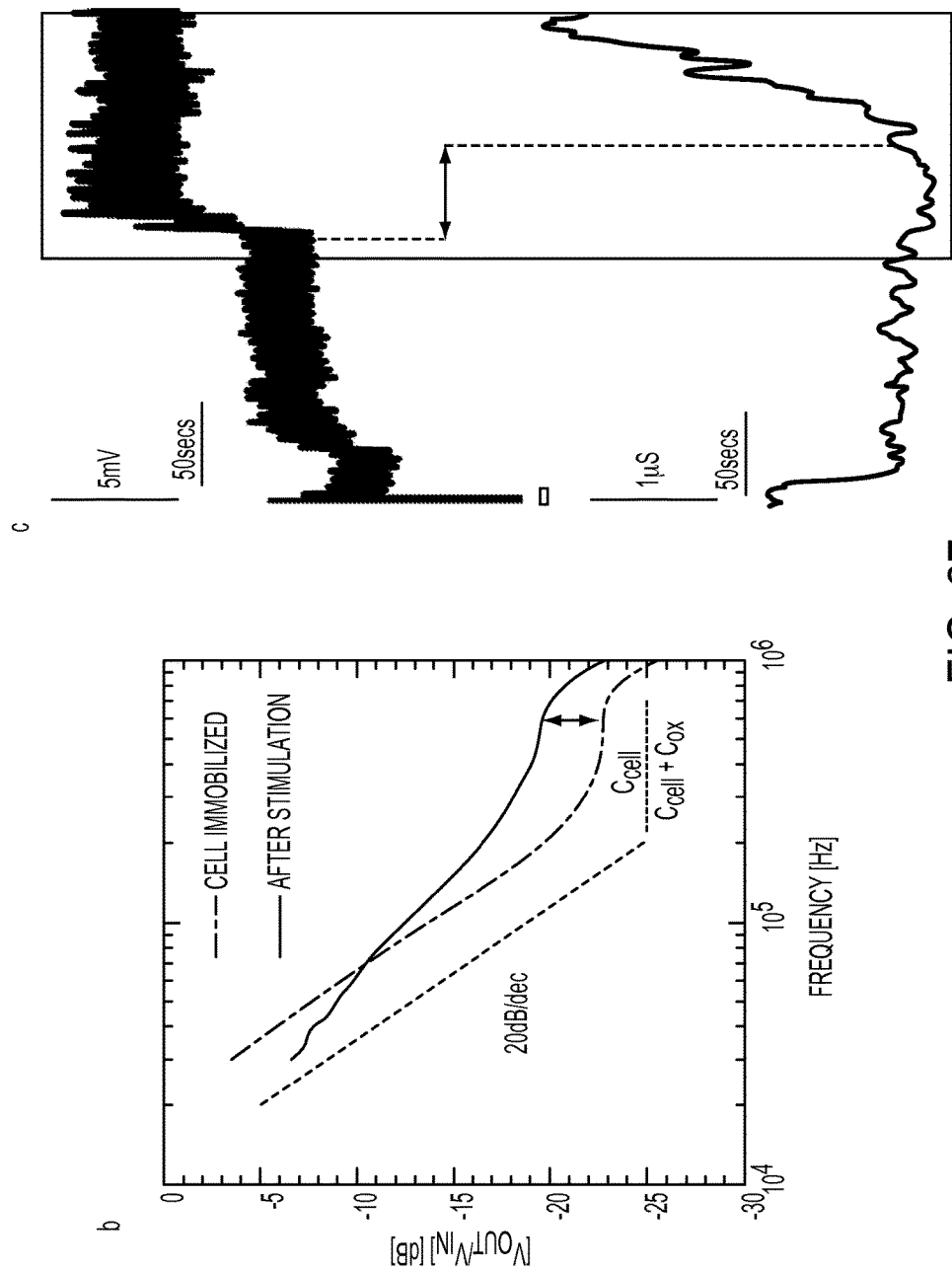

FIG. 27 shows (a) measurement setup showing the simultaneous impedance and charge detection by the split excitation technique on the floating gate based sensor apparatus. The CG delivers the DC excitation while the reference electrode delivers the AC small signal (0.1V). The AC impedance magnitude signifies the transconductance as a function of frequency. (b) The pole-zero (Bode) responses before and after stimulation show the zero moving in, which is possibly due to the increase in cell membrane area during exocytosis. By a crude fit, we extract an overall increase in capacitance of ~0.1 pF, which includes the capacitance increase from all the cells immobilized on the surface. The shift in the first pole position is due to an increase in interface resistance and the shift in zero is mainly due to capacitance changes at the cell transistor interface. (c) Simultaneous surface potential and transconductance measurements by measuring the DC and AC components (at 40 KhZ) independently. As soon as stimulation is initiated, there is a slight delay in response after which shifts in surface potential are observed (upper). A concomitant increase in gm and hence capacitance is also observed (bottom) although there exists an initial decrease during stimulation. The change in capacitance shifts the transistor gm by ~1 µS.

Figure 28:
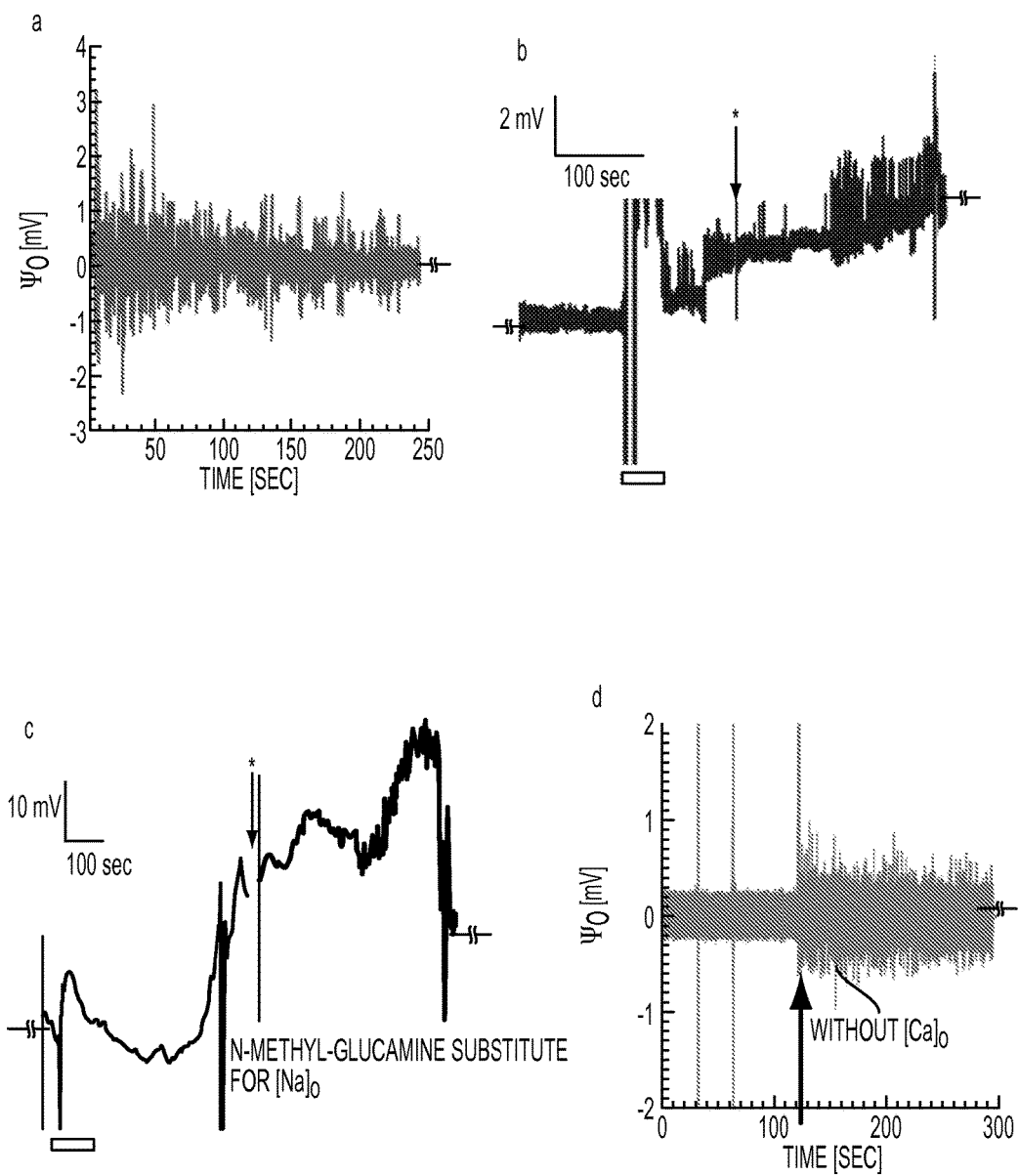

FIG. 28 shows transient responses of chromaffin cells: (a) Sample of activity after high KCl induced depolarization (high pass filtered) shows rapid fluctuations in surface potential, which suggests AP with peak-peak amplitudes reaching ~2 mV. (b) Effect of adding Ringer's solution rich in [Na]o to the transistors with cells previously bathed in NMG substituted Ringer's and stimulated with high KCl. Notice the steady shift in surface potential (not high pass filtered) indicates positive secreted charge along with rapid spikes resembling AP, suggesting that the transistor response is closely tied with [Na]o. (c) A 300-second recording of stimulated activity (not high pass filtered) in the presence of NMG substituted Ringer's shows clear increase of surface potential shifts with time, but AP's are reduced. (d) Stimulated response of chromaffin cells in the absence of [Ca]o. The presence of AP persists.

Figure 29:
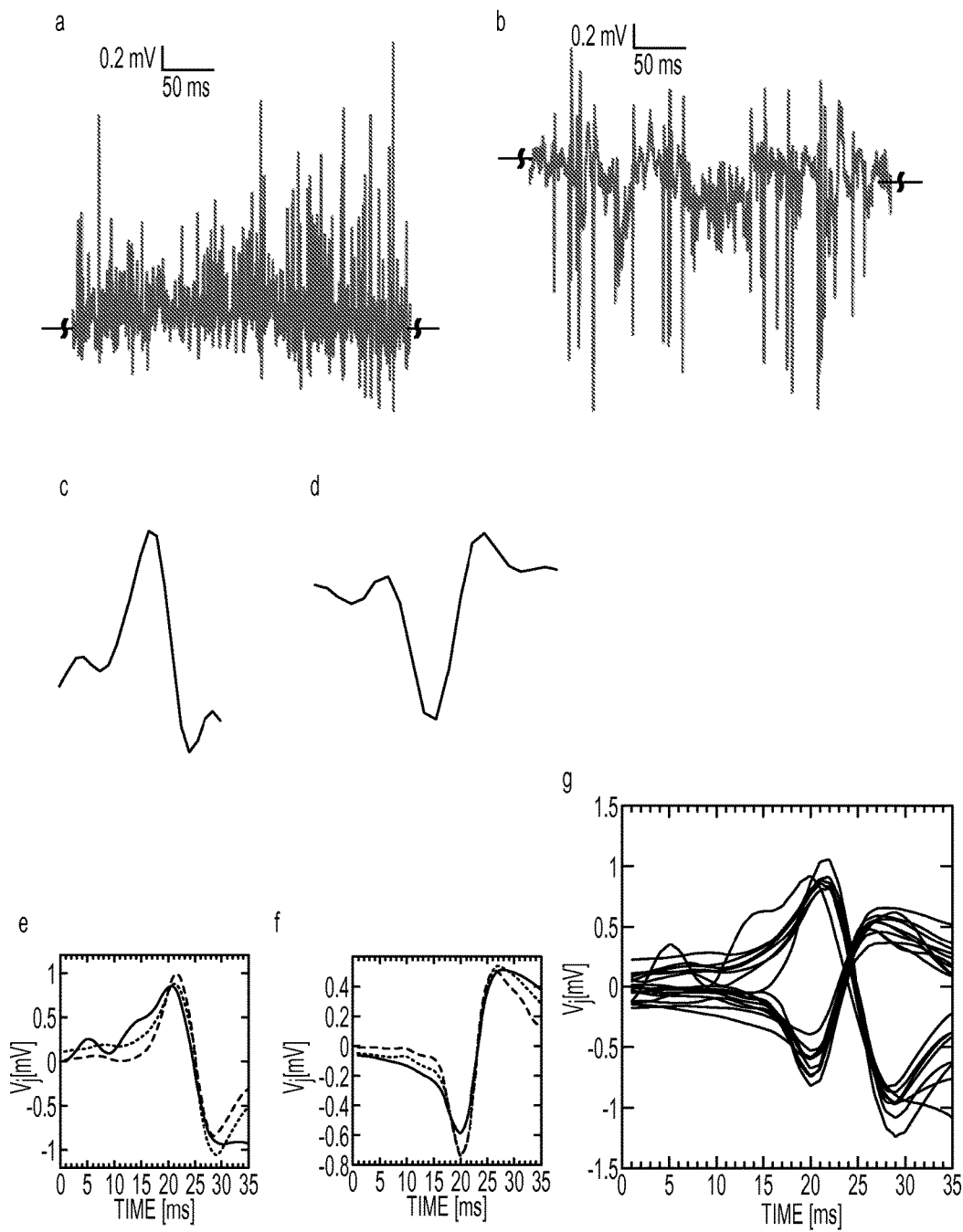

FIG. 29 shows (a) transient activity for chromaffin cell stimulation depicting biphasic waveforms observed during the rising phase of an intracellular AP. (b) A trace of inverted capacitive waveforms. (c)&(d) Templates of the biphasic and inverted AP waveforms used for matched filtering. (e) Average match filter response for 3 independent experiments shows the shape and amplitude of the biphasic response recovered. (f) Inverted capacitive response for the same. (g) A number of hits are encountered by performing an amplitude threshold followed by match filter operation. The shape and amplitudes of the waveforms are very homogenous and amplitudes lie between 1-2 mV peak to peak.

Figure 30:
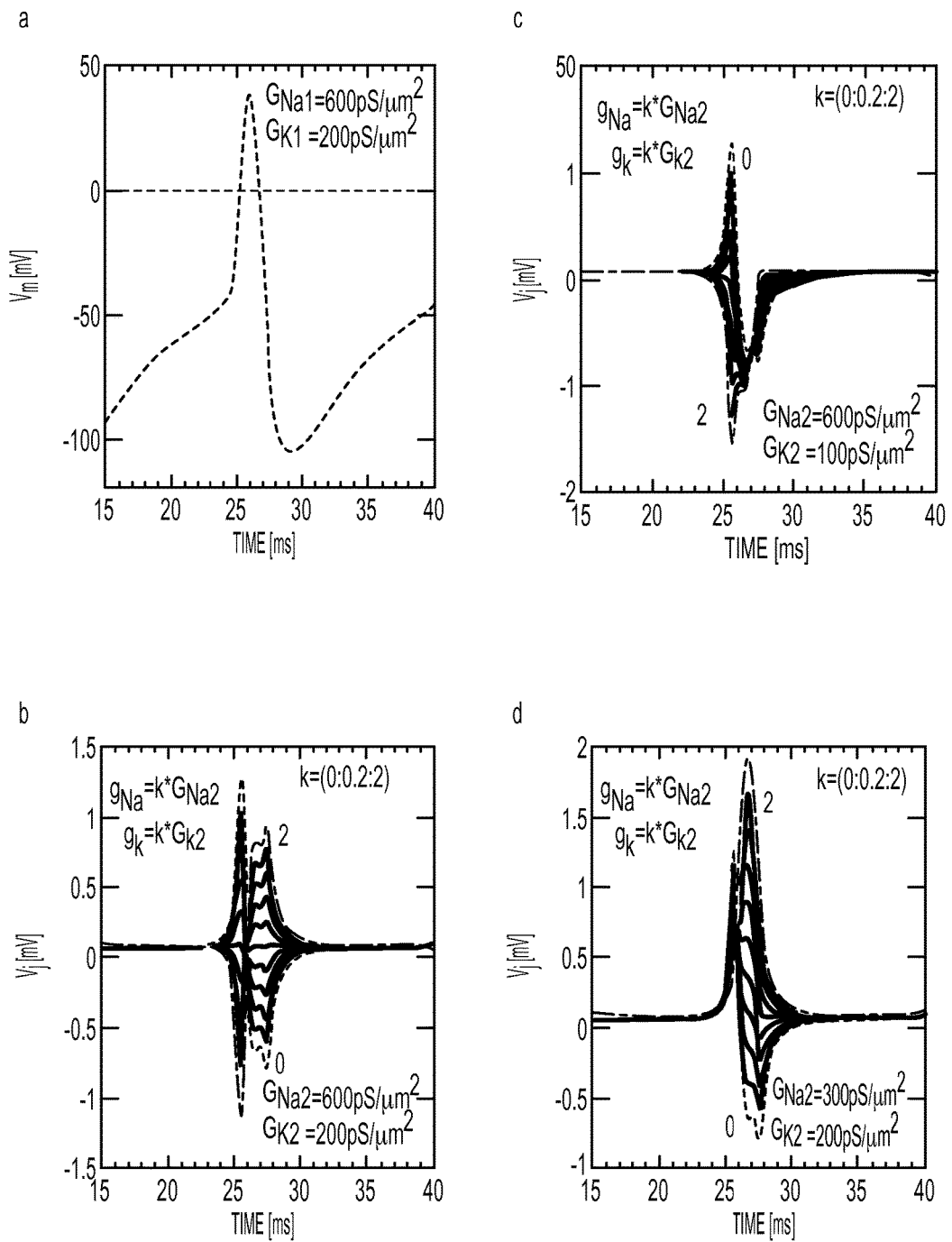

FIG. 30 shows (a) a typical intracellular membrane voltage when an AP is elicited. (b) Effect of raising the overall junction conductance with respect to the free membrane conductance. Notice, that when conductance values for both Na+ and K+ are simultaneously raised in the junction, the extracellular waveforms shift from biphasic to inverted capacitive. (c) Similar operation to (b) with the K+ conductance in the junction decreased with respect to the free membrane. When the Na+ and K+ conductance in the junction is now raised, the Na+ activity becomes much larger than the K+ activity. This causes a trough in the AP waveform. (d) Similar operation to (c) but with the Na+ conductance decreased in the junction. This causes an intracellular-like waveform although with a diminished amplitude.

DETAILED DESCRIPTION OF THE NON-LIMITING EMBODIMENTS

A. A Floating Gate Based Sensor Apparatus in Accordance with the Embodiments

1. Introduction

Transistor-based biological/chemical transducers have gained considerable attention over the last decade. For example, an ion sensitive field effect transistor (ISFET) has its gate oxide directly exposed to an electrolyte with its electrochemical potential set by a solution reference electrode. The gate oxide interface possesses a net surface charge due to hydroxyl groups upon exposure to the electrolyte. The charge density and the electrostatic potential then decay from the interface into the solution bulk over the characteristic distance of the Debye length. A change in the oxide-electrolyte interface potential due to ionic adsorption or reference-electrode biasing then induces a shift in the channel current via a change in the electric field in the gate oxide. The change in the reference electrode potential with respect to the transistor source bias to achieve a constant channel current (i.e. a constant field in the gate oxide) is thus a direct measure of the oxide-electrolyte interface potential shift. The transistor is typically only sensitive to ionic and molecular charges within a few Debye lengths from the interface. While numerous examples of FET-based ionic and molecular sensors have been demonstrated, the ability to dissect the complex interplay between pH, salinity and surface chemistry is still unclear. In addition, the ability to impart electrical control over the sensing interface concomitantly is still elusive.

Dynamic control of surface charge can potentially realize reversible interfaces, addressable sensor pixels in large-scale arrays, controlled charge modulation, and even local pH titration with simultaneous detection. However, since ISFET generally has an exposed dielectric interface which consists of amphoteric surface groups, a change in electric field within the oxide would not only modulate ions in solution but also affect the chemical composition of the interface.

Similarly, when an electrode covered by an insulator is biased in an electrolytic medium, the field in the insulator would thereby modulate the ionic double layer. The applied potential to such an electrode or static stored charge on a buried floating electrode can in turn influence the insulator's surface charge according to its amphoteric nature, which then affects the proton binding affinity, the adsorption equilibrium and the net charge in the double layer. The interplay between the applied field and the chemical equilibrium at the interface is termed as "electrochemical gating." The first examples of electrochemical gating in microfluidic systems demonstrated that local fields could modulate the electro-osmotic flow in micro-channels, but did not elaborate on the chemical properties of the interface.

2. Theoretical Considerations

Figure 1:
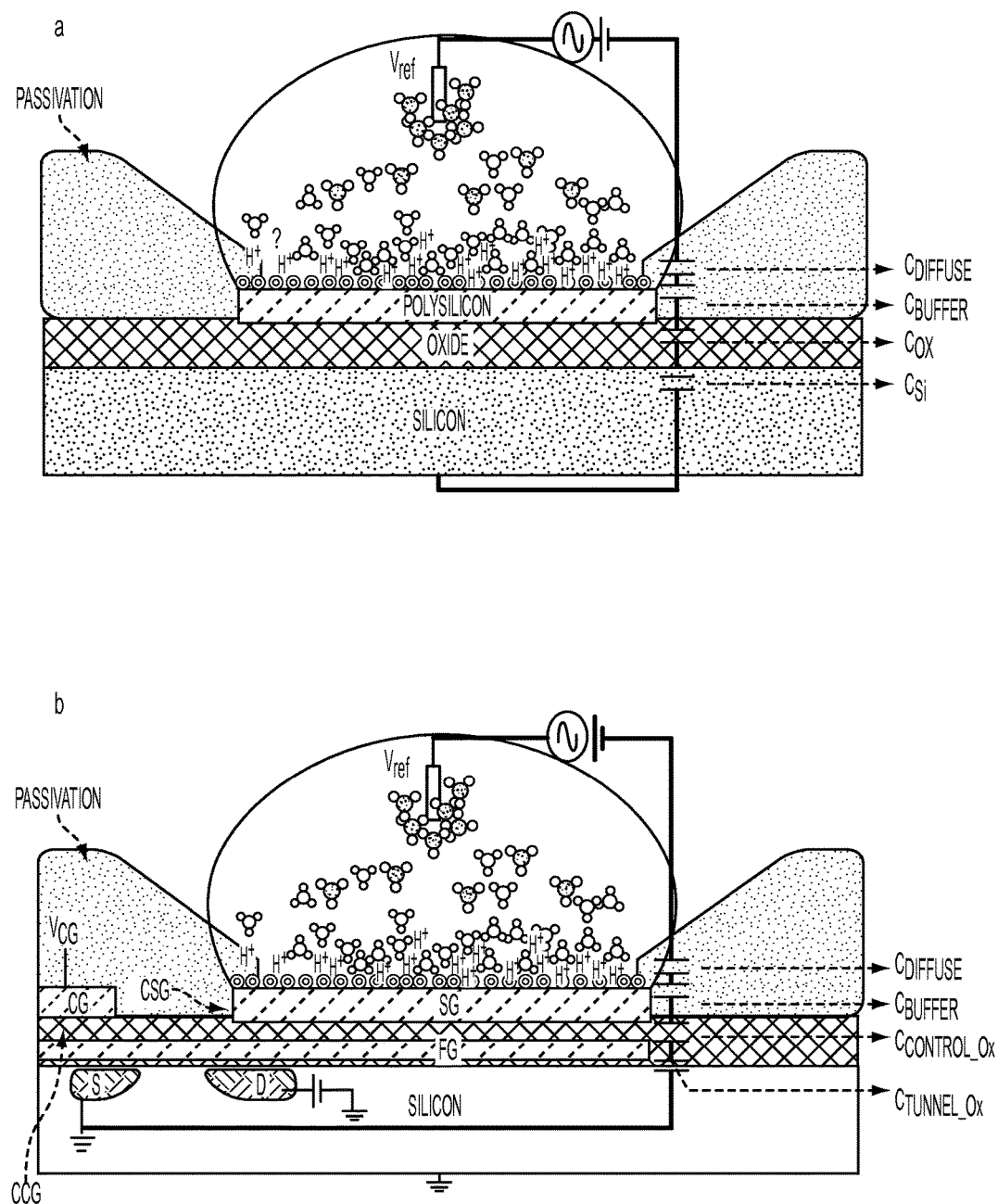
FIG. 1 shows (a) An EOS capacitor used in a CV analysis. (b) A CvMOS transistor resulting from the EOS capacitor with two independently driven gates: (control) CG and (sensing) SG coupled to a common (floating gate) FG. The FG to electrolyte capacitive coupling is mimicked by the EOS structure. The CG is shielded from the solution via a thick oxide (2 μm) passivation. (c) An SEM image of the fabricated transistors showing the SG, CG and transistor regions, respectively.
Figure 1:
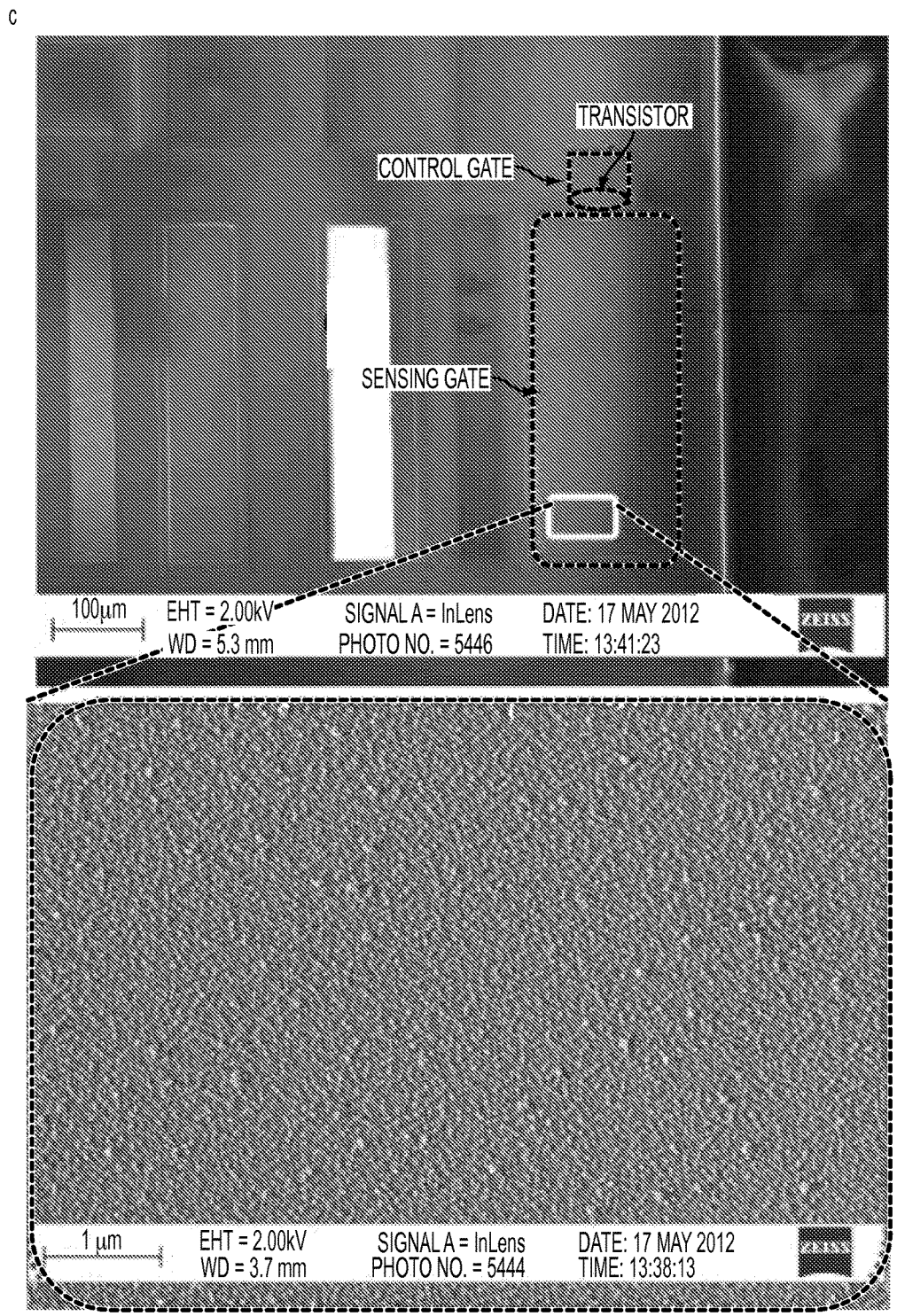
Figure 2:
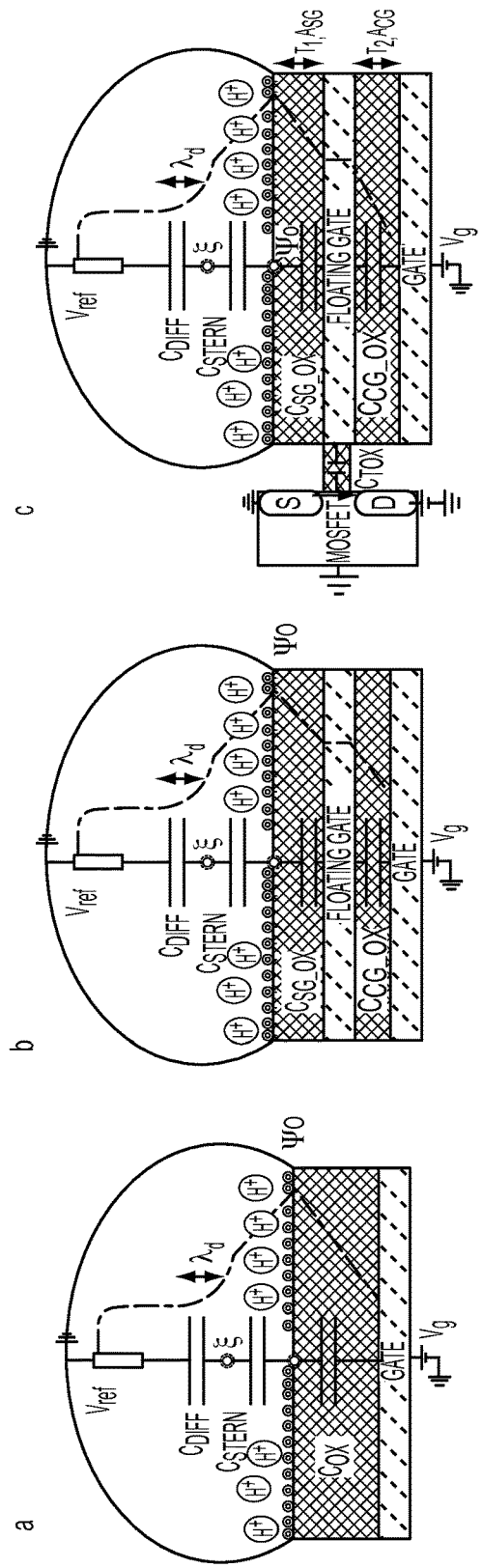
FIG. 2 shows (a) a capacitive model of the EOS structure in accordance with the embodiments. A potential difference between a control gate and the reference electrode disturbs a chemical equilibrium at the oxide elctrolyte interface. (b) Introduction of a floating conductor between the CG and oxide electrolyte interface. $C_{CG\_OX}$ and $C_{SG\_OX}$ are the capacitances between the CG and FG, and between FG and solution interface, respectively. The electrolyte is gated via the field in the underlying oxide set by the FG potential. (c) Capacitive coupling of a transistor to the FG. The CG bias and the difference between $\psi_O - V_{REF}$ REF capacitively set the FG potential via the capacitive divider which modulates the transistor output. The CG is thus a handle to control both the transistor output and $\psi_O - V_{REF}$.

In order to develop an intuitive understanding of the embodied floating gate based sensor apparatus and methodology (i.e., in comparison with ISFET sensor apparatus and methodology), one may first consider a conventional electrolyte-oxide-semiconductor (EOS) structure as illustrated in FIG. 1a and FIG. 2a system, where electrochemical gating modulates the surface charge. AC measurements using capacitive electrode structures are frequently employed to measure the net charge modulation in an electrolyte. However, measuring capacitances on the order of pF to aF in many lab-on-chip (LOC) systems often requires complex circuitry and a long averaging time, and is thus prone to noise. It is much easier to measure charge via transistors at such scales, as the output current can be sampled more easily. If one intentionally introduces a highly conductive slab as a floating gate (FG) as illustrated in FIG. 2b in between the reference electrode and oxide-electrolyte interface, the charge modulation in the electrolyte now depends on the electric field between the FG and electrolyte bulk. The FG potential is determined by the weighted inputs of all capacitors coupled to the FG and additionally the nonvolatile charge it stores. The change in surface charge or ionic charge in the double layer will thus affect the FG potential. The question remains as whether one can measure the FG potential directly to estimate the electrolyte charge. By coupling a transistor capacitively to the FG, the current output is an accurate measure of the FG potential. This transistor concept is termed as the chemoreceptive neuron MOS transistor (CvMOS) as illustrated in FIG. 1b and FIG. 2c, and which forms the basis of the embodiments. In accordance with the embodiments, a sensor apparatus that uses such a CvMOS transistor is designated in accordance with the embodiments as a floating gate based sensor apparatus.

The CvMOS transistor illustrated in FIG. 1b and FIG. 2c is a multi-gate transistor with control (CG) and sensing gates (SG) coupled to FG. The CG alleviates the sole reliance on biasing from the reference electrode $V_{REF}$, which is important from a reliability and pixel-level biasing perspective. The reference electrode (Ag/AgCl) can still be used to pin the electrolyte bulk. This scheme has multiple advantages: (i) suitable fluid biasing can lower the read voltage from the control gate and enlarge the sensing range, (ii) the pinned electrolyte potential results in fast ion settling time, and (iii) the CG can be used in feedback to maintain the optimal signal-to-noise ratio (SNR) condition without changing the reference electrode bias. Due to the possible asymmetric capacitances between the two gates, the voltage measured from the CG to maintain the same channel current can be intrinsically amplified if $C_{CG} < C_{SG}$. At high CG biases, Fowler-Nordheim (FN) tunneling ensues to inject nonvolatile charge onto the FG, which can in turn render a strong field in the SG oxide even after the CG bias is removed. One may experimentally investigate the role of electrolyte composition on the transistor characteristic both with and without FG charges and corroborate the resulting measurements against standard (EOS) capacitors with similar chemically reactive interfaces.

3. Additional Embodiments of Floating Gate Based Sensor Apparatus

Alternate configurations and embodiments of a floating gate based sensor apparatus in accordance with the embodiments are illustrated in FIG. 3a to FIG. 3j.

Figure 3A:
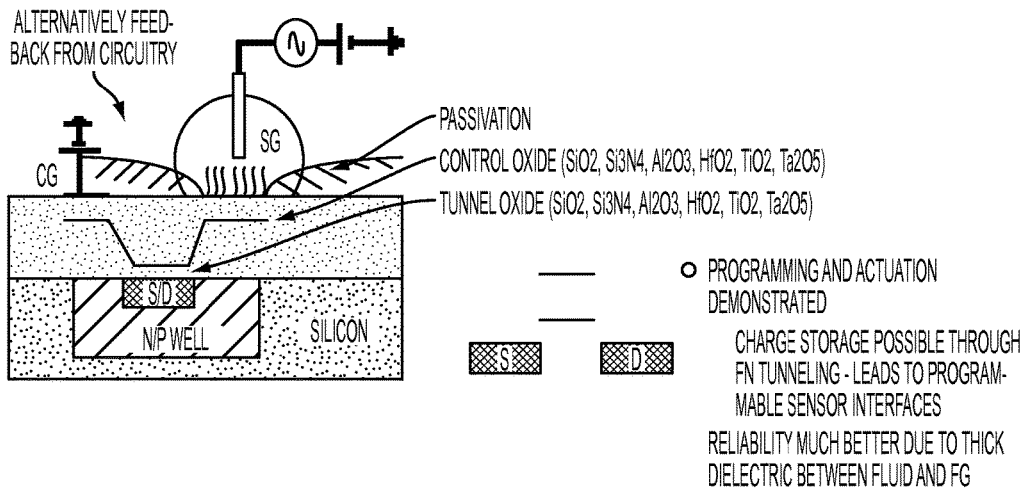
FIG. 3 shows (a)-(e) a series of alternative embodiments of a floating gate based sensor structure in accordance with the embodiments that uses a bulk semiconductor substrate. (f) and (g) show similar floating gate based sensor structures predicated upon a silicon-on-insulator (SOI) substrate. (h), (i) and (j) show similar floating gate based sensor structures predicated upon finFET structures.

In particular, FIG. 3a illustrates within the context of a somewhat different cross-section in comparison with FIG. 1b and FIG. 2c a floating bate based sensor structure that is intended to correspond with the floating gate based sensor structure whose schematic cross-sectional diagram is illustrated in FIG. 1b and FIG. 2c, but with the exception of absence of a separate sensing gate aligned with but separated from a floating gate. Thus, within the floating gate based sensor structure whose schematic cross-sectional diagram is illustrated in FIG. 3a, a solution to be analyzed in the form of a droplet contacts a generally thick intergate dielectric layer (i.e., having a thickness from about 100 to about 1000 nanometers and also referred to as a control dielectric layer), thus allowing for enhanced reliability when analyzing a sample that comprises the droplet.

Figure 3B:
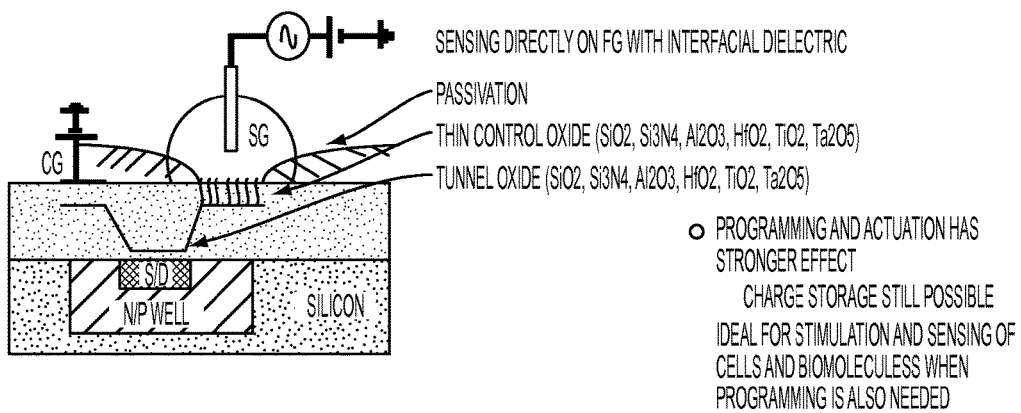

In addition, FIG. 3b illustrates a floating gate based sensor structure similar to the floating gate based sensor structure whose schematic cross-sectional diagram is illustrated in FIG. 3a, but wherein the robust intergate dielectric layer that covers the floating gate and provides the sensing surface is intended to be replaced with a thinner intergate interfacial dielectric layer (i.e., having a thickness from about 10 to about 100 nanometers and also referred to as a control dielectric layer), which in turn allows for stimulation and sensing of cells when programming (i.e., manipulation) is also needed.

Figure 3C:
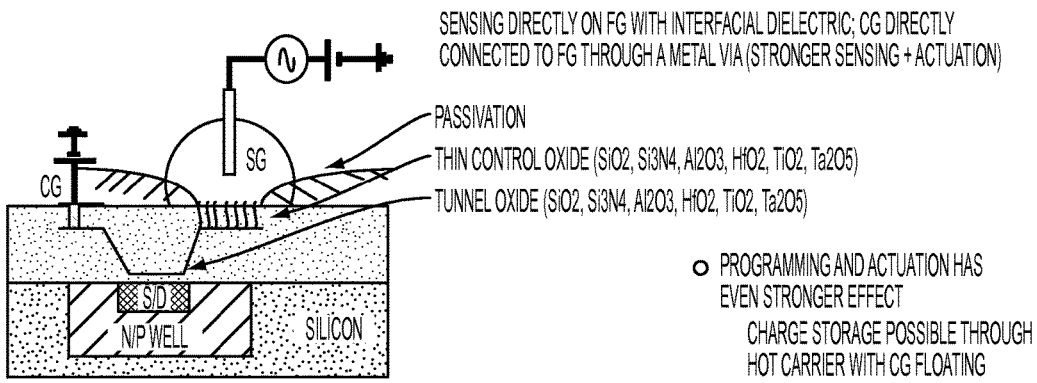

Further, FIG. 3c illustrates a floating gate based sensor structure similar to the floating gate based sensor structure whose schematic cross-sectional diagram is illustrated in FIG. 3b, but wherein the floating gate based sensor structure also provides for a direct electrical connection between a control gate and a floating gate. Such a direct electrical connection between the control gate and the floating gate provides for stronger actuation of a floating gate based sensor apparatus in accordance with the embodiments.

Figure 3D:
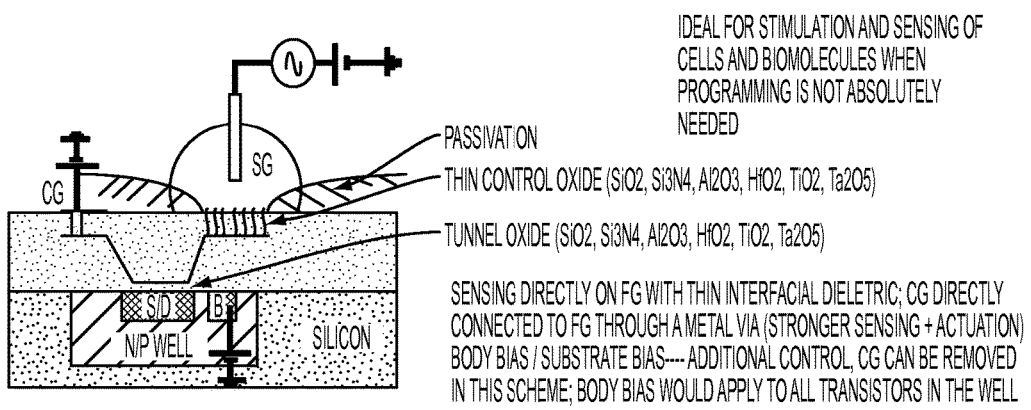

Still further FIG. 3d illustrates a floating gate based sensor structure similar to the floating gate based sensor structure whose schematic cross-sectional diagram is illustrated in FIG. 3c, but which now includes a body bias which allows for elimination of the control gate, or at minimum reconfiguration of the control gate. As is illustrated within the schematic cross-sectional diagram of FIG. 3d, the body bias comprises a doped region of appropriate (i.e., opposite) polarity and a dopant concentration from about 1e18 to about 1e20 dopant atoms per cubic centimeter within the transistor well having the opposite dopant concentration from about 1e16 to about 1e18 dopant atoms per cubic centimeter.

Figure 3E:
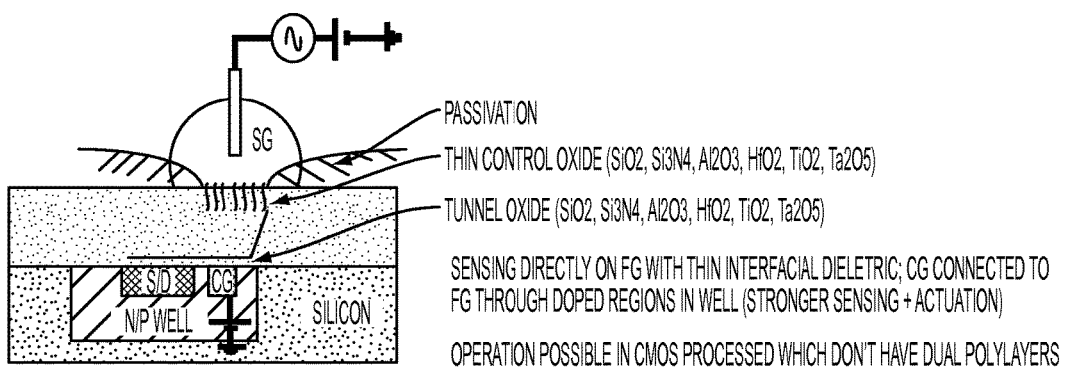
Figure 3F:
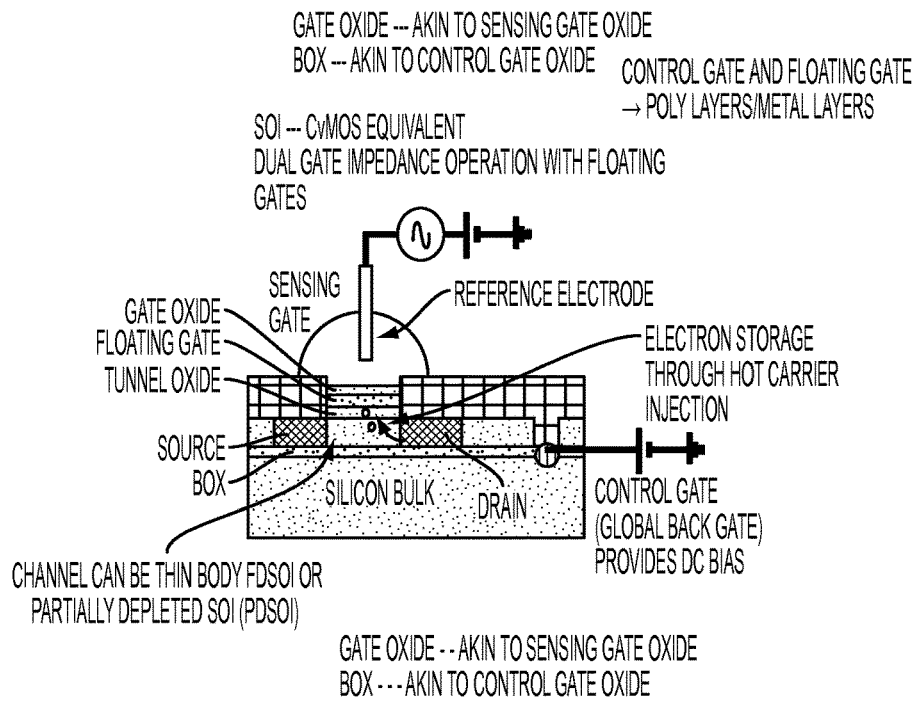
Figure 3G:
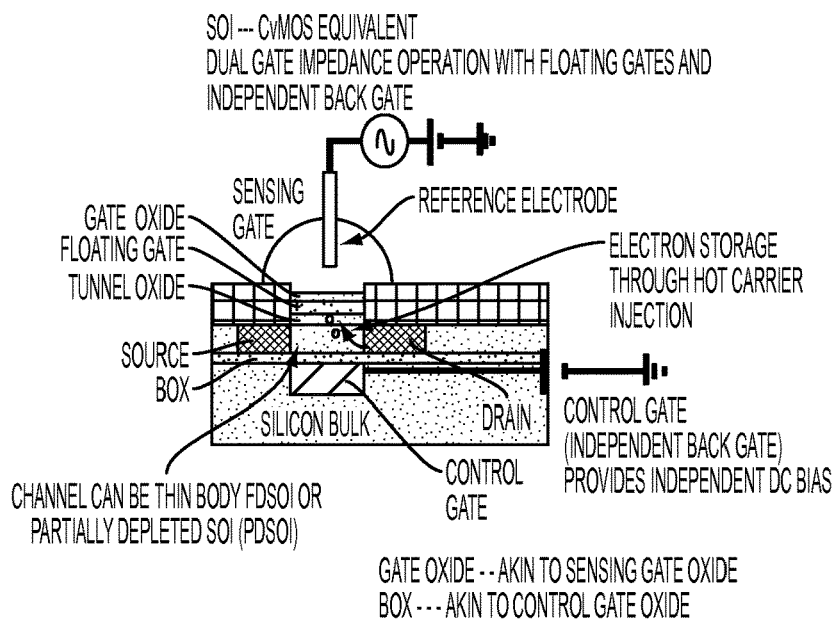

Finally FIG. 3e illustrates a floating gate based sensor structure similar to the floating gate based sensor structure whose schematic cross-sectional diagram is illustrated in FIG. 3d, but which now is absent the control gate and uses the body bias in conjunction with the reference electrode for separating and manipulating a bio-macromolecule within a sample.

Thus as illustrated within the schematic cross-sectional diagrams of FIG. 1a/b, FIG. 2a/b/c and FIG. 3a/b/c/d/e embodiments of a floating gate based sensor structure may use as a sensing surface either a dielectric layer thin film or a dielectric layer thicker film located and formed upon a conductor material layer sensor surface which is typically a doped polysilicon layer surface. Alternatively the sensing surface in accordance with the embodiments may comprise an exposed conductor or semiconductor material surface which may be, but is not necessarily limited to, a doped polysilicon surface having a dopant concentration of about 1e20 to about 1e22 dopant atoms per cubic centimeter.

As is also illustrated within the foregoing cross-sectional schematic diagrams, the embodiments also contemplate control gate electrical bias and body bias with respect to a floating gate as a sensor surface. The embodiments also contemplate control gate and reference electrode bias of a floating gate more generally, although the embodiments also consider other arrangements for at least two bias component bias of a floating gate within a floating gate based sensor apparatus in accordance with the embodiments.

Within any of the foregoing embodiments as illustrated within any of the foregoing schematic cross-sectional diagrams FIG. 1a-b, FIG. 2a-c and FIG. 3a-j, a sensing surface of a sensing electrode has dimensions from about 1,000 to about 50,000 square nanometers.

As is understood by a person skilled in the art, while the foregoing embodiments are illustrated within the context of nominally a bulk semiconductor substrate as a base substrate within a floating gate based sensor apparatus in accordance with the embodiments, the embodiments are not intended to be so limited. Rather the embodiments are also intended to include semiconductor substrates such as but not limited to bulk semiconductor substrates and semiconductor-on-insulator (SOI) semiconductor substrates. In particular, a floating gate based sensor apparatus in accordance with the embodiments fabricated using a SOI substrate in accordance with the schematic cross-sectional diagrams of FIG. 3f and FIG. 3g will allow for consideration of fully depleted transistor channels in addition to partially depleted transistor channels which are common with bulk semiconductor substrates.

Figure 3H:
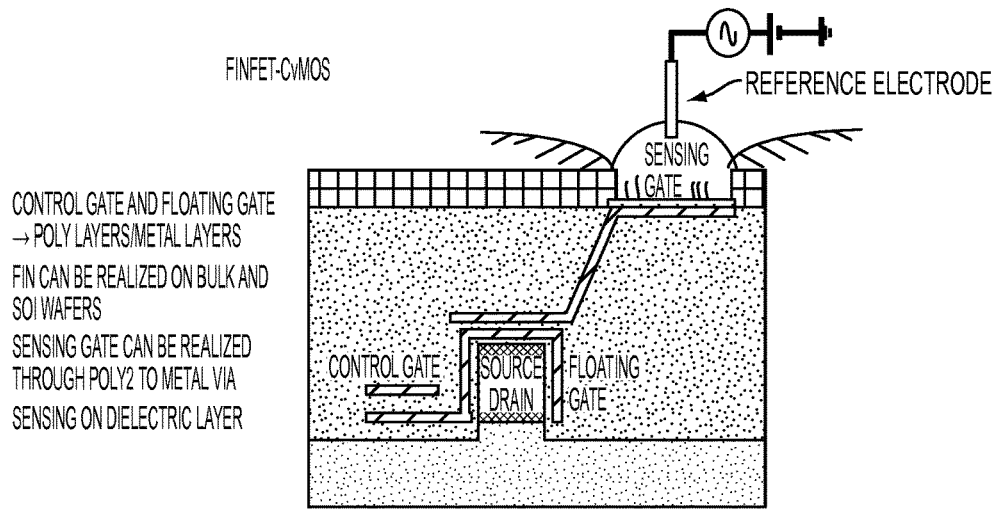
Figure 3I:
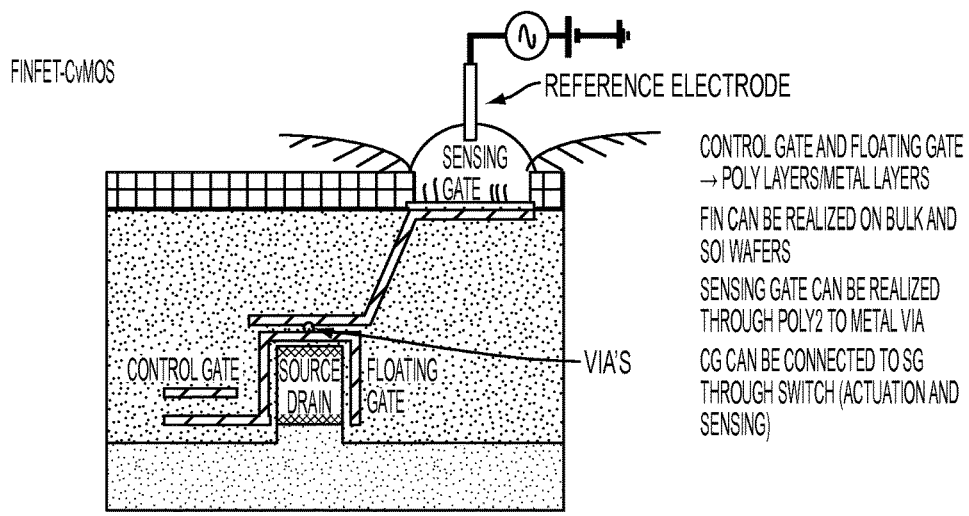
Figure 3J:
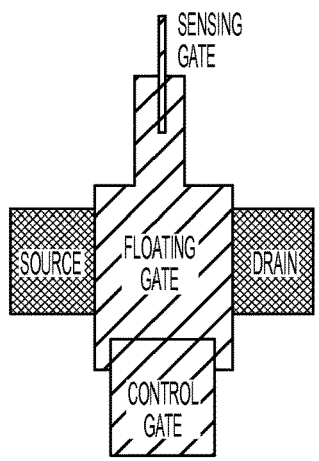
Figure 5:
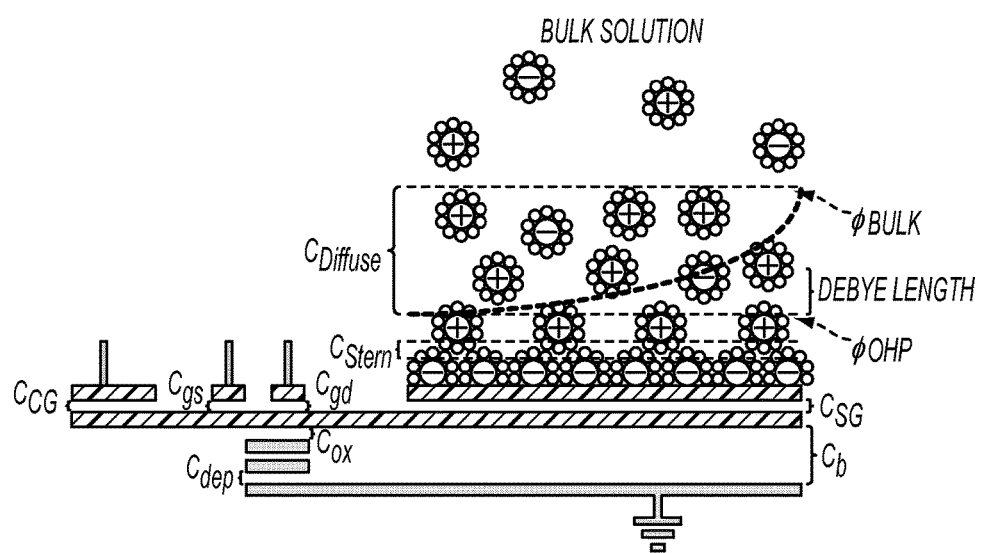
FIG. 5 shows a capacitive model with various capacitance inputs. and $C_{SG}$ are the control and sensing gate capacicance, respectively. The double layer capacitances are depicted as the Stern and diffusive componenets, respectively. Beyond the Debye length, the charge on the adsorbed molecule is effectively screened. Here $\phi_{OHP}$ represents the outer helmholtz potential commonly termed ξ potential i.e., the potential at the slip plane.

Similarly, as is also understood by a person skilled in the art, while the foregoing embodiments are illustrated within the context of conventional planar metal oxide semiconductor field effect transistor structures for CG actuation, the embodiments are as well also not intended to be so limited. Rather the embodiments may utilize semiconductor transistor structures including but not limited to conventional planar semiconductor transistor structures and more advanced finFET three dimensional semiconductor transistor structures for CG actuation. In particular, finFET three dimensional transistor structures as are illustrated in FIG. 3h, FIG. 3i and FIG. 3j provide for enhanced sensitivity incident to CG actuation.

In summary, the embodiments provide for at least two separate bias component (i.e., bias sources) biasing of a floating gate based sensor surface within a floating gate based sensor apparatus. With such a configuration, for example, AC and DC signals can be applied simultaneously and independently to the floating gate based sensor surface within the floating gate based sensor structure. This feature allows for an impedance using split AC/DC signal delivery. As well, and as will be illustrated within the context of applications of the apparatus as discussed in further detail below, the floating gate based sensor apparatus in accordance with the embodiments may be used for the detection and manipulation of a broad range of biomaterials.

Moreover, floating gate based sensor structures and floating gate based sensor apparatus in accordance with the embodiments may be fabricated using semiconductor device fabrication technology that is otherwise generally conventional. Finally, additional details of related floating gate based sensor structures and floating gate based sensor apparatus in accordance with the embodiments is also taught within U.S. Pat. Nos. 7,053,439 and 7,960,776, the contents of which are incorporated herein fully by reference.

4. Experimental Considerations a. Materials

EOS capacitors in accordance with FIG. 1a were fabricated on p-type silicon wafers after standard MOS cleaning. About 20 nm of thermal $SiO_2$ was grown, followed by 30 nm growth and patterning of LPCVD polysilicon with $n^+$ doping. Atomic-layer deposition (ALD) of nitride as a protective coating was then deposited and patterned to expose only the polysilicon gate to solution. The floating gate based transistors were fabricated in a 1.5 μm AMI foundry process as may be otherwise generally conventional. Briefly, the tunnel oxide refers to the oxide between the channel and the FG, while the control oxides represent the oxide between the CG/SG and FG. The FG is electrically floating and does not have any direct conducting path to the electrolyte or other electrodes. The reference electrode pins the electrolyte bulk to ($V_{REF}$) while the CG can be pulsed to program or erase the device. The tunnel and control oxide thicknesses are 10 nm and 35 nm, respectively. The control gate area is 25 μm×40 μm while sensing gates vary between 5 μm×400 μm and 200 μm×400 μm. An SEM image of the fabricated chip is shown in FIG. 1c. The chip was cleaned with DI water and isopropyl-alcohol (IPA) before each test. A small reservoir made of epoxy was created to isolate the fluid from the bond pads.

Electrolytes containing NaCl, $MgCl_2$ and $Co(NH_3)_6Cl_3$ salts (Sigma Aldrich) were made up to the desired dilution using Millipore de-ionized $H_2O$. The pH of the solutions was regulated using conjugate acid-base mixtures. TE buffer (10 mM TRIS pH 8, 10 mM NaCl and 1 mM EDTA) was added to test for buffering effects. Electrodes made of Ag/AgCl were used as reference electrodes. Experiments were performed in a light-tight environment.

b. Electrical Instrumentation

Capacitance-voltage (CV) measurements were performed using a Keithley 4200 semiconductor parameter analyzer. CV profiles were recorded at various small-signal frequencies. The reference electrode was supplied with an AC signal superimposed on a slow DC sweep, while the wafer chuck was used as ground. The transistor transfer characteristics (the drain current $I_D$ vs. the CG bias ($V_{CG}$)) were recorded using a Keithley 236 source measure unit (SMU) for the drain ($V_D$=1V) and a Keithley 2400 was used to sweep $V_{CG}$. Programming was carried out by applying a large positive voltage to $V_{CG}$ with a +1V bias on $V_D$ unless otherwise specified, while erasing was by a large-magnitude negative voltage. The transient measurements at constant $V_{CG}$ were recorded by the trans-impedance amplifier (TIA, Stanford Research Systems SR570, CA, USA) with a sensitivity of $$100 \frac{\mu A}{V}$$

and low-pass filtering at 3 KHz. The data was collected on a computer through a data acquisition test board (NI BNC 2110 and NI USB 6259). The bias on the TIA was set to 1V. Prior to measurements, the transconductance ($g_m$) seen from both the CG and SG was recorded in order to calibrate the capacitance ratio.

5. Device Operation and Sensing Principles a. General

The floating gate based sensor apparatus works on the principle of the conventional neuron MOS transistor where two input gates are coupled to a common FG. The potential on the FG ($V_{FG}$) can be calculated by the capacitive divider model shown in FIG. 7. Additionally, a net charge Q can be stored on FG via tunneling. The constant current readout implies that $V_{FG}$ is brought back to the same point. This can be achieved via $V_{CG}$ or $V_{REF}$. The capacitance ratio between the SG and CG to the FG $$\left( \frac{C_{SG}}{C_{CG}} \right)$$

sets the scaling factor. Thus an asymmetric CvMOS structure can lead to a magnification of the threshold voltage shift (Eq. 1) as observed from the control gate when the sensing gate experiences a load from the electrolyte.

$$\Delta V_{th\_CG} = \frac{C_{SG}}{C_{CG}} \cdot (\Delta \psi_O) \quad (1)$$

The governing equations are listed in FIG. 4. Recent reports have proposed similar concepts and claimed to have beaten the Nernst sensitivity limit of 59 mV/pH. We reiterate that this technique merely scales the surface potential shift and does not signify any change in the intrinsic properties of the electrolyte interface. The amplification method does however reduce the burden on supporting circuitry to sense the voltage shift. Theoretically, the capacitive amplification factors should have achieved values between 70~90 for the layouts used in this study. However, due to parasitics we experimentally observed factors of 10~30 see, e.g., FIG. 6a.

b. Programming and Erase Operations

In conventional Flash memory devices when the CG bias is swept to a large magnitude, sufficient electric field can develop across the gate stack enabling electron/hole tunneling from the silicon channel onto the FG ($Q_{FG}$). "Programming" is the condition when the FG has a net stored charge state, while "erase" is the condition under which that charge is removed, see FIG. 7. The field in the oxide during tunneling is quite high $$\left(0.8 \sim 1 \frac{V}{nm}\right)$$

which is a pre-requisite for Fowler-Nordheim (FN) tunneling. Such fields are quite common in Flash memory devices and can be employed many times without permanent breakdown. The floating gate based sensor apparatus has an EOT (effective oxide thickness) of approximately 50 nm and the maximum CG bias for programming does not exceed 40V.

The CG is shielded from the solution by a large passivation oxide (>2 μm) and hence the CG bias has no direct influence on the electrolyte except through the FG and SG coupling. The SG surface is highly-doped polysilicon which is widely being considered for biosensing applications. At high $V_{CG}$, the electric field in the CG control oxide ($E_{CG\_OX}$) increases. Normally $V_{FG}$ would rise together with $V_{CG}$. However the FG is coupled to $V_{REF}$ through the large SG which ensures that $V_{FG}$ does not increase much with an increase in $V_{CG}$. This directly affects $E_{CG\_OX}$ as it rises considerably higher than the field in the tunnel oxide ($E_{TOX}$).

Figure 7:
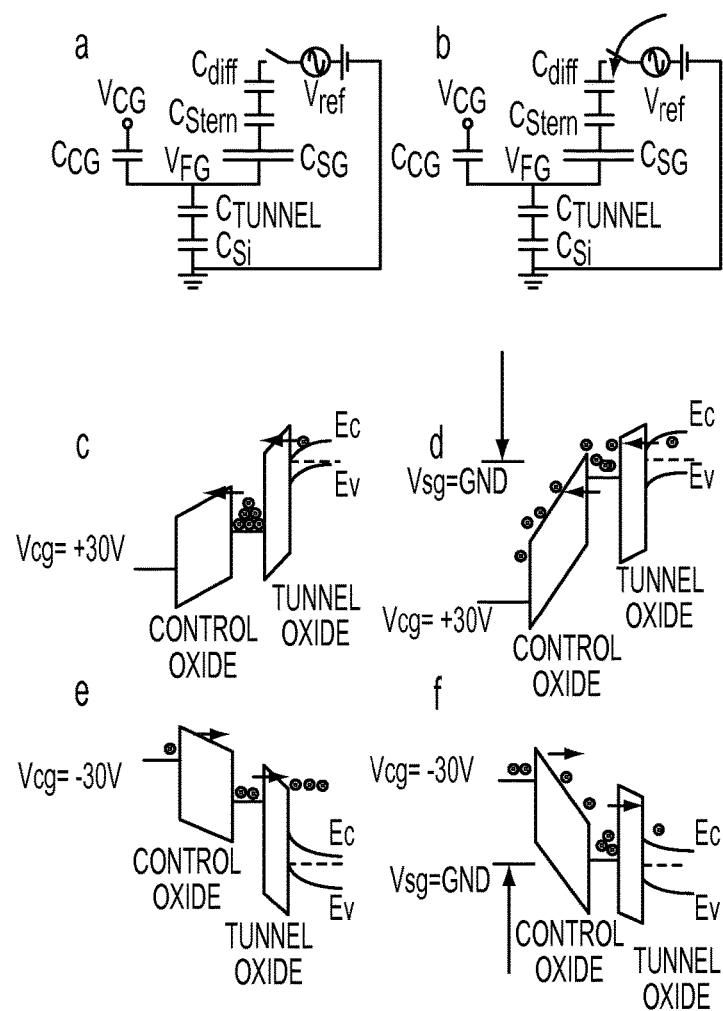
FIG. 7 shows (a) a capacitive network of the floating gate based sensor structure with $V_{REF}$ open circuited and (b) $V_{REF}$ grounded. (c) Band diagram with $V_{REF}$ open circuited and a +30V application on the CG depicts electron injection into the FG. Notice how the FG potential tracks the CG bias (d) Band diagram with $V_{REF}$ at ground and a +30V CG bias results in large electron out tunneling which results in hole storage on the FG. The FG potential is strongly pinned by the reference electrode bias (e) same condition as (c) with a −30V CG bias. This creates hole storage on the FG. (f) Same condition as (d) with a −30V CG bias, this results in electron injection from the CG into the FG.

For example, given a capacitive ratio of 20, a 40V CG bias induces only a ~2V rise in $V_{FG}$. Evidently this would cause a larger change in $E_{CG\_OX}$ than in $E_{TOX}$. Electrons thus tunnel out of the FG onto the CG faster than they tunnel onto the FG from the channel. This causes a net positive stored charge on the FG and lowers the threshold voltage $V_{th}$. However, if $V_{CG}$ is large and negative, the opposite occurs resulting in net electron storage. The energy band diagrams depicting this operation are shown in FIG. 7.

If the reference electrode is left floating, the capacitive coupling in the SG branch is much weaker and $V_{FG}$ is then allowed to track $V_{CG}$. The E-field in this case aids electron injection from the channel into the FG during programming and hole storage during erase FIG. 7c and FIG. 7e, similar to conventional Flash memory operation.

Figure 6:
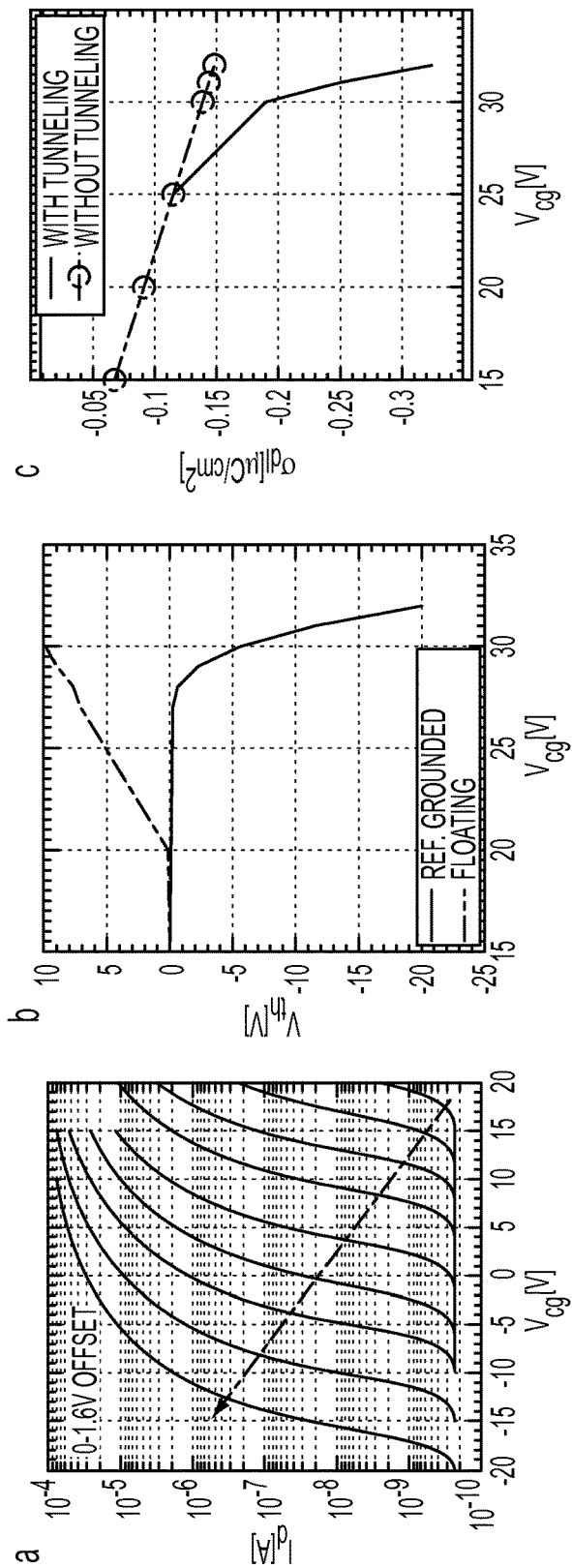
FIG. 6 shows (a) typical capacitive amplification ratio experimentally extracted by modulating the electrolyte and probing the channel current via $V_{CG}$. The extracted ratio above has an amplification factor of ~20. (b) Simulation of the tunneling characteristic showing the difference between $V_{REF}$ being pinned and floating. Pinning $V_{REF}$ results in hole storage on the FG while floating $V_{REF}$ results in electron storage when the CG is pulsed. (c) Change in electrolyte charge when $V_{CG}$ is pulsed shows that tunneling serves as a boost to twice the charge modulation in comparison with pure capacitive charging.

Thus by flipping the reference electrode between floating and biasing conditions during the programming process, the polarity of stored charge on the floating node can be significantly changed. This nonvolatile charge then capacitively interacts with the fluid via the field effect. A simulation of the tunneling effect with and without the reference electrode is shown in FIG. 6b. Electrostatics of the system is represented by the capacitors $C_{DL}$ (double layer), $C_{SG}$ (sensing gate), $C_{CG}$ (control gate) and $C_{tunnel}$ (tunnel oxide), respectively. This network is solved self-consistently with a Tsu-Esaki tunneling formulation which is represented by voltage-controlled current sources.

The SG-fluid interface is considered to be in steady state during the program pulse and $V_{th}$ measurement ramp. Dynamic processes of ion or water dipole rearrangement are assumed to occur at time scales much faster than tunneling. The double layer capacitance ($C_{DL}$) is modeled based on a Poisson-Boltzmann formulation including ion Steric effects.

6. Role of Surface Groups and Electrochemical Gating

The ISFET or EOS response is generally dictated by the protonation behavior of the interfacial inorganic oxide in direct contact with the electrolyte. Surface hydroxyl groups are amphoteric in nature, protonated or deprotonated depending on the solution bulk pH ($pH_B$), resulting in a net surface charge $\sigma_O$. It is this shift in charge that determines the net $pH_B$ sensitivity of the underlying transistor. It has been theoretically demonstrated that in addition to $pH_B$, the field in the underlying oxide profoundly affected $\sigma_O$, which further influenced the surface pH sensitivity ($pH_S$). One may adopt a hydroxyl surface group model where the basic acid-base equilibrium at the interface is given by Eq. (2).

$$A - OH \overset{K_a}{\rightleftharpoons} A - O^- + H_B^+ \qquad (2)$$

$$A - OH + H_B^+ \overset{K_b}{\rightleftharpoons} A - OH_2^+$$

Here $K_a$ and $K_b$ are the dissociation constants and $H_B^+$ is the bulk proton concentration. At a particular $pH_B$, the interface is charge neutral. This is termed as $pH_{PZC}$, i.e., the pH at the point of zero surface charge. However, when $pH_B$ is not equal to $pH_{PZC}$, the surface pH ($pH_S$) shifts in response to the change in $pH_B$. The number of surface groups that ionize in response to varying $pH_S$ is termed as the buffer capacity ($\beta_S$) and its associated capacitance is termed as $C_{Buffer}$. By definition, $\beta_S$ is the ratio of the change in net surface charge to that in $pH_S$.

$$\beta_S = \frac{d[\sigma_O]}{dpH_S} \qquad (3)$$

Here $\sigma_O$ is equal to the net number of titrated groups per area:

$$\sigma_O = -e \cdot \Gamma^{O-} + e \cdot \Gamma^{OH_2^+} \qquad (4)$$

where $N_S = \Gamma^O = \Gamma^{O-} + \Gamma^{OH_2^+} + \Gamma^{OH}$ is the total number density of ionizable surface groups and is a constant for a given surface depending on the chemical composition and surface functionalization. Using the relationship between $$K_a = \frac{H_S^+ \cdot \Gamma^{O-}}{\Gamma^{OH}},$$

$$K_b = \frac{H_S^+ \cdot \Gamma^{OH}}{\Gamma^{OH_2^+}}$$

and $\Gamma^O$, and under the assumption of a single pK model (i.e. $pK_a = -\log_{10}(K_a)$), i.e., when only one type of surface group of $O^-$ is considered, Eq. (4) can be rewritten as, $$\sigma_O = \frac{-e \cdot \Gamma^O}{1 + \frac{H_S^+}{K_a}} \qquad (5)$$

If we consider both surface ionization reactions i.e., a 2pK site-binding model, Eq. (4) then becomes $$\sigma_O = e \cdot \Gamma^{OH} \cdot \left(\frac{H_S^+}{K_b} - \frac{K_a}{H_S^+}\right) \qquad (6)$$

We can then solve for $\Gamma^{OH}$ by using the relationship between $K_a$, $K_b$ and $\Gamma^O$. Here the surface proton activity $H_S^+$ is related to the bulk proton activity $H_B^+$ by the Boltzmann relation $$H_S^+ = H_B^+ \cdot \exp\left(-\frac{e(\psi_O - V_{REF})}{kT}\right) \quad (7)$$

The simulation considers a metal electrode below an insulator exposed to the electrolyte (metal-oxide-electrolyte) as illustrated in FIG. 1a similar to the model structure considered. The electrolyte bulk potential ($V_{REF}$) is held at ground. On applying a potential sweep to the metallic electrode with respect to $V_{REF}$, two compensating charges at the electrolyte-oxide interface will respond: 1) protonation/deprotonation of the surface hydroxyl groups, denoted by $\sigma_O$ and 2) the double layer charge, $\sigma_{DL}$ (see next section). The field in the oxide is then given by $$E_{OX} = \frac{-[\sigma_O + \sigma_{DL}]}{\varepsilon_{OX}} \quad (8)$$

Equation (8) is then solved self consistently for the entire electrostatic system.

7. Electrical Double Layer Charge ($\sigma_{DL}$)

The SG-electrolyte interface is commonly described by the Gouy-Chapman-Stern (GCS) model which considers ions as point charges. When a solid interface is exposed to electrolyte, ionization or ion adsorption creates a net surface charge density $\sigma_O$. This results in a strong attraction of counterions towards the interface to neutralize the immobile surface charge denoted by $\sigma_{DL}$. Co-ions on the contrary are repelled away from the wall. The capacitance at the wall is generally described by a Stern capacitance $C_{Stern}$ from the inner immobile or specifically adsorbed layer and the outer diffuse layer capacitance $C_{DL}$. A value of $$18\frac{\mu F}{cm^2}$$

is assumed for the Stern layer capacitance (i.e. considering an approximate thickness of 5 Å and a dielectric constant of 10). The charge distribution is traditionally described by the Poisson-Boltzmann (PB) equation:

$$\varepsilon\frac{\partial^2 \psi}{\partial x^2} = -2zen_O \sinh\frac{(ze\psi)}{kT} \quad (9)$$

For a z:z electrolyte, where the mobile diffusive charge is confined to a thin capacitor with a width governed by the Debye length.

$$\lambda_D = \sqrt{\frac{\varepsilon kT}{2z^2e^2n_O}} \quad (10)$$

Here z is the valency, $n_O$ the bulk ion concentration, e the elementary charge, kT is the thermal energy and $\varepsilon$ is the dielectric constant of the solvent. Equation (9) stems from a mean-field formulation where ions are treated as point charges, i.e., ion-ion and ion-wall interactions are ignored. In the conventional PB formalism, charge density generally blows up due to the exponential dependence on surface potentials which is unrealistic under moderate to high $\psi_O$ values. By accounting for close packing of ions at the interface, a limit is imposed on the maximum achievable charge density. In this work we model the NaCl system alone using the PB approximation since the effect of size was found to be negligible within the range of $\psi_O$ obtained. However when dealing with multivalent ions the ion distribution from the interface is described using a 1:z approximation including Steric effects (see FIG. 8). One may find that steric effects become prominent when considering large multivalent ions as layering and charge density saturation occurs for surface potentials $$\sim 4-6\frac{kT}{e}$$

Figure 8:
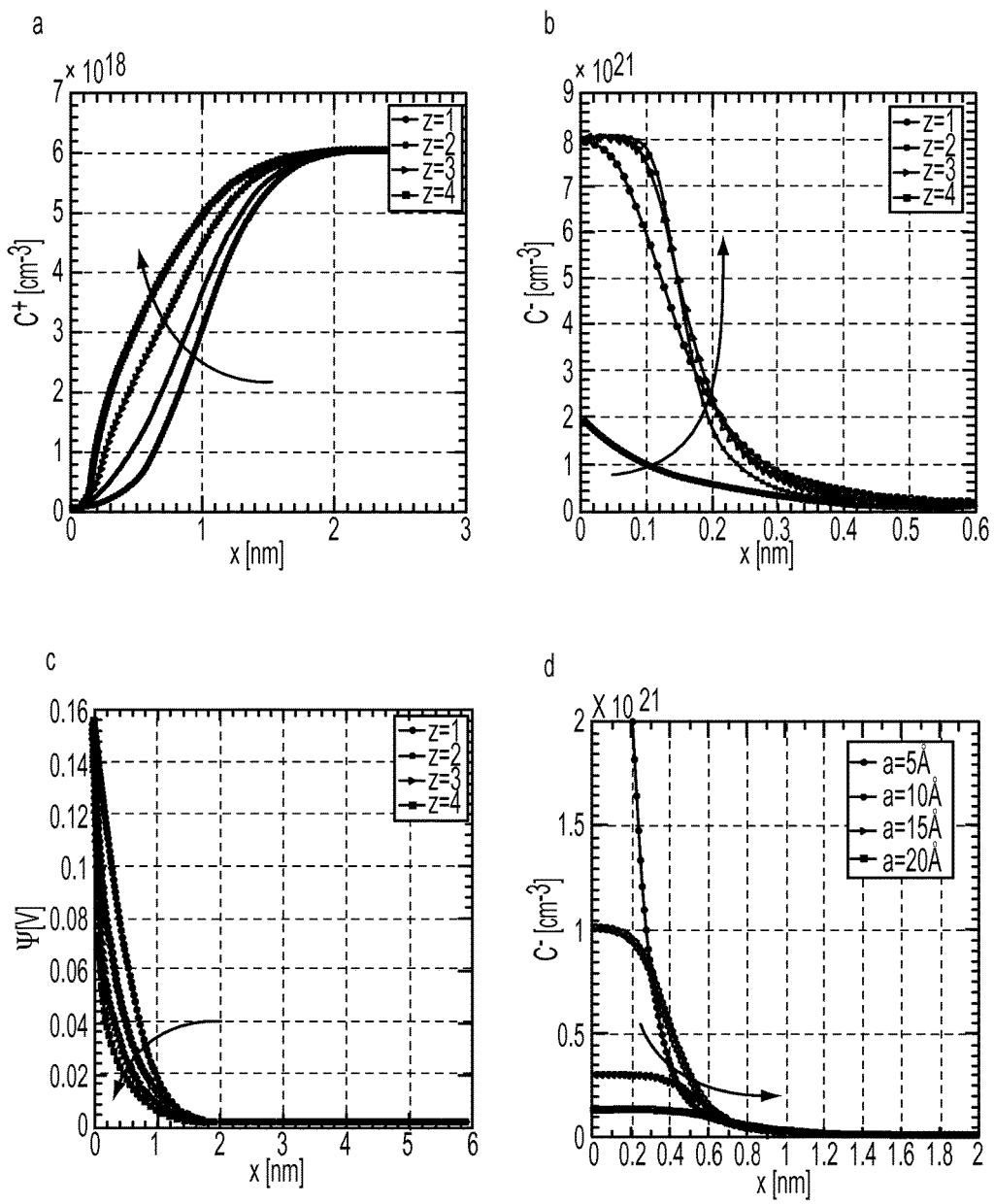
FIG. 8 shows (a) co-ion and (b) counter ion density profiles for varying anionic valency as a function of distance from an electrode interface to an applied $\psi_O$ of 150 mV in a 1:z electrolyte.

(see FIG. 8).

Steric related phenomena are generally weak under low monovalent (NaCl) electrolyte concentrations and moderate $\sigma_O$ conditions. Using the modeling framework presented in the previous section ion size effects were only marginally observed at E-fields above $$\sim 0.5\frac{V}{nm}$$

(not shown) with NaCl salts. One may note that in a recent theoretical study surface charge densities approaching $$\sim 0.2\frac{C}{m^2}$$

(which is typical of pristine dielectric interfaces) significant ion layering may be observed even at low saline concentrations. It is thus paramount to understand the interfacial charge conditions as ion size effects can preclude a proper assessment of the observed signals with sensitive field effect devices. To accurately model ionic layering especially with multivalent salts, one may invoke the modified Poisson-Boltzmann (MPB) theory see Eq. (11)] which includes the hard-sphere Steric effect between ions owing to their finite size but ignores correlations. A Stern layer capacitance is not assumed in the MPB formulation.

$$\varepsilon\nabla^2\psi = -2zen_\infty\frac{\sinh\left(\frac{ze\psi}{k_BT}\right)}{1 + 2v\sinh^2\left(\frac{ze\psi}{2k_BT}\right)} \quad (11)$$

where $v=2a^3n_O$ is the volume packing factor of ions and a is the size of the ion. The packing factor sets a limit on the maximum achievable charge density at the interface. The charge within the double layer is then given by $$q_{MPB} = \sigma_{DL} = -\text{sgn}(\psi_{DL})2zen_O\lambda_D\sqrt{\frac{2}{v}\ln\left(1 + 2v\sinh^2\left(\frac{ze\psi_{DL}}{2kT}\right)\right)} \quad (12)$$

The electric field originating from the potential across the solid/electrolyte interface $$\left(\psi_o \geq \frac{kT}{e}\right)$$

attracts counterions to the surface forming an initial screening layer. If the surface potential rises further $$\left(\sim 5\frac{kT}{e}\right),$$

the electric field strength becomes high enough to cause layering of counterions against the solid interface (see FIG. 8), leading to an effective increase in the double layer thickness, which extends further into the electrolyte bulk. From the capacitive point of view if one were to assume an additional Stern layer, $C_{Stern}$ could help relieve the excess condensation of ions, but would not be able to withstand a large voltage drop $$\sim 5 - 10\frac{kT}{e}$$

due to the Steric constraint. Under such field conditions, the region of ion accumulation extends away from the surface into the solution where ions do not exhibit specific interactions with the solid interface. This causes a further increase in the thickness of the double layer, leading to a decrease in the differential capacitance of the diffusive layer. As mentioned previously this effect becomes significant with large multivalent ions.

8. Multivalent Ions and Charge Inversion

The Debye-Huckel (DH) approximation within the GCS double-layer framework states that the ionic screening effectively lowers the molecular charge in the electrolyte as observed from a finite distance. This is the net charge looking into the Gaussian sphere around the molecule including its screening counter-ion cloud. In comparison with monovalent ions, multivalent ions are known to form a strongly correlated interface with charged moieties which overcharge the interface. This can lead to excess counter ion condensation and eventually polarity reversal, which cannot be explained by the conventional mean-field theory. This counter-intuitive phenomenon is termed as charge inversion (CI). It is postulated that this effect arose primarily due to strong lateral ion-ion interactions which got stronger as the valency increased, and a much larger negative electrochemical potential is developed within the 2D ionic layer. Ion-Ion correlations give rise to counter ion layering against the interface, which can lead to overcharging under suitable field conditions. This is often much easier to achieve with multivalent ions since the interaction energy between an ion and its background charge is directly proportional to $z^{3/2}$. Co-ions are then attracted to the interface to neutralize this excess counter ion charge, which is the main reason for surface potential reversal. This effect can also lead to oscillations in the surface potential. In this work one does not model the effect of charge inversion but present experimental evidence in support of such a mechanism.

B. Apparatus Results and Disscussion
1. Nernstian Vs. Non-Nernstian Surface

Before one describes the electrochemical gating response, one first highlights the difference between a Non-Nernstian and Nernstian surface. A Nernstian response implies that $\psi_O$ vs. $pH_B$ response is linear and has a slope of ~59 mV/$pH_B$. One may find that the surface dissociation constants and net surface site density play dominant roles in determining this slope, and can shift the response from Nernstian to non-Nernstian. The $pH_B$ response of an ISFET is traditionally given by $$\frac{\partial \psi_O}{\partial pH_B} = -2.3\frac{kT}{e}\alpha \quad (13)$$

where α is defined as;

$$\alpha = \frac{1}{1 + \frac{2.3kTC_i}{e\beta_s}} \quad (14)$$

here $$C_i = \frac{C_{DL} \cdot C_{Stern}}{C_{DL} + C_{Stern}},$$

and from Eq. (3);

$$\beta_S = \frac{2.3 \cdot eN_S \cdot H_S^+ \cdot (K_b H_S^{+2} + K_a K_b 4H_S^+ + K_a K_b^2)}{(K_a K_b + K_b H_S^+ + H_S^{+2})^2} \quad (15)$$

The $H_S^+$ at the interface at PZC is given by
$$H_S^+ = \sqrt{K_a \cdot K_b} \quad (16)$$

It is immediately clear that a pH insensitive interface (non-Nernstian) necessarily implies a small $\beta_S$. Equation (14) suggests an intricate interplay between ΔpK and $pH_B$. A low value of ΔpK and high $N_S$ is desired to achieve near Nernstian response. However the individual contributions of $K_a$ and $K_b$ are not immediately clear from Eq. (15). One may note that others have both simplified Eq. (6) while deriving the pH sensitivity and showed that the surface potential close to the PZC can be described by the relation;

$$2.3(pH_{PZC} - pH_B) = \frac{e\psi_O}{kT} + \sinh^{-1}\left(\frac{e\psi_O}{\gamma kT}\right) \quad (17)$$

Here $pH_{PZC}$ is defined by $$\frac{(pK_a + pK_b)}{2},$$

and $$\gamma = \frac{2e^2 N_S}{C_{Diff} kT}\sqrt{\left(\frac{K_a}{K_b}\right)}$$

is a dimensionless sensitivity parameter. In order to confirm this approximation and show that the pH sensitivity is strongly dependent on $N_S$ and $$\sqrt{\frac{K_a}{K_b}},$$

without making simplifications, one may first solve Eq. (13). One observes that if $K_b$ increases ($pK_b$ is lowered), the surface has more neutral groups and hence $pH_{PZC}$ extends into the acidic branch of the $pH_B$ response. Lowering $K_a$ ($pK_a$ is increased) ensures the same effect, extending the PZC more towards the base branch. It is important to note that when $pH_B$ is lower than $pK_a$, the surface will be mostly charge neutral and hence show a flat $pH_B$ response. This is graphically represented in FIG. 9a. However, when $K_a$ increases, $\Delta pK$ decreases and the response becomes more Nernstian.

A smaller $\Delta pK$ creates more charged groups around the PZC, which improves the $pH_B$ response. Lowering $N_S$ reduces a and the slope of the $pH_B$ response, because a reduction in the number of ionizable groups decreases the net available sites for proton binding FIG. 9b. The PZC however does not change with varying $N_S$.

2. Electrochemical Gating

As previously mentioned, $E_{OX}$ will induce $\sigma_O$ and $\sigma_{DL}$ which together set $\psi_O$. For an interface exhibiting a single ionizable group (the single-pK model), $\sigma_O$ first responds to $E_{OX}$ until all charges ($N_S$) have responded. During this process $\psi_O$ does not change and the surface is said to be "buffering." However, in many cases with amphoteric interfaces such as $Al_2O_3$ and $SiO_2$ the nature of the buffering strongly depends on $\Delta pK$ hand $N_S$. The choice of $pK_a=10$ and $pK_b=5$ for the present polysilicon interface under consideration represents a non-Nernstian surface with a $pH_{PZC}$ around $pH_B=7.5$. This corresponds to low pH sensitivity in the given $\Delta pK$ range and hence extremely low buffering. In FIG. 9c and FIG. 9d, one may compare the change in $\psi_O$ for varying $E_{OX}$ at different $pH_B$ and $n_O$ values. A slight skewing is observed FIG. 9c. Buffering is rather weak for intermediate pH values close to the PZC but gets stronger at extreme pH values. The skewing (slight sigmoid tendency) indicative of buffering is tunable as a function of $E_{OX}$. In Fig. FIG. 9d, one may notice that the maximal change in $\psi_O$ with $E_{OX}$ is strongest for the lowest $n_O$. This is because at low $n_O$, very little charge is available to screen a given modulation in $\psi_O$ or $\sigma_O$, while at high $n_O$ a small shift in $\sigma_O$ can cause large changes in $\sigma_{DL}$ and hence a substantial swing in $\psi_O$ is energetically unfavorable.

Under negative $E_{OX}$ conditions one may notice that varying $pK_b$, as shown in FIG. 9e modulates the surface potential even at zero $E_{OX}$. Such changes in surface ignitability can be achieved by suitable self assembled monolayer (SAM) formations. If one flips the surface constants, i.e. $pK_a=10$ and $pK_b=5$, maximal buffering is observed within the $\Delta pK$ range indicating a Nernstian pH response, as shown in FIG. 9f. As previously mentioned, the effect of the ion size was weak for NaCl salts in these simulations as $\psi_O$ never rose above $$\sim 4-5\frac{kT}{e}.$$

The above simulations show that in addition to pH and bulk salinity $E_{OX}$ can be tuned to affect the properties of the interface to a desired region of operation.

3. EOS Capacitance-Voltage (CV) Measurements

Polysilicon-Oxide-Silicon capacitors were fabricated as described earlier. $V_{REF}$ was swept from $-10V$ to $+10V$. At $-10V$, the silicon was in accumulation (positive interface charge). As $V_{REF}$ was swept positive, the charge in silicon was depleted, and finally at $+10V$ it was inverted. The effect of the double layer modulation or $pH_B$ on the surface potential is that the DC operating point is affected, which shifts the flat-band voltage ($V_{FB}$) of the capacitor stack as illustrated in FIG. 10a. In FIG. 10 one may chose to plot only the transition region and not the entire range of the $V_{REF}$ sweep.

A linear response in $V_{FB}$ with respect to $pH_B$ variation was noticed ($\sim50$ mV/pH) when sweeping $V_{REF}$ from $-10V$ to $+10$ V. A strong hysteresis effect was observed when $V_{REF}$ was cycled from $-10V$ to $+10V$ and back to $-10V$ as shown in FIG. 10a, for $pH_B=7$ and $pH_B=9$. This hysteretic effect got slightly larger with decreasing $pH_B$ (not shown) and was found to be strongly dependent on the type of interface. For example, one may find that both $Al_2O_3$ and poly-Si interfaces showed distinct hysteresis while thermal $SiO_2$ showed a negligible hysteresis upon exposure to pH solutions (not shown). Since $E_{OX}$ can influence $\sigma_O$ similar to the effect of $pH_B$, as described earlier FIG. 9, the varying DC sweep affects the ionization state of the interface which in turn affects surface recovery. When $V_{REF}$ is swept from $-10V$ to $+10V$, the field in the oxide in the beginning promotes anion adsorption or interface deprotonation and results in a negative $\sigma_O$. This deprotonation effect is strongly dependent on the choice of $pK_a$ and $pK_b$. As the forward sweep proceeds towards $+10V$, this negative charge is poorly neutralized due to a small $\beta_S$, which renders a higher $V_{FB}$. On the reverse sweep, the surface is completely protonated or neutralized and hence $\sigma_O$ is more positive. This $+\sigma_O$ only dissociates over the time course of the sweep, resulting in a lower $V_{FB}$. The hysteresis is similar to the trap charge effect in electronic devices. In order to confirm that this hysteretic effect is indeed mostly due to protons instead of ions, one may perform CV sweeps at different $n_O$ at $pH_B=7$ and find that the hysteretic window was almost independent of $n_O$. $V_{FB}$ increased by $\sim30$ mV when $n_O$ varied from 100 µM to 1 mM but then slightly decreased upon further $n_O$ increase as illustrated in FIG. 10b. This slight dependence of $\psi_O$ on $n_O$ is attributed to $\beta_S$. The sensitivity of $\sigma_O$ to changes in the bulk electrolyte can be estimated by $$\sigma_O = C_i \cdot \psi_O = -\sigma_{DL} \qquad (16)$$

where $C_i$ is the total capacitance seen by the interface:

$$C_i = \frac{C_{DL} \cdot C_{Stern}}{C_{DL} + C_{Stern}} \qquad (17)$$

Here $\sigma_{DL}$ is the charge in the double layer, and $C_{Stern}$ is the Stern layer capacitance which is generally considered immobile. A change in $n_O$ directly affects $\sigma_O$ via $\sigma_{DL}$ [Eq. (16)] which in-turn affects $C_{DL}$ and $\psi_O$ self-consistently. The Boltzmann relation in Eq. (7) directly implies that a change in $\psi_O$ affects $H_s^+$. However, the surface buffering capacity $\beta_S$ will try to maintain $H_s^+$ constant by ensuring a new surface chemical equilibrium satisfied by Eq. (8). If $\beta_S$ is small, $C_{DL}$ can strongly regulate $\psi_O$, where the surface is maximally sensitive to ions and least sensitive to pH.

In order to further validate field-dependent ionic activity, one may also vary the $$\frac{z}{v}$$

(valency/volume) ratio of the cation. Ionic size and valency play a crucial role in the double layer formation. Hence field-induced double layer modification serves as a suitable control to validate electrochemical response over the electrolyte interface. Size and valency sets a constraint on the width of the double layer which is strongly surface potential dependent. When $V_{REF}$ was swept from −10V to +10V one may observe a reduction in $V_{FB}$ when $MgCl_2$ replaced NaCl in the electrolyte but a slight increase in $V_{FB}$ when $Co(NH_3)_6Cl_3$ replaced $MgCl_2$, see FIG. 10c. For the latter, this effect was accompanied by a corresponding decrease in the accumulation capacitance $C_{acc}$, while with $MgCl_2$, $C_{acc}$ increased. One may attribute the decrease in capacitance with $Co(NH_3)_6Cl_3$ to the Steric effect, which imposes packing constraints on the thickness of the condensed ionic layer and the effective $C_{Stern}$. It however appears that under the given field conditions and concentrations of $MgCl_2$ used the Steric effect factor is less dominant.

However, the net reversal in $\psi_O$ observed with the trivalent cations cannot be accounted for solely by the Steric effect. $\psi_O$ reversal is possible with trivalent ions even at extremely low $n_O$ primarily due to electrostatic correlations. This seems to suggest that the predominant factors that determine the onset of potential reversal are the ionic $$\frac{z}{v}$$

ratio and strong ion-ion interaction between multivalent ions.

4. Floating Gate Based Sensor Structure a. Transient Responses

FIG. 11a to FIG. 11f summarizes the transient responses of the CvMOS for varying $n_O$ under different $pH_B$ conditions of 11, 7 and 3. The electrolyte bulk was held constant at 0.8V with respect to the source at ground. The CG pulse train was switched between +15V and −15V while reading intermittently at +10V. The drain bias $V_D$ was held at 1V throughout the experiment. When a +15V CG bias was applied, $I_D$ increased. However, the field in the SG oxide ($E_{SG\_OX}$) during the rising pulse became more positive looking into the electrolyte. This immediately resulted in a net negative charge in solution by a combination of $\sigma_O$ and $\sigma_{DL}$. When the CG was re-biased to +10V, the $-\sigma_O$ induced during the previous +15V application remained at the surface (hysteresis). This caused the $I_D$ between 110-170 seconds to be smaller than the initial 0-55 seconds. On application of a −15V CG bias, $E_{SG\_OX}$ became negative and caused a net positive charge building up at the SG interface which enhanced $H^+$ adsorption. When the CG was re-biased to +10V between 230-285 seconds, $I_d$ was higher than the initial readout state between 0-55 seconds, as illustrated by the dotted line in FIG. 11b. In order to confirm that protonation was the dominant effect during and after the negative gating period, one may perform experiments in the presence and absence of a competing solution buffer (TRIS), see FIG. 12b at $pH_B=7$. In the presence of TRIS, no increase in current was observed after application of the −15V CG pulse. In the absence of electrolyte and with the SG directly probed to ground, see FIG. 12c, the transient current recording showed no variation after +10V, +15V and −15V CG bias application. This strengthens the assertion that no charge was either injected or erased into the FG during the CG bias application and the main reason for the observed differences in current levels is surface charge regulation.

For $pH_B=11$, the surface was already buffering FIG. 11d within the experimental $E_{SG\_OX}$ range (the un-shaded region). One may observe that $\psi_O$ was negative in the beginning, close to the zero $E_{SG\_OX}$ condition. With increasing $n_O$, $\psi_O$ became more positive, which was reproduced in the transient response (i.e., FIG. 11a) reflected by a higher $I_D$ for increasing $n_O$ within the initial 0-60 seconds. After application of a −15V CG pulse between 170-230 seconds, however, we observed a recovery to higher $I_D$ and a longer settling time with decreasing $n_O$. One may attribute this to an increased hysteretic effect possibly due to increased cation adsorption at high $pH_B$. This coupled with a larger surface potential shift at lower $n_O$ can potentially lead to different rates of surface re-equilibration. Quantification of cation adsorption under such conditions however is difficult to decouple and is at present a measurement challenge. At $pH_B=7$, however the surface potential was closer to zero around the readout condition of $E_{OX}\sim0.01$ V/nm. The model dictated a reversal in $\psi_O$ (i.e., see FIG. 11e) when $E_{SG\_OX}$ toggled between positive and negative values. This was experimentally observed in FIG. 11b with opposite shifts in $I_D$ after the +15V and −15V CG pulses in comparison with the initial 0-60 seconds. This clearly showed that although during readout $E_{SG\_OX}$ was close to zero, the carryover net charge and $\psi_O$ from the previous CG pulse remained and thus the gated surface state was observed. At $pH_B=3$, $\psi_O$ was highly positive (i.e., see FIG. 11f) to begin with and increased with decreasing $n_O$. $I_D$ was also found to increase after gating by positive and negative fields, as illustrated in FIG. 11c.

b. Quasi-Static Response

FIG. 13a summarizes the pH response of the floating gate based sensor structure in terms of the $V_{th}$ shifts observed from CG ($V_{th\_CG}$). $\psi_O$ was calculated via Eq. (1) after extracting the capacitive amplification ratio experimentally as in FIG. 6a. The $pH_B$ response showed a non-Nernstian characteristic with a clear plateau around $pH_B=8$ (i.e. $pH_{PZC}$). Increasing $n_O$ lowered $\psi_O$ at low $pH_B$ but enhanced $\psi_O$ slightly at high $pH_B$. This is consistent with the notion that ion adsorption plays little role in shifting $\psi_O$ at physiologically relevant $pH_B$, because the opposite would have meant an increase in $\psi_O$ due to $Cl^-$ ion binding. Also as $n_O$ increases, the surface buffering property decreases and hence affects the overall $pH_B$ response. This can be understood from Eq. (13) and specifically by closely examining the sensitivity parameter $\alpha$. It is immediately clear that a small $\mu_S$ competes with $C_i$ and determines the overall $pH_B$ response as a function of $n_O$. At high $n_O$, $C_i$ is much larger than $\beta_S$ and hence results in a reduced $pH_B$ response. At high $pH_B$ the slight increase in $\psi_O$ with varying $n_O$ can be attributed to simultaneous $H^+$ and $Na^+$ ion binding. This range of $pH_B$ however is too small to establish a meaningful conclusion. It is quite clear that changing $n_O$ does have an influence on $\beta_S$ and $\psi_O$ primarily from the buffering perspective. One may consider, however, that $n_O$ would affect $\psi_O$ even for surfaces that are uncharged or exhibit a constant charge condition. This would then primarily occur due to the change in $C_i$. FIG. 13b provides a fit to the experimental $pH_B$ response using the 2pK model presented earlier. A $pK_b$ of 5.0 and $pK_a$ of 10.0 was extracted. FIG. 13c and FIG. 13d shows the simulated effect of $E_{OX}$ induced gating on the $pH_B$ response for two distinct combinations of $pK_a$ and $pK_b$. In both cases the $pH_{PZC}$ shifts to higher pH values as $E_{OX}$ increases. However for the non-Nernstian interface where $pK_b$ is lower than $pK_a$ FIG. 13d, the shift in $pH_{PZC}$ is much higher (horizontal arrow). The pH insensitive region for this surface moves towards lower $pH_B$ values as $E_{OX}$ increases (dotted arrow). This shows that the effect of $E_{OX}$ is similar to varying $pH_B$ as both can tune $\sigma_O$. $E_{OX}$ serves as an electrical factor, while $pH_B$ as a chemical factor. We also experimentally observed this electrochemical gating effect by injecting charges onto the FG. We applied a CG bias of ~40V for approximately 30 seconds while holding $V_{REF}$ at 0V. Due to the larger capacitive coupling from SG, $V_{FG}$ remained closer to $V_{REF}$ and did not rise by more than 4~5V. $E_{CG\_OX}$ during this pulse period promoted FN tunneling which resulted in a net positive $Q_{FG}$. It is important to note that in the present study, with the given geometry constraints, $E_{SG\_OX}$ potentially achieved values of 0.02-0.2 V/nm when $Q_{FG}$~8-20 pC. A quick (15 seconds) CG ramp was used to monitor the new surface charge state. One may find that with +$Q_{FG}$ present, the $pH_B$ response was dramatically affected and the pH insensitive region moved to lower $pH_B$, which resulted in an overall reduced pH response (i.e., see FIG. 13e), which is in line with the simulation result shown in FIG. 13d. The surface model also dictates that by reducing the density of surface hydroxyl groups, the $pH_{PZC}$ shift was more pronounced (i.e., see FIG. 13f). Taken together the CV, IV and transient responses suggest that surfaces exhibiting a non-Nernstian response with large ΔpK will undergo a hysteresis in a saline environment. Ion adsorption does play a role under certain $pH_B$ conditions but a better treatment of the site binding parameters is needed to account for such subtle effects.

c. Programming Response and the Role of the Reference Electrode

One may recall that $V_{FG}$ is influenced by $\psi_O$ which is $pH_B$ and $C_{DL}$ dependent. Also from the transient measurements it is clear that at small positive CG pulses the net carry-over charge is negative. Hence as $V_{CG}$ is initially increased, $V_{FG}$ perturbs $\psi_O$ inducing a net $-\sigma_O$ which couples back to influence the transistor current. As $V_{CG}$ is further increased $V_{FG}$ does not rise as high due to the influence of $V_{REF}$. The $E_{CG\_OX}$ increases favoring FN tunneling to create a net positive $Q_{FC}$, reducing $V_{th}$ measured from the CG as illustrated in FIG. 14a. $V_{FG}$ is more positive as the tunneling process ensues due to the positive $Q_{FG}$ (see FIG. 6c). This would necessarily imply that $E_{CG\_OX}$ lowers and $E_{SG\_OX}$ increases. The total threshold voltage shift ($V_{th\_CG}$) is attributed to $Q_{FG}$ and its net effect on $\sigma_{DL}+\sigma_O$. One may consider that during tunneling, there is no charge leakage into the solution as measured in control experiments (not shown). When the reference electrode is floated, however, the capacitive coupling dramatically reduces and the FG is no longer pulled to a defined electrolyte potential. This ensures that $V_{FG}$ rises with $V_{CG}$ with increasing $E_{TOX}$ to promote electron injection ($-Q_{FG}$) into the FG, thereby increasing the $V_{th}$ measured from the CG (see FIG. 6b). This operation is particularly significant when attempting to manipulate charged biomolecules such as DNA.

In order to confirm the interplay between $\sigma_{DL}$ and $Q_{FG}$, one may perform experiments by changing $n_O$ and hence $C_{DL}$. It may be found that $C_{DL}$ is strongly influenced by the tunneling characteristics as illustrated in FIG. 14a. As $C_{DL}$ lowered so did the $V_{REF}$ coupling to the FG. This caused $V_{FG}$ to rise higher with $V_{CG}$ which lowered electron out-tunneling and favored electron in-tunneling, and hence resulted in a smaller net $Q_{FG}$ after $V_{CG}$>30V. The small initial increase in $\Delta V_{th}$ at low to moderate CG voltages is attributed to surface deprotonation and a net remnant negative $\psi_O$ when $V_{CG}$ is too low to cause tunneling.

In many experiments involving cell suspensions and biomolecules, the electrolyte composition is never just composed of single monovalent salts. In order to further develop the gating concept and corroborate the CV measurements, one may perform experiments keeping $n_O$ constant at 20 mM and varying the cationic $\frac{z}{v}$ ratio, see FIG. 14b. One may observe that in the vicinity of the knee point [denoted by the arrow in FIG. 14b] where tunneling had just begun, the reduction in $V_{th}$ was slightly more pronounced for $Co(NH_3)_6Cl_3$ in comparison to NaCl and $MgCl_2$. This result shows that with $Co(NH_3)_6Cl_3$ present, $\psi_O$ increased just after the programming pulse application. That is, it became more positive with +$Q_{FG}$. This finding is in line with the +10V to −10V $V_{REF}$ (reverse) sweep performed during CV analysis FIG. 10c in which $\psi_O$ was observed to be more positive (lower $V_{FB}$) with Co $(NH_3)_6Cl_3$. It is important to note that E-fields with similar strength and polarity are developed in the underlying oxide either under +$Q_{FG}$ conditions in the CvMOS or low to moderate $-V_{REF}$ application in the EOS structure. Taken together experimental evidence suggests field induced surface potential reversal due to a combination of both $C_{DL}$ lowering and correlation effects when experimenting with trivalent salts. This effect was not observed with monovalent or divalent salts. In FIG. 14b, the overall magnitude of $\Delta V_{th}$ was also found to be lower for $Co(NH_3)_6Cl_3$. This is again consistent with the notion that $C_{DL}$ affects the net $Q_{FG}$ [FIG. 14a], and is in accordance with the CV measurements presented earlier in which $C_{DL}$ was found to reduce for trivalent salts.

5. Concluding Remarks Regarding Apparatus

The embodiments provide a floating gate based sensor apparatus that presents a dynamic surface charge modulation of a solid-electrolyte interface, and the concept of surface pH tuning. By modulating the polarity of stored charge, one can switch between a pH sensitive condition and a non-Nernstian surface. Transistor and EOS capacitor measurements are compared and a 2-pK model with surface charge regulation is presented. One may conclude that proton adsorption and desorption is the primary reason for hysteresis at such interfaces, which also provides a method of probing the surface charge state. Quasi-static I-V measurements, CV profiles and high resolution transient recordings are presented to corroborate related findings.

B. Applications of Floating Gate Based Sensor Apparatus in Accord with Embodiments for Biomaterial Detection and Manipulation Various embodiments of the floating gate based sensor apparatus in accordance with the embodiments can be utilized for the detection and/or manipulation of biomolecules. Indeed, the detection and manipulation of biomolecules, especially simultaneously, provides for analysis of the fundamental properties of proteins/DNA, controlled drug delivery and reversible bio-electronic interfaces. While biomolecular detection by transistors has been described, it has so far been very difficult to realize the opposite, i.e., using the transistor for molecular actuation. Serving as an affordable, fast and extremely sensitive tool, the transistor platform is easier to integrate and scale than optical techniques and could also facilitate label-free readout. Present non-faradaic sensors rely on the conventional ISFET (ion sensitive field effect transistor) approach. The surface of the open-gate field effect transistor (FET) is made sensitive to ion and molecule adsorption, which subsequently modulates the transistor current. The threshold voltage in this case is measured with respect to a reference electrode, often by Ag/AgCl in a chlorine-rich buffer. However, recent efforts have been directed towards achieving dual gate control which gives intrinsic amplification of the surface potential shift. Given the small size and high sensitivity of these dual-gate devices, sensing the intrinsic properties and interactions of proteins, DNA and other small bio-molecules becomes plausible.

Traditionally, the gate metal of the FET is removed and sensing is performed on the gate oxide or functional coatings. Alternatively, the gate metal can be left electrically floating and the target adsorption is on the metal surface. A reference electrode such as Ag/AgCl or Pt in the electrolyte biases the transistor at the appropriate operating point. This is commonly known as the ISFET. In comparison, the floating gate based sensor apparatus in accordance with the embodiments makes use of an independently driven control gate, hence alleviating the sole reliance on the reference electrode for biasing, which can nevertheless still be used to set the bulk electrolyte potential and affect the sensor output. The use of $V_{REF}$ can lower the read voltage to avoid read disturb, as high $V_{CG}$ can induce unintended nonvolatile charge injection.

1. Biomolecule Detection and Manipulation
   a. Introduction

Optical detection schemes of DNA hybridization and protein binding traditionally rely on fluorescent labels. Not only can labeling affect the delicate nature of molecular interactions, but integrating optical detection with sub-millisecond monitoring is difficult. CMOS electrochemical sensors on the other hand, enable aggressive miniaturization, label-free operation, high spatial and temporal resolution, and high sensitivity based on both capacitance and charge. Moreover, transistor detection of DNA hybridization through surface charge sensing can potentially realize electronic micro-assays.

Recent efforts towards dynamic control of biomolecular activity have included electrophoretic and electrochemically driven stimuli. Electric-field manipulation is preferred compared to faradaic schemes as redox reactions often interfere and disturb the delicate molecular properties. It is also possible to ensure sufficiently high electric field gradients with low-voltage operation which is dependent on the double layer capacitance. Under such conditions, it was proposed that the sensing electrode can still be treated as purely polarizable, as in the conventional Gouy-Chapman (GC) double-layer theory.

Previous research has provided compelling experimental evidence that the oligonucleotides desorption occurred during an unsteady electrochemical state away from equilibrium, contrary to the notion that desorption was well captured by the GC model where an equilibrium could always be established. Similar studies demonstrated that DNA desorption occurred after sub-milli-second pulses between a surface electrode and the bulk electrolyte, further indicating that desorption happened well before equilibrated double-layer conditions were reached. This was believed to be primarily due to counter ion descreening exposing the DNA backbone which gets electrostatically repelled, reorganizes and then re-adsorbs. More recently, the effect of self-heating in SOI transistors was demonstrated as a method for local desorption with simultaneously sensing capabilities. This is an attractive alternative approach but precise thermal control at such scales is still challenging.

On the other hand controlled nonvolatile charge injection, by either hot electron injection or Fowler-Nordheim (F-N) tunneling causes the FG to hold static charge of either polarity. This charge capacitively couples to the sensing gate which imparts an electrostatic force on ions and adsorbed biomolecules.

Accordingly, described below is the sensing and dynamic manipulation of surface-immobilized DNA using the floating gate based sensor apparatus in which quasi-static I-V and impedance spectroscopy measurements are performed. The measured $\psi_O$ during DNA immobilization and hybridization is E-field dependent. A positive E-field enhances the hybridization and immobilization signal while a negative E-field reduced it. In addition dual-gate control and charge programmed onto the FG affects the sensitivity by inducing different field conditions in the SG oxide. Manipulation of the oligonucleotides is realized via non-volatile charge injection which set a defined repulsive/attractive field between the FG and solution. The ionic cloud and associated de-screening around DNA is believed to be responsible for this effect as it can be perturbed via the field effect. This is further corroborated by modeling the DNA membrane using modified screening and partition energy formulations. The modified permittivity due to the partition energy difference which could arise either due to orientation or ion specific exclusion effects is found to play a key role. Furthermore $V_{th\_CG}$ and $\psi_O$ are observed to recover after DNA desorption aided by the non-covalent nature of the binding. Impedimetric detection using a split-gate approach showed a clear shift in the frequency response upon DNA immobilization (pole) and subsequent hybridization (pole and zero).

According to an embodiment, two different lengths are tested (24 bp and 48 bp) and the results indicate that the impedance recovers upon charge injection indicating surface recovery. The frequency response is also found to exhibit a molecular weight and structure dependence. Upon programming the FG with electrons, the interface impedance is observed to recover, indicating DNA desorption. This technique of combined detection and manipulation using CMOS compatible charge sensors can potentially help realize electrically addressable sensor arrays, refreshable bio-sensor interfaces and dynamic reconfiguration of protein complexes, among many other applications.

b. Experimental Considerations
   i. Materials

The sensor chips utilized were as described above. The sensing gates were coated with a receptor, poly-l-lysine (Sigma Aldrich), set aside for two hours and then washed with DI water, dried and stored at 4° C. before use. DNA strands B1 and B2 (see Table 1) were procured from IDT DNA and were 99.9% HPLC purified. These 20 base-pair (bp) oligonucleotides (~7 nm length) were kept at a stock concentration of 0.5 mM in a 10 mM saline (TE) buffer (10 mM Tris at pH 8.0, 10 mM NaCl, and 1 mM EDTA). The DNA concentration used during measurements was diluted to ~5 µM in order to achieve sufficient surface coverage without suffering from Coulombic repulsion which normally occurs at high probe densities. DNA strands (C1, C2) (24 bp) and (D1, D2) (48 bp) were additionally used under identical conditions to ascertain the impedance dependence on molecular length before and after hybridization. The bond pads were isolated from the sensing region via an epoxy coating which also served as the fluid reservoir. Fluid was dispensed and removed from the well via pipettes.

TABLE 1

| Name | Sequence (5' to 3') |
| --- | --- |
| B1- probe | CATAGGCCTTGGAACCTATG (SEQ ID NO. 1) |
| B2- target | CATAGGTTCCAAGGCCTATG (SEQ ID NO. 2) |

TABLE 1-continued

| Name | Sequence (5' to 3') |
|---|---|
| C1-probe | GCATCTGGGCTATAAAAGGGCGTCG (SEQ ID NO. 3) |
| C2-target | CGACGCCCTTTTATAGCCCAGATGC (SEQ ID NO. 4) |
| D1-probe | GCATCTGGGCTATAAAAGGGCGTCGGTATCCAAGGTTCCGGATACGAG (SEQ ID NO. 5) |
| D2-target | CTCGTATCCGGAACCTTGGATACCGACGCCCTTTTATAGCCCAGATGC (SEQ ID NO. 6) |

Although the sensing gates were coated with poly-l-lysine as the receptor, many other types and varieties of receptors are possible. Examples of possible receptors include, but are not limited to (3-Aminopropyl)triethoxysilane (APTES), mercaptopropyltrimethoxysilane (MPTES), poly-l-lysine, poly-d-lysine, (3-Glycidyloxypropyl)triethoxysilane (GPTES), poly-ethylene glycol (PEG) receptors, laminin, and/or fibronectin, in addition to many others. Since the receptor used to coat the sensing gates can be determined by the target of choice, the possible receptors are only limited by target/receptor pairs. In addition, if a receptor is used to hunt or determine targets, the receptor can be chosen without knowing the particular target.

ii. Electrical Instrumentation

Impedance measurements were performed by monitoring the small-signal transistor gain as a function of frequency. A single-toned sinusoid waveform was applied (Stanford Research Systems DS345, CA, USA) through a solution gate (Ag/AgCl reference electrode) while the DC bias was supplied via the control gate independently (Keithley 2400, USA). The output current of the transistor was fed to a lock-in amplifier (Stanford Research Systems, SR844, CA, USA) through the TIA. Bode responses and current/voltage (I/V) sweeps were measured intermittently to ascertain the operating point stability. The CG was then adaptively biased to maintain a constant operating point during the impedance measurement.

c. Device Operation and Sensing Principles i. Quasi-Static Operations $V_{FG}$ is perturbed by analyte adsorption on the SG. Upon DNA immobilization, the readout current is modulated by a change in the $V_{FG}$ from both the SG capacitance $C_{SG}$ and $\psi_O$ as outlined (see FIG. 4). A $V_{CG}$ sweep is then performed to determine $V_{th\_CG}$ when the drain current is at a constant 1 µA. As highlighted above, $V_{th\_CG}$ driven readout results in an amplified measure of $\psi_O$ and the amplification factor is primarily determined by the ratio between the two input capacitors $C_{SG}$ and $C_{CG}$.

Note that DNA itself is a dielectric and hence will give rise to additional capacitive effects at the interface, which is noticeable but not well understood, as the rotation angle will further affect the capacitive readout. The subthreshold slope is directly proportional to the total capacitance $C_T$ (see FIG. 14) seen from the FG, which makes the I/V sweep a unique method to simultaneously obtain $\psi_O$ and total capacitance. In addition, by monitoring the subthreshold slope the reliability of the device is continuously monitored since a degradation in slope can indicate ion migration into silicon for permanent device failure. In comparison, transient current measurements performed at a fixed CG bias reflects the combined effect of time-resolved shifts in $\psi_O$ and net capacitive coupling.

ii. DNA Transistor Interface

Over the last few years many models of the DNA-transistor interaction have been proposed to highlight the nature of charge modulation at the ISFET interface. Various groups have illustrated the effects of the adsorbed biomembrane as ion permeable, resulting in a Donnan potential. Additionally, it has been shown that high intrinsic surface charge density negates and even cancels the Donnan effect. Hence a Nernstian pH response is deleterious to biomolecular sensitivity. However, it was recently shown that the maximal sensitivity of protein detection coincided with maximal pH sensitivity, in direct contradiction to known theories. It was argued that this is due to the interaction of the protein with surface sites, and hitherto this issue still had not been resolved.

The Donnan theory formulation was later improved wherein ion permeation into the DNA layer was treated by accounting for the partition energy barrier. It was explained that ion diffusion from a high permittivity medium (bulk) to a low permittivity medium (the DNA membrane) is always associated with an energy penalty, leading to a low ion density within the membrane. DNA orientation on the surface plays an important role as it decides the net partition energy barrier. It is thus reasonable to assume that the field in the underlying oxide plays an important role in determining the overall sensitivity as molecular orientation and the local ionic environment can be field dependent.

Accordingly, described below are experiments in which different ion screening profiles are incorporated within and outside the DNA membrane, and it is shown that this leads to a pronounced effect on the measured $\psi_O$. Further, the model framework to compare different partition energy barriers for distinct configurations is then presented.

iii. Impedance Spectroscopy

Impedance spectroscopy was realized through small-signal analysis using a split-gate approach as CG sets the DC bias and $V_{REF}$ delivers the AC excitation independently. This scheme has an important advantage to independently tune the transistor's DC operating point at the pixel level while maintaining a constant global AC perturbation in the buffer. DNA immobilized on the sensing gate is analogous to an additional dielectric layer with a counterion cloud which can be modeled by an equivalent RC circuit. The main reason that justifies the RC model is that when operating at high DNA concentrations in this case ~1-5 µM, the DNA strands orient in such a way to minimize Steric interactions and reduce the overall free energy. This results in a tightly packed film. The adsorbed DNA is also known to form an ion permeable membrane which causes a fixed charge density within the adsorbed DNA film. This allows for a Donnan potential to be set within the membrane which further affects the surface potential shifts. In the AC impedimetric mode, this introduces a strongly resistive component into the interfacial impedance in addition to the dielectric property of the DNA. The frequency responses are attributed to both resistive and capacitive changes at the interface. The transfer function can be modeled by a Bode (pole-zero) plot. Accordingly, such impedimetric approaches can be viewed as simple two-electrode systems, but integrating with FET's allows for simultaneous charge and capacitance estimation at the nanoscale.

The small-signal output can be represented by the simple relation $v_{out} = i_d \times R_D$ where $R_D$ is the feedback resistance and $V_{out}$ is the small-signal output of the transimpedance amplifier. The small signal current $i_D$ can be approximated by $g_m v_{gs}$ where $g_m$ is the transconductance of the amplifier and $v_{gs}$ is the intrinsic small-signal gate-to-source voltage. The transfer function $H(j\omega)$ depicting the relaxation across the DNA monolayer accounts for the effective reduction in $v_{gs}$, which further relates to the output voltage by $v_{out}=g_m H(\omega) \times v_{ac} \times R_D$. $H(j\omega)$ can be expanded to;

$$H(j\omega) = \frac{1 + j\omega \times (R_{DNA} \times C_{DNA})}{1 + j\omega \times (R_{eff} \times (C_{OX} + C_{FG-BULK} + C_{DNA}))} \quad (18)$$

where $\omega$ and $V_{ac}$ are the frequency and small-signal bias applied while $C_{OX}$ is the gate oxide capacitance. The DNA monolayer is described by a resistance ($R_{DNA}$) and capacitance ($C_{DNA}$) in parallel. $R_{eff}$ is the cumulative resistive contributions from both the reference electrode, the electrolyte and the adsorbed DNA film. $C_{FG-BULK}$ is the parasitic capacitance from the floating gate to bulk.

The frequency response of the interfacial RC network has the pole ($P_1$) primarily dependent on the gate oxide capacitance, associated parasitics and electrolytic resistance. The first zero ($Z_1$) is described by the relaxation across the DNA film at the interface. In the absence of DNA, $Z_1$ does not exist;

$$P_1 \cong R_{eff} \times (C_{OX} + C_{FG-BULK} + C_{DNA}) \quad (19)$$

and;

$$Z_1 \cong R_{DNA} \times C_{DNA} \quad (20)$$

By performing frequency sweeps, one can monitor the properties of the adsorbed film given that the operating point is held constant. Impedance spectroscopy can also provide a suitable method to benchmark the effects of charge-injection-induced surface manipulation, as reflected in the capacitance and resistance of the interfacial layer.

d. Biomaterial Detection and Manipulation Results and Discussion i. Quasistatic Readout FIG. 15a depicts variation in $\psi_O$ upon ssDNA immobilization (DNA sequence C1) and subsequent complimentary pair addition (DNA sequence C2) under different biasing conditions. The SG surface is coated with PLL which neutralizes the intrinsic hydroxyl charge rendering it suitable for DNA adsorption. It is observes that when DNA immobilization and hybridization is measured with respect to $V_{REF}$ with $V_{CG}$ grounded, $\Delta\psi_O$ is smaller even after compensating for capacitive amplification. This is in contrast to $V_{CG}$ readout with $V_{REF}$ pinned at 0.2V. This variation is attributed to differences in $E_{SG\_OX}$ during readout. A more positive $E_{SG\_OX}$ at 0.05 V/nm exists during CG readout in comparison to $V_{REF}$ readout where $E_{SG\_OX}$ is about 0.005 V/nm. This difference is balanced by a corresponding change in screening charge around the DNA molecule. The change in fields can also weakly influence the molecular orientation. This is attributed to the lower screening charge within the membrane which results in a larger $\psi_O$ shift. In order to further validate this effect, $V_{CG}$ was offset during the $V_{REF}$ sweep to create different $E_{SG\_OX}$ conditions. Under normal vMOS operation such input offsets should only translate to a parallel shift in the transconductance responses. However, it was found that under $+V_{CG}$ offsets of +10V $\Delta\psi_O$ increased slightly upon (DNA sequence C1) and (DNA sequence C2) addition. A positive offset resulted in larger counter ion (cation) descreening within the DNA membrane. A −10V, $V_{CG}$ offset caused a negative $E_{SG\_OX}$ and resulted in an insensitive response. This is attributed to counter ion accumulation which screens out most of the DNA intrinsic charge. It may also affect the DNA orientation rendering it less likely to lie flat on the surface. A much reduced shift upon ssDNA (DNA sequence C1) addition and very little variation upon subsequent hybridization (DNA sequence C2) was observed. The given $V_{CG}$ and $V_{REF}$ biases are too low to cause program or erase operations on the FG. The change in $E_{SG\_OX}$ induced by a CG bias hence solely influences the DNA membrane.

In a separate study, depicted in FIG. 15b, in order to further corroborate field-induced DNA manipulation, pre-annealed dsDNA (C1, C2) was added onto the SG after programming (electrons stored) and erasing charges on and off FG. In this particular example, −10 pC of stored charge was observed upon programming (FG negatively charged) for a capacitive amplification factor of ~15. Nominally 8-20 pC of stored charge can induce a $$E_{SG\_OX} \sim \pm 0.02 \sim 0.2 \frac{V}{nm}$$

for the choice of capacitance ratios used in this study and also without the need for a continuously applied CG bias (part I). Such fields, as described in detail above, can lead to shifts in $\psi_O$ of ~50-70 mV ($pH_B$=8) during readout.

Once the FG is programmed or erased and DNA is added, the reference electrode and CG are temporarily floated prior to sweeping the CG bias for readout (i.e. a standby state). $\psi_O$ strongly tracks $V_{FG}$ during this period, primarily due to the strong capacitive coupling between SG and FG and weak coupling to the bulk. It is noted that the source and drain connections are not perturbed during and due to the extremely small capacitance coupling to the FG have a negligible influence on $V_{FG}$. $V_{FG}$ is then predominantly defined by $$\frac{Q_{FG}}{C_T},$$

which under the given conditions can reach values ~±0.2-0.3V just prior to the readout sweep. Such dramatic changes in surface potential can strongly influence the nature of DNA immobilization and manipulation, as interaction with a PLL-coated surface is mainly electrostatic in nature. It is interesting to note that the ideal condition would demand a low SG/CG and a large CG/FG coupling ratio to ensure maximal field modulation by injected charge. This however will affect the sensitivity to analyte detection. Hence it poses a design tradeoff.

In FIG. 15b after electron injection the shift in $V_{th\_CG}$ decreased slightly (+10 mV), while a significant increase in $V_{th\_CG}$ was induced upon hole storage (−150 mV). The above experiments indicate that DNA immobilization on SG is perturbed by attractive and repulsive force via charge-charge interaction and the underlying $E_{SG\_OX}$ can directly influence the adsorption and even the surface membrane structure. The ability to control DNA immobilization using programmed charge presents an opportunity to not only create addressable microarrays but also refresh the surface for continuous monitoring. For example, if hole injection promotes DNA adhesion and electron injection desorbs the adhered biomolecule, a buffer exchange after electron injection can refresh only the chosen sensor surface. Experiments were performed to corroborate this hypothesis. DNA hybridization and subsequent manipulation were performed on PLL-coated SG. A capacitance amplification ratio of 22 was extracted prior to adding DNA. Here the reference electrode was left floating during readout to ensure maximal field modulation from the injected charge instead of the potential difference between SG and the reference electrode. The implications of a floating electrolyte bias are discussed below. Unless otherwise mentioned, $V_D$ was held at 1 V during I/V sweeps.

Buffer was first dispensed and the I/V responses were recorded during the programming and erasing cycles. A significant $V_{th\_CG}$ shift of ~8V was observed implying ~+8 pC of stored charge (see FIG. 16a). Single stranded DNA (ssDNA) (C1) was then added under the erased condition (FG positively charged). The $V_{th\_CG}$ shift was recorded 15 minutes after ssDNA addition and was shown in FIG. 16b. Repeated sweeps were performed to make sure $V_{th\_CG}$ was stable before proceeding. The arrows indicate a net $-\psi_O$ contribution at the interface. Complimentary ssDNA (C2) subsequently created a further $V_{th\_CG}$ shift. We observe a $\Delta\psi_O$ on the order of ~100 mV upon C1 addition and a further 150 mV shift upon hybridization (see FIG. 16b), consistent with previous studies on floating-gate MOS interfaces but in contrast to the 10-20 mV shifts observed on conventional open-gate ISFET's.

Once a hybridization signal was recorded after ~40 min, a pipette was introduced filled with fresh buffer and gently sloshed back and forth 3~4 times till the entire buffer was replaced in order to remove loosely bound DNA. No $V_{th\_CG}$ shift was observed (see FIG. 16c), which was likely due to the firmly immobilized DNA. Electron injection was then programmed at this stage and the $V_{th\_CG}$ shift was observed. During tunneling the $V_{CG}$ pulse was maintained for a ~30 seconds. If the DNA molecules were to still be immobilized to the SG after programming, a further increase in $V_{th\_CG}$ should have been observed. However, it was observed that the $V_{th\_CG}$ coincided with the curve corresponding to the pure buffer response with injected electrons [FIG. 3(d)]. At this point, another buffer exchange was performed to remove any loosely bound DNA as a consequence of electron injection. After a subsequent erasing operation it was found found the $V_{th\_CG}$ overlapped with the trace corresponding to pure buffer as shown in FIG. 16d. It is critical to note that throughout the experiment the subthreshold slope did not degrade which is critical from a reliability perspective.

The effects of programming and erasing FG were compared with and without buffer exchange. The measurements indicated that after electrons were injected and subsequently erased and without replacing the buffer, $V_{th\_CG}$ recovered to the same point. Complete $V_{th\_CG}$ recovery was obtained only with electron injection and buffer exchange. This suggested that injection manipulated and weakened the DNA surface interaction, allowing complete desorption during the buffer replacement. However without buffer exchange, DNA would be re-adsorbed.

During the initial rising CG pulse, $V_{FG}$ increases and after 10 ms significant amount of electrons begin to tunnel onto the FG. This electron accumulation in turn reduces $V_{FG}$ (i.e. a negative feedback). When the CG and reference electrode are momentarily open circuited prior to readout, $V_{FG}$ is highly negative and strongly couples to the SG as previously mentioned. DNA is then strongly manipulated, i.e. DNA manipulation possibly occurred even before a steady state condition (readout) was reached. FIGS. 15 and 16 thus suggest that under $+E_{SG\_OX}$ conditions, DNA is attracted towards the surface but after FG programming the DNA desorbs as it interacts with the stored electrons. The dynamics of manipulation during and just after the tunneling operation is still actively being resolved.

ii. The DNA Transistor Interface Model

In order to corroborate the potential shifts and understand the true nature of the observed signals, the DNA interface stack was simulated using the following approach (see FIG. 17a). The total charge density within the DNA membrane is given by $\rho_{DNA}+\rho_{ions}$, where $\rho_{ions}$ is a function of $\psi$. The total screening charge in the DNA membrane is then given by;

$$\frac{d^2\psi}{dx^2} = -\left(\frac{\rho_{DNA} + \rho_{ions}(\psi)}{\varepsilon_{eff}}\right) \tag{21}$$

where $\rho_{DNA}$ is a constant background charge, i.e. similar to how dopants in a semiconductor are treated. Ions are mobile and are akin to electrons and holes. Equation 21 is then reformulated into the form;

$$\int_{E_o}^{E_{\beta 1}} E\,dE = -\frac{1}{\varepsilon_{eff}}\rho_{DNA}(\psi_\beta - \psi_O) - \frac{1}{\varepsilon_{eff}}\int_{\psi_o}^{\psi_\beta} \rho_{ions}(\psi)\,d\psi \tag{22}$$

where $\varepsilon_{eff}$ is the effective permittivity of the DNA membrane and the subscript $\beta$ represents the boundary between the DNA and bulk electrolyte presented in FIG. 17b. $E_O$ represents the field in the DNA membrane at the oxide interface such that it satisfies the condition $\varepsilon_{OX}E_{OX}=\varepsilon_{eff}E_O$. A Stern layer has not been assumed in the present simulation. Similarly the region from the DNA membrane into the bulk shown in FIG. 17b is re-formulated as;

$$\int_{E_{\beta 2}}^{0} E\,dE = -\frac{1}{\varepsilon}\int_{\psi_\beta}^{0} \rho_{ions}(\psi)\,d\psi \tag{23}$$

where $\varepsilon_{eff}E_{\beta 1}=\varepsilon E_{\beta 2}$ across the DNA electrolyte interface as a discontinuity in the E-field would exist due to the differences in permittivity. Here e is the dielectric constant of water and $E_{\beta 2}$ represents the field condition in the electrolyte across the DNA membrane. Combing Eq. (22) and Eq. 23;

$$\int_{E_o}^{E_{\beta 1}} E\,dE + \int_{E_{\beta 2}}^{0} E\,dE = \tag{24}$$
$$-\frac{1}{\varepsilon_{eff}}\rho_{DNA}(\psi_\beta - \psi) - \frac{1}{\varepsilon_{eff}}\int_{\psi_o}^{\psi_\beta} \rho_{ions}(\psi)\,d\psi - \frac{1}{\varepsilon}\int_{\psi_\beta}^{0} \rho_{ions}(\psi)\,d\psi$$

In order to describe the physical mechanisms of signal generation when DNA adsorbs to the surface of the transistor two approaches are examined. In the first approach using Eq. (24) the screening models inside and outside the membrane are treated differently while permittivities are the same i.e. $\varepsilon_{eff}=\varepsilon$ throughout. The Debye-Huckel (DH) in Eq. (25) and Poisson-Boltzmann (PB) in Eq. (26) formulations are compared both inside and outside the membrane and solve Eq. (24) self consistently in a background DNA volume charge density of $$\sim 5\frac{C}{cm^3},$$

as shown in FIG. 17c. In the second approach is examined the critical role of varying $\varepsilon_{\mathit{eff}}$ within the PB framework inside the membrane given the same DNA volume charge density.

$$E\frac{dE}{d\psi} = -\frac{2en_O}{kT\varepsilon_{\mathit{eff}}}\left(\frac{e\psi}{kT}\right); \text{Debye-Huckel}(DH) \quad (25)$$

$$E\frac{dE}{d\psi} = -\frac{2en_O}{kT\varepsilon_{\mathit{eff}}}\sinh\left(\frac{e\psi}{kT}\right); \text{Poisson Boltzmann}(PB) \quad (26)$$

First considered is the effect of different ion screening profiles in the DNA layer. It is found that when the DH approximation is used within the membrane $\Delta\psi_O$ varies a lot more in comparison to the PB model (see FIG. 17c). This essentially stems from the strong nonlinear screening property imposed by the PB approximation. In principle, one could reason the use of either approximation by understanding the respective constraints. The PB model treats ions as a continuous quantity and overestimates the screening charge. If close packing of DNA does occur, which is common at μM concentrations, the volume occupied by DNA is roughly estimated to be two-thirds of the total available volume within the layer. The presence of a large ion density within the membrane is thus energetically unfavorable. This necessarily implies a low ion screening within the DNA membrane which can be mathematically treated via the DH approximation. This line of thinking is similar to inference to findings by others in which it was found the best agreement to experimental hybridization data to occur when counterions were completely excluded from the DNA membrane. It is noted that when DNA molecules are loosely packed and the Donnan potential fully forms, the use of the DH approximation is incorrect and the PB approximation should be employed instead. Using a DH approximation outside the membrane is theoretically incorrect but is shown here only for intuitive purposes. Further, a linearized PB approach was recently proposed to tackle such screening effects similar to the DH approximation. The combination of DH inside the membrane (weak ionic screening) and PB outside (strong screening) matches closest to experiment. The use of positive electric fields can only amplify this effect. Field induced counter ion descreening causes more of the DNA charge to be "exposed" to form a depletion zone (i.e. a region devoid of movable ions with a background DNA charge). The depletion region would increase the built-in voltage, which in this case is the "Donnan potential". This hypothesis strongly supports previous experiments where unexpectedly large $\psi_O$ shifts have been observed. Treating the charge inside the membrane using the DH model provides an intuitive understanding of how $\psi_O$ varies when the membrane is poorly screened, but this is a brute force method to account for $\psi_O$ variations and raises the question as to what physical mechanism causes a lower screening.

Other groups treated the ionic screening inside the DNA membrane using a partition energy ($\Delta G_m$) formulation with the PB approximation. In FIG. 17d the potential profile is plotted for different $\varepsilon_{\mathit{eff}}$ values. An energy cost is incurred when ions diffuse from the electrolyte with a higher permittivity into the DNA membrane with a lower permittivity. This partition effect primarily stems from the Born charge-dielectric interaction. For the overall energy to be a minimum, a low counter ion charge within the DNA membrane is required. The low ionic charge density directly translates to a lower screening within the DNA membrane. The self energy of the ion transferred from a medium of low dielectric constant to one of high dielectric constant is treated via the following relation;

$$\Delta G_m = -\frac{69\,z^2}{a}\left(\frac{1}{\varepsilon_{\mathit{eff}}} - \frac{1}{\varepsilon_{medium}}\right) * 0.01036\text{ eV} \quad (27)$$

where a is the ion radius and z is the valency. For a=1.1 Å, z=1, $\varepsilon_{medium}$=80 and $\varepsilon_{\mathit{eff}}$=20, on finds $\Delta G_m$=−0.243 eV.

Ion hydration and polarization effects at the SG interface have not been considered here, but such effects can further riddle the measured $\psi_O$. A large negative $\Delta G_m$ implies a lower ion charge density within the DNA membrane as it is energetically favorable and hence less screening. Such effects have been considered to be orientation dependent and are stronger with the strands parallel to the SG interface and/or tightly packed. This leads to a qualitatively similar result to the DH model but is mathematically more robust. From the measurements presented in FIGS. 15 and 16 for CG driven sensing, a $\varepsilon_{\mathit{eff}}$~40 was extracted when ssDNA immobilizes ($\Delta\psi_O$~150 mV) and an additional decrement to $\varepsilon_{\mathit{eff}}$~30 when hybridization occurs ($\Delta\psi_O$~70 mV) (see FIG. 17e), assuming the strands lie parallel to the surface (see insert, FIGS. 17d and 17e). This is a reasonable approximation as the lysine-DNA interaction is purely electrostatic in nature. It is clear from both approaches that the net screening within the membrane severely affects the measured $\psi_O$. If one does not consider the drop in $\varepsilon_{\mathit{eff}}$, the difference in the hybridization signal drops down to −20 mV as shown in FIG. 17e. Since a significant fraction of experimental observations in relation to DNA hybridization indicate $\Delta\psi_O$ values in the 40-120 mV range and as such can only be justified by either weak screening or ion exclusion from the membrane, it is believed that the major factor determining ion exclusion is the partition effect and the Born charge-dielectric interaction is an important source of $\Delta G_m$.

Nevertheless, a clear relation between $\Delta G_m$ and the E-field is still lacking and is currently work in progress.

iii. On Dual Gate Operation $\psi_O$ Amplification

CG driven $\psi_O$ shifts of ~120-300 mV were observed upon ssDNA addition and a further ~100 mV shift upon hybridization. Conventional GCS theory cannot account for such large $\psi_O$ shifts due to strong nonlinear screening. From measurements presented earlier is extracted an average charge density of $$\sim 0.04\frac{C}{m^2}$$

(immobilized ssDNA) and a subsequent $$\sim 0.02\frac{C}{m^2}$$

during hybridization. With traditional ISFET's however, DNA adsorption and hybridization normally reveal $\psi_O$ shifts of ~40 mV and ~5-20 mV, respectively. The plausible reasons for such differences are as follows:

(i) $\psi_O$, although influenced by the Donnan potential, also depends on the surface pH response, since a pure Nernstian response would effectively screen any membrane charge from the FG. The pH response of the CvMOS is extremely non-Nernstian with and without a PLL coating and $pH_{PZC}$ was found to be closer to pH 9 (not shown). The PLL coating in addition neutralizes most of the surface charge and also makes it slightly positive resulting in a non-monotonic and weak pH response especially around $pH_{PZC}$ (low $N_S$ in Part I). This can enhance the Donnan effect, and thereby lead to larger surface potential.

(ii) The Born charge dielectric function can play a significant role in amplifying the $\psi_O$ shift.

(iii) The high surface charge of $$0.8 \frac{C}{m^2}$$

normally used for $SiO_{2[3]}$ is orders of magnitude higher than the surface charge density observed in this study $$8 \frac{mC}{m^2}$$

for polysilicon with and without PLL. Such high sheet charge densities can lead to high negative $\psi_O$ potentials, screen out most of the DNA charge and often interfere with DNA immobilization affecting the Donnan equilibrium and orientation.

(iv) Majority of ISFET sensors use a constant readout current when monitoring DNA binding and hybridization. This implies a constant field across the gate oxide between the 2D electron/hole gas in the channel and the reference electrode. In the CvMOS due to the different $E_{SG\_OX}$ conditions when driven from the CG, $\psi_O$ can vary by a few $$\left(\sim \frac{KT}{e}\right).$$

This can influence DNA immobilization due to Coulombic interactions, resulting in counter ion descreening and re-orientation on the surface. Interfacial polarization can cause further modulation.

Using the circuit representation shown in FIG. 17a, one may additionally show that the change in $\psi_O$ differ in the three measurement conditions;

$$\Delta \psi_O = \frac{\Delta Q}{C_{SG} + C_{diff}} \quad (28)$$

when $V_{REF}$ is grounded and the CG is driven. On the other hand;

$$\Delta \psi_o = \frac{\Delta Q}{C_{diff}} \quad (29)$$

when $V_{REF}$ is driven and the CG is grounded. In the case when $V_{REF}$ is floating, the change in $\psi_O$ can be written as;

$$\Delta \psi_o = \frac{\Delta Q}{C_{SG}} \quad (30)$$

One readily notices that the readout mechanism can severely affect the measure $\psi_O$. For example, CG and $V_{REF}$ readouts are dominated by the diffusive capacitance. The equations seemingly imply that $V_{REF}$ readout would always result in a slightly higher $\Delta \psi_O$. However, $Q_{DNA}+Q_{ions}$ which makes up $\Delta Q$, can be different under different $E_{SG\_OX}$, which can arise when $V_{th}$ is measured from the reference electrode as opposed to CG. Hence, by appropriate sizing of the CG and SG areas, the sensitivity to DNA detection can be maximized by engineering the $\Delta Q$ dependence on E-field. Additionally when $V_{REF}$ is floating, $\Delta \psi_O$ can swing (~150 mV) a lot more (see FIG. 17b) in comparison to when $V_{REF}$ is pinned (~70 mV) (see FIG. 15) primarily because the screening capacitance of the ionic diffuse layer is much lower. This suggests that the operation of the reference electrode needs more careful evaluation in order to achieve maximum sensitivity. Since the $pH_{PZC}$ lies in between pH=7 and pH=9, when the FG is charge neutral and given evaporation was negligible during the course of experimentation, it is strongly believed that the enhancement in $\Delta \psi_O$ represented in FIGS. 15 and 16 stems from the shift in $Q_{ions}$ within the DNA membrane due to differences in $E_{SG\_OX}$.

iv. Impedance Spectroscopy

In order to further validate DNA desorption upon charge injection, impedance spectroscopy was performed, which probes the dielectric properties of the interface and is not dependent on surface potential and pH fluctuations. This test would help ascertain whether DNA truly desorbs as monitored by the interfacial impedance change. By using the split-gate approach (see methods), the small-signal output is monitored through a lock-in amplifier. An important point is that the bandwidth is determined by the combined effect of the floating gate based transistor gate stack and the parasitic FG to bulk capacitance, leading to a roll-off at approximately 300 KHz, well within the lock-in amplifier and TIA bandwidth. Recently the overall time constant of the Bode response was reported and also shown to be dependent on the contact-lane capacitance (~10 nF) and electrolyte resistance, which results in the first pole at fairly low (~KHz) frequencies. In the present study however the bandwidth of the overall response was limited by the external amplifier. The contact-lane capacitance consists of the source-drain contact line parasitics in parallel to the gate oxide capacitance. SPICE simulations with estimated parameters depict this behavior qualitatively. An increase in the interface capacitance would move $Z_1$ lower and increase the impedance. An increase in interfacial resistance would move $P_1$ lower with a higher time constant. Impedimetric responses were monitored for 2 different DNA lengths (24 and 48 bP). The Bode response with only buffer was recorded and used as a baseline. Strand D1 immobilization revealed a net increase in the interfacial resistance (parallel shift in $P_1$). Upon complimentary (D2) strand addition, $P_1$ was seen to move further in with the clear formation of $Z_1$, indicating relaxation of the adsorbed DNA film illustrated in FIG. 17a. The reason it is termed relaxation is because the roll off in frequency does not follow the 20 dB/decade drop as would be expected of a constant capacitance. This indicates that relaxation is frequency dependent. The DC operating point was adjusted to maintain a constant output current via CG feedback. The bandwidth of the TIA set a limit on the high frequency response which explains the rapid roll off close to 1 MHz. Shorter 24 bP DNA strands (C1) upon hybridization on the contrary showed an outward movement of $P_1$ (see FIG. 17b), possibly indicating a decreased resistance with a very weak formation of $Z_1$, which is consistent with recent evidence. A plausible explanation is that the counter-ion cloud around the DNA molecule has not yet undergone complete relaxation and can still respond to the applied frequency. This affects the resistance and capacitance of DNA as the counter-ion cloud effectively shields the signal. An interesting point is that the appreciable shift in $Z_1$ for the larger D1 and D2 strands occurs only when the oligonucleotides undergo hybridization. This seems to imply that the frequency-dependent nature of the relaxation is affected by the physical structure of the molecule since dsDNA is much more rigid than ssDNA and leads to a different relaxation mechanism.

Upon programming (electron injection) the FG, a recovery was observed of $P_1$ and $Z_1$ to their respective initial points of pure buffer. This is in agreement with the quasi-static analysis where a recovery of $\psi_O$ was observed. Impedimetric spectroscopy using FET's at a constant operating point is immune to any drift in solution pH and reliably probes the dielectric properties and local molecular structure. The impedance technique could potentially be used to ascertain local interactions between DNA and proteins where charge and capacitance can be concomitantly detected, and serve as a versatile test bench in biophysical applications.

2. DNA Detection for Diagnostics a. Introduction

Diagnostics plays a central role in modern day medicinal practice as it enables informed treatment decisions, and helps monitor disease state and promises effective viral and bacterial screening procedures, among many, many other uses. Data that is collected also helps ensure emergency public health interventions and long-term public health strategies. In developing countries access to hospitals and advanced diagnostic centers are mainly relegated to big cities. Providing suitable treatment procedures, laboratories, timely diagnosis and skilled personnel in interior villages, towns and smaller cities is thus difficult. Furthermore the lack of basic infrastructure such as water, storage, transport, electricity and communication makes diagnostics and treatment a hard task in resource limited settings. Under such conditions the utility and importance of point of care (POC) diagnosis becomes critical. Point-of-care (POC) detection, i.e. testing carried at or near the site of the patient, is thus an extremely attractive option offering increased access to tests for infectious diseases such as HIV, malaria, tuberculosis, and sexually transmitted infections.

Recently there have been a number of reports outlining the use of NATs (Nucleic Acid Tests) for the diagnosis and therapeutic monitoring of infections. Such methods are sensitive and allow identification of specific fragments of infectious agent genome. In comparison to immunological (antibody based) biomarkers, NAT's exhibit several important practical advantages, including: (1) straightforward design of specific recognition elements (primers and probes) with predictable molecular behaviors including binding affinities, and (2) compatibility with enzymatic target amplification methods. Amplification techniques such as the polymerase chain reaction (PCR), as well as isothermal amplification methods such as ligase-chain reaction (LCR), nucleic acid sequence-based amplification (NASBA) and transcription-mediated amplification (TMA) are widely used for genomic screening of viruses such as hepatitis C (HCV) and HIV. Most of these amplification procedures use enzymes, for example polymerases, which are effective for target amplification of nucleic acids but introduce important challenges for POC detection. Specifically, enzymes often require refrigeration for transport, storage, and handling. PCR, probably the most widely used method, demands careful temperature control rendering micro and nanoscale integration challenging. Approaches that avoid enzymes and thermal control however are slowly gaining precedence. Although still in the early stages of development, enzyme free approaches represent one important step towards the development of novel POC diagnostics.

Over the last few years POC readout has been widely researched and actively sought through optical, mechanical and electrical means. One method of electrochemical readout that is particularly attractive for diagnostics is the use of field effect transistors (FET's) that transduce biochemical and ionic changes to current through surface charge based sensing. However, direct molecular charge transduction is known to be affected by Debye screening effects close to the sensing interface. Strong nonlinear screening of surface charge due to mobile counterions in the electrolyte causes a rapid decay in surface potential emanating from the sensing interface into the bulk electrolyte. The transistor is sensitive to molecular charges only within this effective length. As the screening effect becomes stronger under moderate to high saline conditions the Debye length reduces and the net sensitivity to molecular charge lowers. It is important to note that DNA hybridization and recognition is most effective under high saline conditions where inter-strand repulsion is lowest, but this scenario would entail strong Debye screening and hence lower the charge sensitivity. Nonetheless we do point out that such charge based sensing schemes have been realized and shown to be massively scalable and highly sensitive when combined with PCR and isothermal amplification strategies. Sensing in such cases is rendered possible through the intrinsic surface proton sensitivity, amplified molecular density and nanowire surface to volume effects to improve the response rendering it suitable for POC. There however has been no report to the best of our knowledge on coupling enzyme and temperature free DNA amplification strategies with transistor readout. Impedimetric detection can potentially overcome the screening capacitance limited response of potentiometric sensors by probing signals at higher frequencies beyond the Debye layer relaxation limit. Most of these studies however use standalone metal electrodes with off-chip amplification. Over the last few years however there have been reports that essentially combine transistors with frequency mode operation pushing the limits of FET based biosensing beyond the screening limited regime. Under moderate saline conditions, this would allow for simultaneous charge and impedance sensing. At this point, two questions are asked: (1) is it possible to detect low concentrations of pathogenic DNA using a non-enzymatic and non-PCR based approach using transistor frequency mode readout; and (2) what are the essential molecular features that one captures with such frequency mode operations.

In this section, therefore, is introduced the use of branched Y-DNA monomers as molecular labels which upon hybridization with pathogenic targets self-assemble into aggregates. This aggregation effect is readout using frequency mode operation of the floating gate based sensor apparatus in accordance with the embodiments. The frequency response (Bode plot) of the transistor characterized by poles and zeros are sensitive to the net change in interfacial AC resistance and capacitance, a consequence of increased fragment size. Also examined is the effect of adding Au nanoparticle labels sensitized with capture probes in addition to Y-DNA monomers as an additional amplifying strategy.

According to an embodiment of the floating gate based sensor apparatus approach for diagnostics, branched Y-DNA monomers are tagged with specific short ss-DNA capture sequences at each end of the Y-core, exhibiting only a partial match to the target. Upon ss-target (pathogen) addition, end probes on each branch of the Y-DNA monomer hybridize with the corresponding set of sequences on the target strand. This reaction is extremely efficient due to the kinetics of solution phase hybridization. Two Y-DNA monomers are thus linked to each other through a single target sequence. This causes a linkage between different monomer-target formations which results in aggregates with distinct molecular weight and size. This is in stark contrast to mismatched Y-DNA fragments, which remain disassociated in the solution. Unlike existing assays that use branched DNA, this method is immobilization and enzyme free.

In one series of experiments demonstrating the effectiveness of the approach, a prototypical pathogen target is chosen, namely a nucleic acid sequence from a conserved region of the HIV genome. Y-DNA nanostructures tagged with capture sequences were treated with both complimentary and non-complimentary target sequences in 500 mM saline conditions in order to ensure maximum hybridization efficiency. In order to ascertain this molecular specific reaction electrochemically, the aggregates were dispensed onto floating gate ion-sensitive transistors and biosensing was performed by probing the TF. The pole (p1) was found to be extremely sensitive to the resistive component of the AC impedance of the molecule-transistor interface while the zero (z1) was determined by the DNA aggregate relaxations, reflective of capacitive effects. At low target concentrations (~100 fM) the Y-DNA-target interaction resulted in an increase in the interfacial resistance reflected by a clear shift in p1, dominated by the un-reacted monomer surface density. Increasing the target concentration lowered p1 but increased z1. This indicates that as aggregation occurs the resistive component at the interface reduces while capacitive effects begin (ex. counter ion polarization) to dominate. This effect is reasoned on the hypothesis of increased polarization due to amplified molecular weight. Relaxations in the KHz range were observed. Addition of capture sequence tagged Au nano-particles was found to further increase the sensitivity due to increased polarization and aggregate size, improving the limit of target detection to ~100 fM.

b. Materials and Methods i. Transistors and Operating Principles

Floating gate based transistors in accordance with the embodiments were fabricated in a 1.5 µm AMI foundry process as described above. According to an embodiment, the transistors were comprised of independently tunable control (CG) and sensing (SG) gates coupled to a common floating gate (FG). The tunnel oxide i.e. the oxide between the channel and the FG is 10 nm thick, while the control oxide which represents the oxide between the CG/SG and FG is 35 nm thick. The CG areas measured 25 µm×40 µm while SG areas varied between 5 µm×400 µm and 200 µm×400 µm. The FG is sandwiched between the control and tunnel oxides and is thus electrically floating. The reference electrode (Ag/AgCl, Warner instruments) pins the electrolyte bulk to a defined electrochemical potential ($V_{REF}$) and also supplies a global small signal AC perturbation. The CG is used to ascertain the threshold voltage ($V_{TH}$) set the quiescent point and provide additional voltage offsets if required. This reduces the burden on the reference electrode to solely provide a DC bias which is important when working with large arrays. It is noted that in the present series of experiments the reference electrode was used to control the DC operating point particularly when dealing with large SG/CG ratios, since the application of high CG biases (~10-18V to achieve saturation) can induce tunneling or shift the field in the SG oxide thereby modulating ionic charge, surface pH and DNA binding as previously shown which can complicate the interpretation of the measurement.

The transistor transfer characteristics (i.e. the drain current $I_D$ as a function of the CG bias ($V_{CG}$) or ($V_{REF}$)), was recorded using a Keithley 236 source measure unit (SMU) (Keithley Instruments, USA) for the drain ($V_D$=1V) and a Keithley 2400 (Keithley Instruments, USA) was used to sweep $V_{CG}$. In order to ascertain the impedance response $V_{CG}$ or $V_{REF}$ was first tuned to a desired DC value such that the drain current level was maintained in saturation at a predefined value usually set between 10 to 50 µA. The drain current output was then fed to a transimpedance amplifier (TIA, SR570 Stanford research systems, USA) with a suitable gain setting such that the output of the amplifier is not saturated. No filter settings were used. The bias on the TIA was set to 1V. The output of the TIA was subsequently fed to two different lock in amplifiers (LIA, SR830 and SR844 Stanford research systems, USA) depending on the frequency range being monitored and the bode response was subsequently recorded and stored. The following equation outlines the TIA output;

$$v_{out} = i_D R_D \quad (31)$$

where $R_D$ is the feedback resistance and $v_{out}$ is the small signal output of the TIA. In the saturation region of the transistor, the small signal current $i_D$ can be recast in the form $g_m v_{gs}$ where, $v_{gs}$ is the small signal gate-to-source voltage and $g_m$ is the small signal transconductance. The gate voltage can be represented in terms of the transfer function across the DNA layer given by the relation, $v_{gs}$=H(j$\omega$)×$v_{in}$, where $v_{in}$ is the AC small signal amplitude. The transfer function representing the relaxation across the DNA-transistor interface is represented by the following equation;

$$H(j\omega) = \frac{1 + sR_{DNA}C_{DNA}}{1 + s\left(\frac{R_{sol}C_{OX} + R_{DNA}}{(C_{OX} + C_{DNA})}\right) + s^2 R_{DNA}C_{DNA}R_{sol}C_{OX}} \quad (32)$$

where $$C_{OX} = \frac{(C_{tun} + C_{CG}) \times C_{SG}}{(C_{tun} + C_{CG}) + C_{SG}}$$

is the effective oxide representing the overall limiting capacitive condition. Here $R_{sol}$ defines the solution resistance. s=j$\omega$, $C_{DNA}$ and $R_{DNA}$ represent the resistance and capacitance of the DNA membrane, $C_{tun}$ the FG to channel capacitance, $C_{SG}$ the sensing gate interpoly oxide capacitance, $C_{CG}$ the control gate interpoly oxide capacitance. It is noted that the effect of $C_{line}$ line i.e. the source/drain parasitic contact lane capacitances is not considered in the analytical derivation to gain an intuitive understanding of the dominant poles and zeros. However, as explained below these additional source and drain line capacitances are accounted for in SPICE simulations to elucidate the overall limiting behavior at higher frequencies and in the limit of poor passivation. The analytical transfer function without accounting for $C_{line}$ represents a two poles and one zero defined by the following three equations. With line capacitances included, the system comprises of two zeros and three poles (not shown) and will be presented elsewhere.

$$p1 = \frac{1}{R_{sol}C_{OX} + R_{DNA}(C_{OX} + C_{DNA})} \quad (33)$$

$$p2 = \frac{1}{R_{sol}C_{DNA}} + \frac{1}{R_{sol}C_{OX}} + \frac{1}{R_{DNA}C_{DNA}} \quad (34)$$

$$z1 = \frac{1}{R_{DNA}C_{DNA}} \quad (35)$$

The CG or reference electrode is re-biased in order to maintain the quiescent point and hence the current level a constant (i.e. constant $V_{FG}$). The $V_{FG}$ is given by the below equation where $C_{GS}$ and $C_{GD}$ represent the gate to source/drain parasitics, $V_S$ and $V_D$ the source and drain potentials, $\psi_O$ the SG surface potential, $C_T$ the total capacitance in the system and Q the stored charge on the FG.

$$V_{FG} = \frac{C_{CG}V_{CG}}{C_T} + \frac{C_{SG}(\psi_o - V_{REF})}{C_T} + \frac{C_{GS}V_S}{C_T} + \frac{C_{GD}V_D}{C_T} - \frac{Q}{C_T} \quad (36)$$

The AC small signal perturbation however is solely supplied by the reference electrode and superimposed on the DC bias whenever applied.

iii. Reagents

The chip was cleaned with DI water and isopropyl-alcohol (IPA) before each test. A small reservoir made of epoxy was created to isolate the fluid from the bond pads. In between experiments with DNA, each chip was additionally treated with soap and gently swabbed to remove any residual DNA. The chips were subsequently treated with Poly-L-Lysine (SIGMA, USA) in order to ensure attraction of monomer aggregates to the sensing surface. Both target fragments and monomer DNA were maintained in TE buffer (10 mM TRIS pH 8, 500 mM NaCl and 1 mM EDTA) which was also used as the blank solution to ascertain the baseline for every experiment. Y-DNA monomers were prepared as follows, three single-stranded DNA molecules were rationally designed with specific sequences such that each was partially complementary to another. These single-stranded DNA molecules were mixed in an equimolar ratio, resulting in self-annealed, branched, Y-shaped DNA (Y-DNA). Each branch of the Y-DNA (see Table 2) contains a sequence partially specific to the target of interest which in this case represents a conserved region from the HIV genome (50 bp, Table 2). Y-DNA monomers were mixed with target (50 bp, Table 2) to a final concentration of 3.3 nM for each of the 3' Y-DNA and 5' Y-DNA causing rapid aggregation within ~15-20 minutes of treatment. Y-DNA monomer concentrations were maintained at ~6.6 nM while the target concentrations varied in order to test for the limit of detection (LOD). Hybridization was performed in solution phase and then dispensed on the CMOS chip. Au nano-particles (Au-NP) (10 nM for 3'AuNP and 10 nM for the 5'AuNP) 15 nm diameter were synthesized in-house using previously published methods[29] and made up to a final concentration of 20 nM. The samples were treated with capture sequences specific to the HIV target and subsequently added to the monomer mixture. Each nanoparticle had approximately 100 capture probes. Gel electrophoresis (Bio-RAD Laboratories, USA) and dynamic light scattering (DLS) (Zetasizer, Malvern UK) studies were performed to ascertain aggregation for both Y-DNA and AuNP Y-DNA mixtures under different target and salt conditions. For the DLS and gel studies the Y-DNA and AuNP's were diluted to final concentrations of 13.3 nM and 39.5 nM respectively. Target concentrations used in gel electrophoresis measurements were ~1 µM. Experiments with transistors were then performed in a light-tight environment.

TABLE 2

| DNA STRAND | SEQUENCE |
|---|---|
| Y1 HIV 5' | CTCATTGATGGTCTCTTTTTTTTGGATCCGCATGACATTCG CCGTAAG (SEQ ID NO. 7) |
| Y2 HIV 5' | CTCATTGATGGTCTCTTTTTTTCTTACGGCGAATGACCGAA TCAGCCT (SEQ ID NO. 8) |
| Y3 HIV 5' | CTCATTGATGGTCTCTTTTTTTAGGCTGATTCGGTTCATGC GGATCCA (SEQ ID NO. 9) |
| Y1 HIV 3' | TGGATCCGCATGACATTCGCCGTAAGTTTTTCAATCTATCCC ATTCTGC (SEQ ID NO. 10) |
| Y2 HIV 3' | CTTACGGCGAATGACCGAATCAGCCTTTTTCAATCTATCCC ATTCTGC (SEQ ID NO. 11) |
| Y3 HIV 3' | AGGCTGATTCGGTTCATGCGGATCCATTTTTCAATCTATCCC ATTCTGC (SEQ ID NO. 12) |
| HIV target (50 bp) | TGTTAAAAGAGACCATCAATGAGGAAGCTGCAGAATGGGATA GATTGCAT (SEQ ID NO. 13) |
| 5' HIV capture probe for AuNP | TTCCTCATTGATGGTCTCTTTTAACATTTTT/ 3ThioMC3-D/ (SEQ ID NO. 14) |
| 3' HIV capture probe for AuNP | /5ThioMC6-D/TTTTT ATGCAATCTATCCCATTCTGCAGC (SEQ ID NO. 15) | c. Results and Discussion for DNA Diagnostic Embodiments i. Simulating the Frequency Response of the CvMOS The frequency response of the floating gate based sensor apparatus was simulated using the split signal delivery method in SPICE including physical descriptions for the double layer, DNA layer and surface hydroxyl ionization. Since the electrolyte is highly conductive, $R_{sol}$~5 KΩ was set. $C_{CG}$ and $C_{SG}$ are set to 1 pF and 20 pF respectively. From the frequency response it was observed that the zero (z1) is critically dependent on $C_{RNA}$ while the pole (p1) is highly sensitive to $R_{DNA}$ (see FIGS. 20a and b). The effect of bulk resistance was then corroborated by varying the background electrolyte concentration and found a clear inward shift in the pole as resistance increased. This result agrees well with inferences drawn from previous efforts. The source/drain line capacitances due to long metal leads and pad capacitances are also widely believed to play a role in determining the overall bandwidth of the circuit. This effect was simulated and by inspection found that increasing the source/drain parasitics together affect p1 and to z1 (see FIG. 20c) by introducing additional poles and zeros. This effect can have a severe bearing on the overall bandwidth of the transducer. Another pertinent question one might ask is whether scaling $C_{SG}$ affect the frequency response. One might expect that as the SG area is reduced, which becomes relevant when dealing with low concentrations of analyte especially during potentiometric readout, p1 would be affected dramatically. In order to impart control over the channel and ensure low operating voltages the $C_{CG}$ should be larger than the tunnel oxide capacitance, i.e. ensure a high coupling ratio. However, since the $C_{CG}$ shows up in parallel to the SG-tunnel oxide capacitance it has a strong bearing on the overall frequency response (not shown). Hence this presents an interesting design tradeoff between quasi-static and AC operations. It is noted that although these simulations roughly highlight the overall RC behavior of static molecular layer, it does not capture the frequency dependent nature of molecular relaxations. In order to incorporate relaxation mechanisms more involved theories including dipole moments and shape dependent relaxation time constants need to be considered. However due to the non-homogeneous shape and size of the resulting DNA fragment it becomes a tedious task to try theoretically capture this. This aspect is under further investigation.

ii. Y-DNA Aggregation and the Effect of AuNP's

Gel-electrophoresis measurements were first performed on Y-DNA monomer under different conditions. A large smear was observed (see FIG. 20a) in the well when target pathogen strands were added indicating aggregation with a large distribution in fragment size. In the absence of target the loaded sample was observed to clearly run across the gel without any smear indicative of un-hybridized Y-DNA monomers. The same occurred with wrong target or sole target additions. DLS studies showed a clear increase in size with aggregates approaching near ~10 nm in diameter within 20-30 minutes of target addition (see FIG. 20b). When 15 nm diameter AuNP's coated with capture probes were additionally added to the Y-DNA mixture, the aggregate sizes increased dramatically upon target addition approximately approaching ~100 nm to ~500 nm. Gel electrophoresis once again showed a clear difference between target treated and untreated samples (see inset FIG. 20c). Target treated samples stuck in the well while un-hybridized fragments were found to clearly run across the gel. The effect of wrong target addition and background salinity was investigated. It was observed that under mismatched target treatment the AuNP-Y-DNA monomer mixture clearly ran across the gel while a reduction in background salinity lowered the aggregation efficiency with periodic bands beginning to appear. These bands are synonymous with aggregates having different number of AuNP's. DLS measurements were performed on mixtures containing AuNP's and Y-DNA monomers in the presence of pathogen. A clear increase in aggregate size was found upon target addition within minutes, with a near 10 fold increase in size when compared to just Y-DNA (see FIG. 20b).

iii. Floating Gate Based Frequency Response to Y-DNA Aggregate Addition

Samples were first exposed to target pathogen and allowed to react in a pellet. The mixture was then subsequently added to PLL functionalized CMOS chips. As shown in FIG. 21a, when pure buffer was introduced, p2, which now was the dominant pole in the system, occurred at approximately 20 KHz. When Y-DNA samples treated with pathogen were introduced we immediately observed a relaxation (indicated by green bi-directional arrow) with p1, z1 occurring in the 10-100 Hz range reflective of molecular relaxation. In comparison when Y-DNA monomer samples without target were added we notice no relaxation while the wrong target addition showed an extremely weak relaxation. Non-specific binding due to partial match of some of the base pairs with the capture probes could possibly have led to a slight increase in aggregate size causing the minor relaxation to be observed. In both cases however an increase in interfacial resistance was still observed. This resistive effect is further studied in FIG. 21b. As the background target concentration was increased the DNA resistive effect decreased synonymous with increased aggregation which caused a lower sheet charge density of free Y-DNA. This resulted in an enhancement in signal (gain) at higher frequencies which can be directly interpreted in terms of increased aggregation effects. One major advantage of frequency domain detection to detect such effects is that under the same saline conditions (500 mM) the potentiometric (quasi-static) response shows an extremely erratic and opposite trend in $\psi_O$ to what is normally expected when DNA immobilizes, clearly indicating a screening limited response, as shown in FIG. 21c.

FIG. 22a-d depicts the ex-situ transfer function in which the baseline transfer function (buffer) is subtracted out from the measured impedance to highlight the molecular relaxation effects. The error bars reflect the standard deviation of the mean across three independent experimental runs. The target concentration for this particular experiment was ~1 μM, to ensure maximal aggregate formation. FIGS. 22a and 22b depict the magnitude and phase under different target conditions (i.e. no target, with target and wrong target (InF-A)). A trough was observed in the magnitude occurring at lower frequencies with target present as compared to when target is absent. With target absent the trough appeared to occur at frequencies beyond 100 KHz. The phase indicated that the dominant time constant for relaxation peaks above 100 KHz. We attribute this to the fact that the relaxation is dominated by a large density of un-hybridized target in the electrolyte. The observation of a trough or peak in the magnitude suggests a frequency dependent relaxation with a characteristic time constant. It is important to note that relaxations which occur in this frequency range are mainly attributed to molecular weight and size. DNA possesses a quasi-permanent dipole moment due to the counter ion cloud in solution. The counter ion relaxation can manifest in two ways, namely: (i) the loosely bound diffuse layer of ions which forms a quasi-permanent dipole with the DNA molecule can stop responding to the AC frequency in the form of an end-to-end movement and usually occurs in the 10 Hz-10 KHz range; and (ii) the tightly bound condensed counterions which form a dipole with the phosphate backbone reveal a dispersion usually in the 10 KHz to 1 MHz range. These relaxations manifest as a shift in overall permittivity (real and imaginary) which in turn affects the impedance. In the present set of experiments, this change in permittivity is amplified by aggregation. In other experiments described herein, it this increased molecular weight effect was ascertained by linearly varying the length of the DNA chain and found a clear length dependent time constant of relaxation in the impedance spectra.

FIGS. 22c and 22d depict the effect varying target concentrations from 100 pM to 1 nM on net aggregate and relaxation effects. The magnitude and phase revealed molecular relaxations in the KHz range. As the target concentration increased the net resistive effect decreased and capacitive effects (relaxation) began to appear (indicated by slight oscillation in the average magnitude trace in FIG. 22c. Correspondingly the phase plot also depicted an oscillation (indicated by green arrow in FIG. 22d). These results suggest that maximal aggregate formation occurs when Y-DNA: target ratios are approximately 1:1. Any further increase in target concentration leads to an effective relaxation time constant dominated by the un-hybridized excess DNA. It is noted that the LOD was found to be in between 100 fM and 1 pM as observed in FIG. 22c.

iv. Floating Gate Based Sensor Apparatus Frequency Response to AuNP-Y-DNA Aggregate Addition In order to increase the LOD, the effect of adding capture probe functionalized AuNP tags to the Y-DNA mixture was tested and ascertained its effect on aggregate formation. As shown in FIG. 23a, upon varying the target concentrations one immediately notices an extremely clear relaxation with a distinct trough, even for target concentrations as low as 100 fM. It is reiterated that the monomer concentrations are fixed at ~3 nM although these experiments. As the target concentrations were further increased the attenuation in signal slowly decreased, the trough reduced, small relaxations appeared at lower frequencies. In FIG. 23b is plotted the phase of the impedance spectra and once again found a clear oscillation corresponding with the trough in magnitude (see FIG. 23a) strongly suggesting that the transistor was picking up molecular relaxations. A secondary peak in signal occurred at frequencies beyond 102 KHz. The inset in FIG. 23b depicts the overall transfer function before the baseline was subtracted clearly showing p1 and z1 formation when the aggregates were introduced. Also compared is the relaxation characteristics of standalone AuNP's and the effect of adding mismatched targets, and a clearly discernible difference was found in both magnitude and phase with no peak or trough in the signal observable within the detectable range. The effect of background salinity was also studied and the trough in the relaxation disappeared as salinity reduced indicating less aggregate formation. In line with the explanation presented in the earlier section on Y-DNA aggregation, it is believed that addition of AuNP's amplifies the molecular mass thereby increasing the polarizability of the aggregates by attracting more counterions. This in turn influences the rotational relaxation behavior through a change in the quasi-permanent dipole moment causing a distinct relaxation.

Accordingly, the transistor-based impedimetric detection of pathogenic DNA, amplified by branched monomer self-assembly, and was successfully carried out under high saline conditions, which is required for nucleic acid hybridization but is not compatible with most/many alternative electrochemical approaches. Branched Y-DNA monomers tagged with 3' and 5' capture probes bind to ss-DNA targets, driven by nucleic acid hybridization, eventually culminating in rapid aggregation among different Y-DNA-target species. The reaction proceeded rapidly due to the kinetics of solution phase hybridization to form aggregates within minutes of target addition at room temperature. The aggregates were then dispensed on the sensing gates of CvMOS transistors. A new split signal delivery methodology was outlined using CvMOS transistors where the AC small signal perturbation and DC bias to set the quiescent point were delivered through independent gates. Aggregate relaxation was reflected by a clear shift in the pole-zero response. A roll-off in signal amplitude with a corresponding peak in phase was observed with increasing frequencies, indicative of relaxations. These relaxations were found to be highly dependent on the amplified molecular mass. AuNP tags coated with capture probes were additionally added to ascertain any effects on the LOD. A clear enhancement in LOD was observed (~100 fM) along with distinct relaxation effects. Taken together the results suggest a non-enzymatic and temperature free method of enhancing hybridization signals coupled with rapid frequency mode transistor operation.

3. Exocytosis Detection Using Floating Gate Based Sensor Apparatus a. Introduction According to yet another embodiment is the use of floating gate based sensor apparatus for exocytosis detection, including the non-faradaic electrochemical detection of exocytosis. According to an embodiment is the detection of exocytosis from mast and chromaffin cells using the floating gate based sensor apparatus.

Synaptic interactions and cell to cell communication in the human body are frequently characterized by the release of charged hormones and transmitters which impinge on specific receptor molecules encoded on the target cell. Depending on the excitable nature, cells respond to these chemical inputs by either further releasing granules containing charged molecules or inducing an electrical wave such as an action potential (AP). These granules are often termed as vesicles. The mechanism of vesicle fusion with the cell plasma membrane upon stimulation and subsequent release of the granular contents (i.e. in the form of quanta) into the extracellular environment is termed exocytosis and is characterized by a distinctive temporal response. Exocytosis recordings are also often employed as indicators of drug action on cells. For example, amperometric recordings have shown that the Parkinson's drug L-Dopa increases the quantal size. There is thus a need to develop high throughput, scalable and multi-functional electronic instrumentation in order to characterize the action of various pharmacological inhibitors, toxins and stimulants on vesicle release. Transmitter and granular release can be specifically induced or inhibited depending on the cell type under study. In immune cells such as mast cells, exocytosis can be induced through a receptor effector function where a specific antigen receptor interaction causes a signal cascade within the cell, culminating in the release of mediators and hormones which causes an allergic response. In neurons on the contrary, electrical excitations in the form of action potentials (AP) propagate along the axon and stimulate neurotransmitter release in the region between the axon terminus of the pre-synaptic neuron and the dendritic spine of the post-synaptic neuron called the synapse. The released transmitters impinge on specific receptors on the post-synaptic neuron inducing another electrical excitation and hence forth. With mast cells the released hormones impinge on cells expressing specific receptors (example the histamine receptor on smooth muscle cells) and elicit a downstream response.

According to an embodiment are provided experiments creating a CMOS sensor capable of detecting degranulation from mast cells, where it can function as an electronic cell assay and also mimic the downstream communication in the post-synaptic excitable cell. Thus the transmitter-receptor induced electrical excitation is replaced by an electronic analogue. Such a system not only provides a test bench for fundamental studies on exocytosis but also monitors cell-specific molecular and electrical events with high temporal resolution. This is paramount in understanding cellular kinetics and establishing rapid screening procedures. It also sets a possible launch pad for future artificial synapse systems and ionic-electronic interfacing circuitry.

Current methods of monitoring exocytosis include fluorescent techniques, and carbon-fiber amperometry. The fluorescent technique often requires labels which increases the complexity of the experiment. On the other hand, amperometry is prone to noise due to the low current levels, requires highly sensitive low-noise amplifiers, relies on faradaic chemistry for detection, and is challenging to miniaturize in terms of pixel density, although recent efforts have resulted in significant improvements. Non-faradaic transistor-based measurements on the contrary extend the detection capability to chemically inactive molecules, are extremely sensitive to surface adsorption, record cellular signals with a high degree of temporal sensitivity, present a naturally occurring high impedance node due to the gate oxide, and render sub-cellular spatial resolution with very low input referred noise characteristics. Previous work on transistor-based cellular sensing has primarily focused on recording signals upon stimulation from excitatory cells such cardiac myocytes and nerve cells. Recently others extended this approach to detect antigen-stimulated T-cell activation detection by CMOS-compatible semiconducting nanowire sensors.

The ISFET-cell interface has been widely researched over the past decade. Typically the cell forms a high impedance seal at the ISFET interface and the voltage within the cleft acts as a secondary gate input to the transistor. Changes in ionic activity sets up a transmembrane potential within the cleft which capacitively influences the transistor output, while surface chemical changes such as pH or molecular binding directly influence the net surface charge.

Limitations of this approach include the lack of independent control of the transistor operating point. Controlling the ISFET operating point traditionally relies either on the reference electrode bias or via source barrier modulation, but running a large voltage across the cell from a reference electrode will potentially influence or even destroy the cell by electroporation. This presents a reliability challenge and limits the choice of supporting signal conditioning circuitry. Also with cells directly immobilized on gate oxide, long-term drift associated with ion penetration into the active region is a serious issue which can potentially lead to deleterious effects during measurement. Recent strides in CMOS technology nonetheless allows the use of metal layers and vias to isolate the transistor channel from the sensing region which has shown promising results. One drawback, however, is that, top metal interfaces lack chemical specificity to ionic and molecular adsorption, unless specific functionalized coatings are used.

Another class of sensors uses nanowire/nanotube channels, as opposed to the ISFET's buried channel, to improve sensitivity due to stronger electrostatic coupling. The transistor operating point however is still modulated by either the reference electrode or a global back gate which sets a limitation on sensitivity tuning for each individual transistor. This scheme further imposes restrictions on control circuitry integration. While there have been recent efforts towards creating independent local gate control to achieve tunability during operation, a highly sensitive, stable, scalable and addressable transducing scheme is still elusive. In this series of experiments is demonstrated CMOS compatible, extended floating gate transistor which serves as an electronic analogue of the downstream communication, i.e., the receptor induced signal cascade. The device permits independent bias control, decouples the sensing region from the active region to allow for independent scaling, and introduces simultaneous charge and impedance readout to record cellular activity.

Accordingly, in one aspect is investigation of exocytosis utilizing one or more of the CvMOS systems described and/or envisioned herein. To demonstrate the efficacy of the CvMOS transistor as a non-invasive synaptic input, exocytosis upon stimulation from non-excitatory RBL mast cells and excitatory chromaffin cells of the bovine adrenal medulla was monitored.

The rat basophilic leukemia cell (RBL-2H3) is a tumor cell line used frequently as an experimental model for mucosal mast cells. The release of inflammatory mediators from mast cells is the primary event in an allergic response. They serve as a robust model for understanding the underlying biophysical and biochemical mechanism which couples signals originating at the membrane receptor with a biological effector function. Immunoglobulins of the IgE class serve as antigenic receptors which are anchored to cells via the membrane protein complex FcεRI. Upon stimulation with DNP BSA (2,4 Dinitrophenyl Bovine Serum Albumin), the receptor crosslink causes a signal cascade within the cell, which eventually culminates in the secretion of preformed mediators stored in the cellular granules. Mast cells form a specialized niche of the immune system, because the triggered cellular activity is immediate. Depending on the particular type of mast cells or basophil's, secretion occurs within seconds to minutes following the IgE cross linking step. Mast cells also provide a meaningful model for cell activation by an immunological stimulus, i.e., by an antibody-antigen reaction.

To complement the non-excitatory cell study, the device detection capability is further demonstrated against the stimulatory responses from excitatory cells such as the chromaffin cell to study neurotransmitter release and related synaptic activity. The chromaffin cell allows the study of stimulus secretion coupling as mediated by both calcium entry and voltage gated channels, i.e., exocytosis induced by depolarization. Transistor recording of vesicle release from chromaffin cells was demonstrated recently using open-gate ISFET's. The recorded signal was attributed solely to the change in the local pH across the double-layer interface which leads to protonation of the surface and hence a change in surface potential. In this work in addition to pH dependent signal generation mechanisms is provides evidence and suggest direct molecular binding to the sensor surface as a signal generating mechanism.

Also presented are non-faradaic electrochemical recordings of exocytosis using floating-gate MOS transistors on a population of mast and chromaffin cells. The floating gate based sensor apparatus allows the quiescent point to be independently controlled and physically isolates the transistor channel from the electrolyte which is critical for stable long-term recordings. The efficacy of this approach is first demonstrated by measuring the degranulation response on a population of RBL-2H3 mast cells mediated by IgE and its high-affinity cell surface receptor FcεRI using the antigen DNP-BSA. Quasi-static I-V measurements reflected a gradual shift in surface potential ($\psi_O$) upon stimulation which was found to be strongly dependent on extracellular calcium ($[Ca]_o$) and buffer strength, suggesting vesicular release with significant proton content. Unsensitized cells showed no response to antigenic stimulation while high-resolution transient recordings revealed current fluctuations with a rapid rise and slowly varying re-equilibration time scales. Fluorescent imaging of dextran-labeled vesicle release performed separately showed evidence of a similar time course after stimulation, indicating that the transistor was recording a coupled stimulus-secretion effect. Extending the study to bovine chromaffin cells, a gradual shift in surface potential is observed accompanied by rapid current fluctuations in response to KCl stimulation, which implies the presence of both action potentials (AP) and molecular release. The extracellular AP response comprised of both biphasic and inverted capacitive waveforms indicative of varying ion channel distributions across the cell membrane and the cell-transistor junction. The approach presents a facile route to realize non-redox based biosensors in commercial CMOS, capable of detecting chemically active or inactive hormones, neurotransmitters and ion channel currents with minimal invasiveness and localized sensitivity control.

b. Materials and Methods i. Cell Culture and Buffer Conditions

RBL-2H3 cells were maintained in a monolayer culture in Minimum Essential Medium, supplemented with 10% fetal bovine serum (Atlanta Biologicals, Norcross, Ga.), 1 ml/liter mito+serum extender (Collaborative Biomedical Products, Bedford, Mass.), and 10 ~mg/ml gentamicin. Typically, cells were used in 3-5 days after passage. The cells were treated with IgE (2 µg/ml) for 1 hour at 37° C. and then resuspended in tyrodes before dispensing them over native SG surfaces. Experiments were performed at 37° C. using variable buffer (HEPES) with concentration ranging between 5 mM and 40 mM. The cells were stimulated by DNP BSA (Sigma) (1 µg/ml). The temperature was maintained through a carefully calibrated air blower. 1 µg/ml monovalent hapten was used to inhibit the degranulation, serving as a negative control. Bovine adrenal glands were obtained from a local slaughterhouse and prepared as described elsewhere. Prior to cell immobilization the chips were coated with 0.02% poly-l-lysine (Sigma) and used only within the first two days of cell preparation. Cells were subsequently dispensed onto transistors in a background of ringer's solution containing 150 mM NaCl, 10 mM Hepes, 5 mMCaCl$_2$, 5 mM KCl, and 2 mM MgCl$_2$ (pH 7.25) (318 mOsm). Ringer's solution (318 mOsm) with reduced sodium chloride (10%) and n-methyl-glucamine (NMG) (90%) were used to test for the occurrence of AP's. Cells were stimulated by adding high KCl (200 mM) globally to the bath such that final KCl concentration was about 80~100 mM. Experiments on the chromaffin cells were performed at room temperature.

ii. Fluorescent Imaging of Vesicle Release

RBL-2H3 mast cells were loaded with 2 mg/ml FITC-dextran overnight, 200 µM serotonin and sensitized with 1 µg/ml IgE. On the following day, the cells were washed repeatedly with tyrodes-BSA before antigenic stimulation. A confocal microscope (Zeiss, Germany) with an immersion lens (60×, oil lens) was used for imaging. The temperature was maintained at 37° C. throughout the experiment using a combination of an objective heater and heated chamber.

iii. Transistors, Instrumentation and Measurement Setup

The chips were fabricated in a 1.5 µm foundry CMOS (AMS) double-poly process with SG exposed and the rest of the chip covered with a 2 µm polymer insulation. The first polysilicon layer forms the FG while the second polysilicon layer forms the CG and SG. The SG interface is exposed to bio-media while the CG is buried below insulation. The control oxide thickness (i.e. interpoly oxide) is 35 nm, the tunnel oxide (i.e. between the FG and channel) is 10 nm, and the capacitance ratio between SG and CG $$\frac{C_{SG}}{(C_{CG})}$$

ranges between 2 and 25 for various designs. SG areas on the chip ranges between ~400 µm×200 µm to ~400 µm×5 µmm while the CG areas are ~40 µm×25 µm. The devices have an active channel area of Three distinct measurement procedures were performed, quasi-static I/V sweeps for monitoring gradual changes in surface potential ($\psi_O$), high-resolution transient recordings of extracellular secretory activity, and impedimetric detection of the SG interface. For I/V measurements, we used a semiconductor parameter analyzer (HP 4145 B) with the drain voltage ($V_D$) kept constant at 1V across all measurements. The transient measurements at a fixed CG bias was recorded by interfacing the transistor to a trans-impedance amplifier (TIA, Stanford Research Systems SR570, CA, USA) with a sensitivity ranging between $$10\,\frac{\mu A}{V} \sim 100\,\frac{\mu A}{V}$$

depending on the relative current magnitude, drift over time and the resolution of the data acquisition system (NI BNC 2110 and NI USB 6259). During transient analysis the signals were high-pass filtered at 1 Hz unless specified and low-pass filtered at 3 KHz before sampling to reduce the aliasing effects. Further analysis and filtering was done through custom software. Before every measurement, the transconductance $g_m$ observed from both the CG and SG was recorded in order to calibrate the sensitivity and accurately estimate $\psi_O$. For the devices used, $g_m$ observed from the SG was found to range between ~0.01-0.3 mA/V, limited by parasitics and interface characteristics after repeated cleaning and lysine addition. Impedance measurements monitored the small-signal transistor gain as a function of frequency. The AC sinusoid was supplied by a function generator (Stanford Research Systems DS345, CA, USA) through the Ag/AgCl reference electrode (Warner instruments, USA), while the DC bias (quiescent point) was set by the CG independently (Keithley 2400, USA). The transistor output was fed to a lock-in amplifier (LIA, Stanford Research Systems SR844, CA USA) through the TIA, hence monitoring the root-mean-square voltage $V_{RMS}$ as a function of frequency. The sensitivity of the TIA was adjusted so as to avoid saturating the LIA input and was operated under the high bandwidth mode.

c. Floating Gate Based Sensor Apparatus Detection Principles

In a floating gate based sensor apparatus, the FG voltage ($V_{FG}$) is set by the weighted sum of the potentials across all its coupled capacitors (Eq. 37) (see FIG. 24e). The input gates have different overlap areas to the FG, which leads to capacitive amplification of the recorded signal. $C_{gs}$, $C_{gd}$ and $C_T$ are the FG-to-source capacitance, FG-to-drain capacitance and total capacitance on FG, respectively. Here Q represents the static charge stored on the FG. $V_{SG}$ is additionally described as ($\psi_O-V_{REF}$) and reflects the change in surface charge through $\psi_O$.

$$V_{FG} = V_{CG} \times \frac{C_{CG}}{C_T} + V_{SG} \times \frac{C_{SG}}{C_T} + \frac{Q}{C_T} + \frac{C_{gs}}{C_T} \times V_S + \frac{C_{gd}}{C_T} \times V_D \qquad (37)$$

A small change in $\psi_O$ causes the threshold voltage measured from the CG ($V_{TH\_CG}$) to be scaled by the amplification factor $$\frac{C_{SG}}{(C_{CG})}.$$

This parameter can be independently tuned with respect to the channel active area which sets the transconductance and frequency response. The nMOS transistor threshold voltage $V_{TH}$ is usually at ~0.8V as measured from $V_{FG}$, which is normally fixed in foundry. Independent CG control could help alleviate the need to set such large biases on the reference electrode but still maintain the transistor above $V_{TH}$ for high $g_m$. Furthermore, it can be used to overcome sensor mismatch by pixel level re-biasing or tunneling static charge on and off the FG, reducing the need for complex global calibration circuitry.

Prior to every experiment, the reference electrode is used to calibrate the transconductance observed from the SG interface to extract the capacitive ratio. During the quasi-static and transient measurements the immobilized cells act as independent current sources i.e., they either secrete charge or give rise to ionic currents upon stimulation. Protons and molecules released during this secretory process can bind to the surface hydroxyl groups and shift $\psi_O$. Ionic currents however in conjunction with the cell-transistor cleft resistance give rise to a transient voltage in the vicinity of the SG surface ($V_J$). A change in $V_J$ modulates $\psi_O$ which modulates $V_{FG}$ and hence the output current. It is important to note that with non-faradaic detection the secreted charges are not consumed (i.e. they do not undergo a redox reaction) but can rather transiently bind to the SG surface or remain within the cell-transistor cleft until they slowly diffuse out. Impedance spectroscopy monitors a shift in the cell's passive properties via the transfer function (see supporting information). Maintaining constant DC readout current through CG feedback enables pure capacitive detection, as $V_{FG}$ is held constant.

d. Results and Discussion for an Exocytosis Analysis Embodiment i. Quasi-Static Measurements Antigen-mediated cross-linking of FcεRI triggers degranulation in mast cells, which eventually results in vesicle release. Cyclic CG voltage sweeps were performed to ascertain the shift in $\psi_O$ upon antigen addition, as shown in FIG. 25. $V_{TH}$ is defined for a constant current level of (1 μA), as shown in FIG. 25a. The readout current and hence $V_{FG}$ is re-calibrated to this defined level by modulating the CG bias. Any shift in $\psi_O$ is then reflected by the change in CG bias required to achieve this constant current condition. A more negative $\psi_O$ (i.e. surface becomes more negatively charged causing $\Delta V_{TH}$ to increase. The IV sweeps (15 seconds duration) indicate larger $\psi_O$ shifts for sensitized cells stimulated with DNP BSA compared to that of the unsensitized cells, as shown in FIGS. 25b and c. Under quasistatic conditions, the double-layer capacitance is large and $\Delta\psi_O$ drops mostly across the tunnel oxide as the FG-channel capacitance is the smallest, as shown in FIG. 25e. Upon media and cell addition on SG, the subthreshold slope changes immediately in comparison to the bare surface, as shown in FIG. 25b. This is due to the additional capacitance $C_{cell}$ in series with $C_{dl}$ between the SG and the reference electrode. However, static capacitive loading due to cell immobilization, ruffling (see FIG. 25d) or further movement upon stimulation shows no observable effects, reflected in the nearly unchanged subthreshold slope during the time course of secretion, which not only verifies device reliability but also indicates minute change in $C_{cell}$ after immobilization and stimulation. FIG. 25e summarizes $\Delta V_{TH}$ under various experimental conditions. First tested was the effect of the extracellular Hepes concentration by varying it from 5 to 40 mM. It is observed that $\Delta V_{TH}$ decreased (i.e. $\psi_O$ becomes more positive) with time and showed a clear buffer dependence, indicating that a major contributor to variations in $\psi_O$ is the acidic environment of the vesicle. Non-specific binding of preformed mediators and small molecules is believed to also occur as the reported signal cannot be totally accounted for by pH effects alone. This is because a $\psi_O$ shift of approximately 50-60 mV would imply a change of almost one pH unit in terms of surface sensitivity. However since $\psi_O$ becomes more positive with time and is found to be dependent on the buffer concentration, the physical principle underlying signal generation suggests protonation of the interface as one important mechanism contributing to the response.

The absence of $[Ca]_o$ was found to suppress any shift in $\psi_O$ even when cells were sensitized, which strongly suggested that calcium entry was an important precondition to elicit a stimulation response. It is well known that intracellular calcium oscillations are a pre-requisite for exocytosis to occur. Furthermore unsensitized cells showed no response upon stimulation, while B4A6C1 mutant cells which are known to weakly degranulate did not yield any appreciable change in $\psi_O$ either. These observations asserted that the observed FET signals were indeed a consequence of cellular secretion. An important condition imposed during the above study was the temperature of the experimental set up was regulated to be close to 37° C. When we stimulated IgE sensitized cells at room temperature under low buffer conditions, the overall $\Delta\psi_O$ increased slightly with time rather than decrease (see FIG. 25e), indicative of lower amounts of released "positive charge" and weak degranulation. While this result is promising as physiologically relevant temperatures are important for mast-cell exocytosis, the exact reason has not yet been established and requires further investigation. It is hypothesized that slow extracellular calcium uptake in the cell transistor cleft is a possible contributing factor. It is reasoned that depletion of cationic charges decreases $C_{dl}$ in the cell-transistor cleft which leads to reduced screening of SG surface (i.e., "less screened" intrinsic hydroxyl charges on SG) which causes $\psi_O$ to become more negative.

Confocal microscopy studies of FITC-dextran-loaded mast cells stimulated under identical conditions was performed to confirm the kinetic time scales of the transistor recordings. FITC-dextran, once taken up by the cell, is stored in its secretory vesicles. Due to the low pH within these vesicles, the FITC fluorescence is quenched. The fluorescence intensity increases when exocytosis occurs as the pH of the secreted vesicular content re-equilibrates with the surrounding. FIG. 25f shows snapshots of vesicular release with green fluorescence puffs as a function of time. FIG. 25g shows the plot of fluorescent intensity as a function of time. Granular release (green), indicated by rapid fluctuations in energy density, is shown to progressively increase with time with a plateau observed after ~4-6 minutes, which is in line with the degranulation kinetics measured by the transistor.

ii. Transient Responses at High Temporal Resolution

In the previous section, the use of quasi-static surface potential measurements is described to monitor exocytosis and found that $\psi_O$ gradually shifts on the time scales of minutes after stimulation. While such recordings prove useful to ascertain antigen/receptor interactions, one cannot monitor events occurring on the order of milli-seconds. Quantal release events with such temporal scales are common during exocytosis, which can potentially be captured with transient recordings under constant CG bias. The release of neurotransmitters and hormones is accompanied by a low pH cloud and results in rapidly varying electrochemical potentials in the cell-transistor cleft. The proximity of the cell to the sensing surface strengthens the capacitive coupling and increases the cleft resistance, inducing a strong modulation in the drain current during secretion. Due to the ion-sensitive nature of the SG interface, surface protonation contributes significantly to the readout fluctuation as corroborated in previous studies. This notion however does not rule out the hypothesis that other chemically active and inactive molecules can non-specifically bind to the sensing interface and shift $\psi_O$ further. This can be further calibrated, for example. During exocytosis, molecules are released within the cell-transistor cleft and diffuse towards the SG surface causing a shift in $\psi_O$. This is analogous to a voltammetric signal; however the charge is not consumed in this process. Transient recordings of RBL mast cell stimulation show the expected behavior of a sharp rise and decay within minutes of stimulation (stimulation indicated by grey bar) with DNP BSA, as shown in FIG. 26a. It is important to point out that mast cell exocytosis ensues only with sustained intracellular calcium oscillations. These oscillations take a finite time to initiate and could possibly contribute to the initial delay observed between stimulation (grey bar) and the onset of vesicle release. However, once these oscillations set in, exocytosis should ensue with a distinct temporal behavior. In FIG. 26b such a trace of activity is depicted from a different batch of cells approximately 300 seconds after stimulation where rhythmic patterns of surface charging are observed. The rapid re-equilibration in $\psi_O$ (see FIG. 26b) is observed and reasoned as follows. Vesicle release is accompanied by protons, ions and a variety of transmitters. Protons bind to the surface hydroxyl groups and shift $\psi_O$ (Jayant et al. 2013a), establishing a new surface charge ($\psi_O$). A change in $C_{dl}$ however causes a transient change in $\psi_O$ (Eq. 38), which will further shift the surface proton concentration through the Boltzmann relationship (Eq. 39). The surface, which acts like a proton buffer, will then try to maintain the same surface pH ($H_S^+$) and re-equilibrate to the same $\psi_O$.

$$\sigma_O = \psi_O C_{DL} \quad (38)$$

$$H_S^+ = H_B^+ \exp\left(\frac{-e\psi_O}{kT}\right) \quad (39)$$

Absence of $[Ca]_o$ in tyrodes suppressed these current fluctuations (not shown) while the introduction of monovalent hapten, which is known to disaggregate FcεRI clustering, effectively reduced the fluctuation to the baseline. This strongly indicates that the recordings are correlated with IgE cross linking induced signaling. FIG. 26c shows the effect of adding tyrodes to a section of an antigen stimulated response (shown by green arrow). The activity persists without any reduction in amplitude. Monovalent hapten is then added indicated by the green arrow in FIG. 26d, and it is immediately found that the overall signal reduces in noise and amplitude. With uncorrelated noise sources, the total noise density in the system is the sum of individual noise densities. Power spectral density (PSD) analysis, shown in FIG. 26e, performed on 100 second chunks of recordings (green and red bars in FIGS. 26c and d) clearly indicates a reduction in the energy density (also known as Nyquist noise) after hapten addition. Since the increase in noise is decided by the cell-transistor cleft activity, i.e. resistance and diffusion of ions, the noise reduction upon hapten addition directly relates to lower receptor aggregation and ion flow. The I/f noise reduces only slightly and appears to be dominated by the transistor channel noise due to small reduction in the transconductance values.

iii. Signal Amplitudes and Surface Charging

Taking account of both the quasi-static and the transient responses, an attempt to resolve the physical basis of the detected signals is made. For example $\psi_O$ shifts of ~5 mV correspond to a net overall interface charge of Q=1 pC~10 pC for moderately sized SG (as capacitive ratio ranging 2~12 and interface specific capacitance of ~10 µF/cm³. So this raises the question as to what causes such a large change in surface charge. Firstly, the calculation presented is a conservative estimate for surface charging and does not include surface protonation effects which can also contribute to the signal amplitude and gradual re-equilibration. Also since the secreted histamine is not readily amenable to voltammetric detection due to its redox inactive nature, further suggests molecular binding to the SG surface as a possible signal generation mechanism in addition to pH and mediator release. RBL cells are known to have few vesicles with each vesicle approximately 0.4 µm. If each granule contained ~0.05 pC which is a reasonable estimate given that secretory cells release 0.1 pC of quanta and a total of 100 vesicles were released from immobilized cells atop the transistor surface, the recordings suggests mV signal amplitudes and that the degranulation response is derived from a collection of vesicles rather than single vesicle events. On an average there are ~10-15 cells covering every SG.

iv. Impedance Spectroscopy at the RBL Cell-Transistor Interface

As secretory granules fuse with the plasma membrane during exocytosis, the overall cell area increases in proportion to the extruded vesicular surface area. It is well known that the most biological membranes have a specific capacitance of $$\sim 1 \frac{\mu F}{cm^2}$$

and hence an increase in membrane area directly reflects an increase in overall capacitance. RBL mast cell degranulation is often accompanied by rapid membrane ruffling and morphological changes within minutes of antigenic stimulation, resulting in a slight increase in total membrane capacitance reaching ~0.5 pF. This is in stark contrast to traditional rat mast cells which reveal a near ~30 pF change due to the lower number of granules in the RBL line. This effect along with granule fusion is normally captured by patch clamp capacitance recordings. Time-resolved impedance measurements thus allow for simultaneous measurements of membrane capacitance and conductance, thus providing a powerful tool to detect such secretion coupling events.

In order to further corroborate cell stimulation and exocytosis detection, experiments were performed in an effort to confirm the overall capacitance shift through impedimetric analysis. Impedance detection along with surface potential was performed using a split excitation technique, see FIG. 27a, where the AC signal is applied through the reference electrode and the DC bias through the CG. In order to concomitantly measure charge and net impedance, the TIA output was split two ways with one end fed to the NI DAQ board sampling voltage at 10 KHz while the other end was fed to the LIA. By monitoring the transconductance $g_m$ as a function of frequency, one can measure the fluctuations in capacitance and interfacial resistance as a shift in the pole-zero response, see FIG. 27b, upon mast cell immobilization. Previous efforts with the ISFET used the AC impedimetric change to ascertain the seal resistance in the cell-transistor cleft, while in this paper we employed the approach to capture fluctuations in cell/transistor interfacial impedance away from the quasi-static regime. The impedance readout at this operating point mainly depended on the net capacitance, and much less on charge fluctuations at the interface. The model for the cell-SG interface in frequency domain follows a similar theory to biomolecular modeling under frequency analysis with the first pole dominated by interface resistance and the first zero dominated by the cell passive properties (see supporting information). In FIG. 27b is shown the effect of the antigen stimulation on the Bode response and observe a shift in the zero indicating an increase in the cell capacitance after stimulation. This result is consistent with the overall simulations and models presented earlier. That data is fit in spite of the limited frequency range to gain an estimate for circuit parameters. A capacitance change between ~0.05 pF-0.1 pF is extracted, depending on selection of fitting parameters. This is lower in comparison to the whole-cell patch clamp recordings of mast cell exocytosis where shifts on the order of 0.4 pF have been observed. This is rationalized in that in impedance mode there is access only to the attached membrane in the cell-transistor overlap region which varies less in surface area while the free membrane (portion away from the transistor surface) varies a lot more in surface area during exocytosis. It is noted that in a recent impedance study, although performed on a different cell line, the extracted values of seal resistance and cell capacitance agree well with the values reported here.

In FIG. 27c a concomitant $\psi_O$ and impedance measurement is performed at a fixed frequency (40 KHz). A step increase is found in $\psi_O$ upon antigenic stimulation with a distinct time course indicative of surface charging. The recording is not high pass filtered in this study so as to reflect this DC shift. The AC impedance reflected by the transconductance measurement initially decreases upon stimulation but then subsequently increases (shaded region), suggesting cell secretion and capacitance change due to morphology. About 50-second delay is observed between the surface charging and impedance change, possibly reflecting differences in dynamics between cell secretion and gradual membrane ruffling. Although performed on a population of immobilized cells, this experiment points out a clear indication that transistors can be used to simultaneously measure capacitance (impedance) and charge (surface potential). Future experiments will be aimed at experiments involving single cell studies.

v. The Chromaffin Cell-Transistor Coupling

To further demonstrate exocytosis detection by CvMOS with high-resolution transients, chromaffin cell of the bovine adrenal medulla was chosen as a known exocytotic model albeit through a different mode of stimulation. The chromaffin cell helps serve as a model system of voltage-gated ion-channel activity and exocytosis induced by membrane depolarization. Chromaffin cells are known to secrete catecholamines as a consequence of exocytosis and the granular content is known to be highly acidic which should contribute to a net shift in surface potential upon release. One important difference between the chromaffin and mast cell studies is that the electrical currents in the form of AP can flow in the cell transistor junction as a result of activated ion channel activity in neuro-endocrine cells. In previous transistor-based studies of chromaffin cells, this aspect of signaling (i.e. AP's) was ignored, because it complicates the model to discern independent electrochemical contributions in the cell-transistor cleft.

Chromaffin cells were prepared as described above, resuspended in ringer's solution and then dispensed on the poly-l-lysine coated SG. After about 45~60 minutes after immobilization, a pipette of concentrated KCl was introduced and the solution was flushed to reach the final concentration of KCl around 80 mM. Upon KCl stimulation which causes membrane depolarization, sharp fluctuations in readout current with millisecond time resolution were observed, as shown in FIG. 28a. The recorded signals are found to be strongly dependent on extracellular $[Na]_o$ and $[Ca]_o$, suggesting simultaneous AP and catecholamine release. The presence of AP and exocytosis was independently confirmed through the following control experiments. FIG. 28b depicts the effect of adding ringers solution rich in $[Na]_o$ (marked by grey bar) to cells previously stimulated by high KCl in NMG substituted ringers media. The high-pass filter criterion was relaxed to observe slow drift. Immediately observed is surface charging and rapid fluctuations upon $[Na]_o$ being introduced indicating that fluctuations are a true consequence of AP activity. The asterix marks a momentary break in recording, as shown in FIG. 28b. In a separate experiment, shown in FIG. 28c, high KCl was once again added (shown by green arrow) to immobilized chromaffin cells in NMG rich ringer's media. The asterix marks a momentary break in recording.

A gradual increase in $\psi_O$ as a function of time upon KCl depolarization was noticed although AP's cease to exist. The rise in $\psi_O$ denotes a net positive surface charging effect similar to the mast cell degranulation study, indicating that secretion and possibly exocytosis is being detected. Also observed were fluctuations in $\psi_O$ with time courses typical of delayed diffusion. In the absence of $[Ca]_o$, $\psi_O$ shifts were absent altogether (not shown) while AP waveforms characterized by their milli-second time scales and rapid activity continued to persist, as shown in FIG. 28d. This experiment clearly indicates that the $\psi_O$ shifts measured previously were truly a consequence of exocytosis. IT is noted that the observed amplitude of extracellular AP's were smaller in the absence of $[Ca]_o$ over multiple experimental runs, although we present only one representative result here. This observation could be attributed to the following reasons: a) there exists a feedback between granular secretion and ion channel activity, b) calcium activated potassium currents (IKCa) are significant, and c) there exists a relatively low ion channel conductance in the cell-transistor cleft as opposed to the free membrane in the absence of $[Ca]_o$. Past works have established that IKCa in chromaffin cells comprises of almost 70-90% of the outward potassium current. Also AP stimulus and firing rates are known to play a key role in stimulus secretion coupling. The present study however does not provide sufficient evidence and requires further experimental investigation. The effect of ion channel distribution between the free and fixed parts of the cell membrane is a key effect that decides the amplitude and shape of the AP. As shown in FIG. 29, both biphasic and inverted capacitive responses were observed. Such waveforms are classically interpreted as (a) a capacitive (i.e. biphasic) response across the cell membrane due to the intracellular AP which gives rise to a shift in junction voltage ($V_J$) and (b) the ion-channel conductance in the cell-transistor cleft (inverted capacitive) of either the Na, K or both are raised against the free membrane. Also performed is match filtering and amplitude threshold signal processing on three independent experiments lasting between 200-300 seconds each where chromaffin cells are stimulated by high KCl. Over the time course of the entire experiment, recurring AP waveforms with a clear biphasic and inverted capacitive response are observed, as shown in FIGS. 29e and f. The inverted response has on average slightly lower amplitudes in comparison to the biphasic response. FIG. 29g depicts a cluster of the biphasic and inverted waveforms for ~100 seconds of recorded data after match filtering and threshold operations. A more than sufficient correlation is found between successive hits for both AP types, indicating homogeneity across the filtered waveforms. In order to elucidate the physical basis of the waveforms the point-contact model was used including the Hodgkin-Huxley (HH) description for ion channel activity in the cell-transistor cleft developed previously, the intracellular membrane potential $V_M$ elicited through a current stimulus can be calculated by Eq. (40) (see FIG. 30a) along with the rate equations. Then used is $V_M$ to calculate the cleft potential $V_J$ in Eq. (41);

$$\frac{I_{INJ}}{A_{FM}} = \sum_i (g_{FM} + g_{JM}) \cdot (V_M - V_o) + C_M \cdot \frac{dV_M}{dt} \quad (40)$$

$$V_J \cdot g_J = \sum_i (V_M - V_o) \cdot g_{JM} + C_M \cdot \frac{dV_M}{dt} \quad (41)$$

where $g_{JM}$ represents the conductance in the cell membrane in contact with the transistor SG, $g_{FM}$ represents the conductance in the free membrane not in contact with the transistor and $g_J$ represents the conductance in the cell-transistor cleft due to displaced ions (i.e., the effective seal resistance). Also, i represents the different types of channels (i.e. Na$^+$, K$^+$ and leakage channels). The cell thus acts like a current source creating an extracellular potential due to the net resistance in the cleft.

In the model there was a decision to maintain the specific free membrane conductance for Na$^+$ ($G_{Na1}$) and K$^+$ ($G_{K1}$) as 600 pS/μm$^2$ and 200 pS/μm$^2$, respectively, while varying the overall attached membrane conductance ($G_{Na2}$ and $G_{K2}$) and scaling them by factors ranging from 0 to 2 in steps of 0.2 (i.e. $g_{Na}=G_{Na2}\cdot k$ and $g_K=G_{K2}\cdot k$) with respect to the attached membrane values (see FIGS. 30b-d). When the overall ionic conductance in the cleft was raised with respect to the attached membrane with $G_{Na2}$=600 pS/μm$^2$ and $G_{K2}$=200 pS/μm$^2$, the waveforms resemble inverted transients (k=2) (see FIG. 30b). It was also found that if $G_{K2}$ is lowered to 100 pS/μm$^2$, GNa$_2$ and hence the overall Na$^+$ conductance appears higher than K$^+$ in the cleft, which causes the inverted response to become stronger (see FIG. 30c). This happens because Na$^+$ rushes into the cell during the rising phase of the AP, and ionic charges get depleted in the cleft resulting in a steeper trough in the AP waveform. Decreasing the Na$^+$ conductance in the cleft in comparison to the attached membrane however creates a stronger rise in the extracellular AP and a similarly diminished intra-cellular waveform (see FIG. 30d), which is indicative of K$^+$ channel dominance. Such a waveform was observed in the experiments by visual inspection but was found to be statistically infrequent. With respect to extracellular AP amplitudes, a cleft conductance of approximately ~50 pS/μm$^2$ which is reflective of a moderate seal resistance, results in extracellular peak-peak amplitudes of approximately 2 mV (see FIG. 30b), in accordance with previous transistor studies on neurons. Higher cleft resistances, i.e. a lower conductance, will amplify the extracellular potential even further and hence improve the seal between the cell and transistor, which is paramount to ensure high signal-to-noise ratio. It is noted that a higher specific membrane capacitance of $$\sim 5 \frac{\mu F}{cm^2}$$

was assumed in the simulation to account for the number of cells on the SG surface. A considerable amount of experimental effort has been previously performed on neurons to elucidate the underlying physical basis of such signals based on ion channel re-distribution, enhancement and depletion. FIGS. 29 and 30 suggest that since both biphasic and inverted capacitive responses were recorded by the CvMOS, ion channel distributions across the chromaffin cell membrane during secretion matches closest to the case of up-regulated Na$^+$ and K$^+$ conductances in the cleft with respect to the free membrane. The experimental evidence presented in this series of experiments further validates extends the applicability of the point-contact model to primary neuro-endocrine cells.

4. Proton Sensing and Actuation

According to yet another embodiment is the use of a floating gats based sensor apparatus for detecting and/or actuating protons. Proton detection can be extremely important, for example, from both a physiological (intracellular secreted charge, vesicles, traditional pH meters, blood pH, local extracellular pH) and industrial (acidity tests in packaged foods) perspective. In the last few years, for example, there has been a surge in interest to develop ion-sensitive sensors for sequencing. ISFET's are used to detect single DNA bases using the intrinsic proton sensitivity of the interface.

According to an embodiment, a floating gate based sensor apparatus biosensor with the appropriate surface will have the ability to boost the proton diffusion into the top few layers of the sensing interface due to stored non-volatile charge (electrons), thus enabling a higher signal-to-noise for pH sensing. Additionally it allows one to tune the surface from being pH-sensitive to pH-insensitive, which is useful when switching between proton detection and intrinsic biomolecular charge detection.

Further, this ability to manipulate the surface charge induces a change in local ion concentration at the surface. As a result, these methods and systems would be very useful in microfluidic drug delivery in which different concentrations of ions can be mixed using field effect control, while simultaneously sensing the effect of the drug. Thus, for example, according to this embodiment, the floating gate based apparatus in accordance with the embodiments could be utilized for both drug screening and drug delivery.

5. Biomolecular Sensing and Actuation

According to yet another embodiment is the use of a floating gate based sensor apparatus for detecting, desorbing, and/or re-adsorbing one or more biomolecules. As described above, the floating gate based sensor apparatus was utilized for the sensing and dynamic manipulation of surface-immobilized DNA. In a similar manner, the floating gate based sensor apparatus could be utilized for any of a variety of different biomolecules. For example, according to an embodiment, instead of the poly-l-lysine utilized to immobilize the DNA, another compound or agent could be used to coat a portion of the floating gate based sensor apparatus for immobilization of one or more target biomolecules. A variety of other techniques could also be utilized to immobilize or actuate the one or more target biomolecules.

This would be desirable, for example, where the sensor must be re-usable or the surfaces need to be regenerated, as the floating gate based sensor apparatus could be re-used for the same or different biomolecules. This would also be desirable where background false positives should be or need to be reduced. Another benefit of utilizing the floating gate based sensor apparatus for detecting, desorbing, and/or re-adsorbing one or more biomolecules is that the system could be designed to be specific for a subset of molecules within a mixture of two or more different molecules. Further, the floating gate based sensor apparatus system would improve the signal-to-noise ratio for protein, DNA, and for RNA studies. Indeed, the floating gate based sensor apparatus system could thus be utilized for or with DNA and protein microarrays, and as a component of point-of-care diagnostic devices in part because of the small size of the system, as well as the re-usability of the sensor, among many other factors.

6. Impedance Spectroscopy

According to yet another embodiment is the use of a floating gate based sensor apparatus in accordance with the embodiments for impedance spectroscopy, particularly utilizing the combined AC and DC methods and systems described herein. According to these methods and systems, for example, the floating gate based sensor apparatus system may be utilized for simultaneous charge and structure detection, which would especially useful with proteins and DNA-protein interactions. Another advantage would be cell surface area monitoring concomitantly with the analysis of released protons, ions, and/or molecules, which could be utilized to study disease state such as metastasis or brain disorders, among many others.

According to another embodiment, using a floating gate based sensor apparatus for impedance spectroscopy would allow for the analysis of cell membrane capacitance and simultaneous action potential and vesicle release. The methods and systems could also be utilized for small molecule drug packing and DNA sorting, among other uses. These methods and systems could be extremely important in drug screening, for example.

7. Cellular Interfaces

According to yet another embodiment, and as described above, is the use of a floating gate based sensor apparatus as a mechanical interface with the cell. For example, according to various methods and systems the floating gate based sensor apparatus could be utilized with peripheral nerves to both stimulate and detect action potentials, thus acting as a true interface. The floating gate based sensor apparatus could also be utilized according to the methods and systems described and envisioned herein to detect released neurotransmitters, thus giving rise to an electroceutical with an array of uses. In the brain, for example, the floating gate based sensor apparatus system could be used for extracellular stimulation and recording, including in a massively parallel system for numerous neurons at once. The system could also be utilized to measure non-reducible and oxidizable neurotransmitters in the brain such as GABA, among others. According to yet another embodiment, the system could be utilized to detect one or more neurotransmitters such as acetylcholine, dopamine, and/or D-serine, among others, using a non-faradic approach. This would be benign and involve no passage of current in the brain. According to another embodiment, the system could be used for cochlear implants or a wide variety of other implants in or that somehow interface to the nervous system.

All references, including publications, patent applications, and patents cited herein are hereby incorporated by reference in their entireties to the same extent as if each reference was individually and specifically indicated to be incorporated by reference and were set forth in its entirety herein.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening.

The recitation of ranges of values herein are merely intended to serve as a shorthand method of referring individually to each separate value falling within the range, unless otherwise indicated herein, and each separate value is incorporated into the specification as if it was individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not impose a limitation on the scope of the invention unless otherwise claimed.

No language in the specification should be construed as indicating any non-claimed element as essential to the practice of the invention.

It will be apparent to those skilled in the art that various modifications and variations can be made to the present invention without departing from the spirit and scope of the invention. There is no intention to limit the invention to the specific form or forms disclosed, but on the contrary, the intention is to cover all modifications, alternative constructions, and equivalents falling within the spirit and scope of the invention, as defined in the appended claims. Thus, it is intended that the present invention cover the modifications and variations of this invention provided they come within the scope of the appended claims and their equivalents.

What is claimed is:

1. A multi-gate transistor sensor comprising:
a substrate layer structured to be underneath and in physical contact with a portion of a floating gate layer, wherein a first dielectric layer lies between the substrate layer and another portion of the floating gate layer;
a sensing gate layer structured to be on top of the floating gate layer with a second dielectric layer lying between the floating gate layer and the sensing gate layer;
a control gate structured to be on top of the floating gate layer with the oxide layer between the floating gate layer and the control gate, wherein the floating gate layer is capacitively coupled to the control gate and the sensing gate layer;
a liquid sample chamber structured to be on top of the sensing gate layer; and
a reference electrode in the liquid sample chamber, wherein the reference electrode is in physical contact with the liquid and the sensing gate layer is in physical contact with the liquid.

2. The multi-gate transistor sensor of claim 1, wherein the control gate is adjacent to the sensing gate layer and separated from the liquid sample chamber by a passivation layer.

3. The multi-gate transistor sensor of claim 1, wherein the control gate and the sensing gate layer are capacitively coupled to the floating gate.

4. The multi-gate transistor sensor of claim 1, wherein the first dielectric layer and the second dielectric layer have different thicknesses.

5. The multi-gate transistor sensor of claim 1, wherein the first dielectric layer and the second dielectric layer have different dielectric constants.

6. The multi-gate transistor sensor of claim 1, wherein the sensing gate layer comprises one or more of a dielectric material, a conductor material, a metal conductor material, or a polysilicon conductor material.

7. The multi-gate transistor sensor of claim 1, wherein the substrate comprises a bulk semiconductor substrate.

8. The multi-gate transistor sensor of claim 1, wherein the substrate comprises a semiconductor-on-insulator substrate.

9. The sensor apparatus of claim 1, wherein the control gate electrically biases the sensing gate layer with respect to the substrate.

10. The multi-gate transistor sensor of claim 1, wherein the reference electrode electrically biases a sample within the liquid chamber with respect to the sensing gate layer.

11. The multi-gate transistor sensor of claim 1, wherein the reference electrode electrically biases a sample within the liquid chamber with respect to the sensing gate layer.

12. The multi-gate transistor sensor of claim 1, wherein a coupling capacitance between the reference electrode and a fluid in the liquid sample chamber is larger than a sensing gate capacitance between the sensing gate layer and the fluid.

13. The multi-gate transistor sensor of claim 1, wherein with respect to the substrate, the reference electrode is biased with a direct current potential that is positive or negative, or biased with the direct current bias with a superimposed alternating current bias.

14. The multi-gate transistor sensor of claim 1, wherein the reference electrode is electrically coupled to the substrate.

15. The multi-gate transistor sensor of claim 1, wherein the reference electrode is electrically floating with respect to substrate layer.

16. The multi-gate transistor sensor of claim 14, wherein the control gate is biased with respect to the substrate layer to enable electron tunneling from the substrate layer to the floating gate layer or from the floating gate layer to the control gate.

17. The multi-gate transistor sensor of claim 1, wherein electron tunneling out of the floating gate layer to the control gate leaves a net positive charge on the floating gate layer and a positive electric field with respect to the reference electrode.

18. The multi-gate transistor sensor of claim 1, wherein electron tunneling into the floating gate layer causes a negative electric field with respect to reference electrode.

19. The multi-gate transistor sensor of claim 1, wherein a charge on the floating gate layer attracts or repels a biomolecule on a surface of the sensing gate layer.

20. The multi-gate transistor sensor of claim 1, wherein a charge on the floating gate layer causes a new electric field in the second dielectric with respect to the reference electrode and the substrate layer.

21. The multi-gate transistor sensor of claim 1, wherein a charge on the floating gate layer electrically stimulates one or more cells.

22. The multi-gate transistor sensor of claim 1, wherein the reference electrode is biased with an alternating current signal and the control gate is biased by a direct current signal.

23. A multi-gate transistor sensor comprising:
- a gate layer structured to be underneath and in physical contact with a first dielectric layer;
- a floating gate layer structured to be on top of the first dielectric layer, wherein a second dielectric layer is structured to be on top of the floating gate layer;
- a sensing layer structured to be on top of the second dielectric layer, wherein the floating gate is capacitively coupled to the floating gate layer and the sensing gate;
- a liquid sample chamber structured to be on top of the sensing gate layer; and
- a reference electrode above the sensing layer so that when liquid is in the liquid sample chamber, the reference electrode is in physical contact with the liquid and the sensing layer is in physical contact with the liquid, wherein a charge on the floating gate layer attracts or repels a biomolecule on a surface of the sensing layer.

24. The multi-gate transistor sensor of claim 23, wherein the control gate and the sensing layer are capacitively coupled to the floating gate.

25. The multi-gate transistor sensor of claim 23, wherein the sensing layer comprises one or more of a dielectric material, a conductor material, a metal conductor material, or a polysilicon conductor material.

26. The multi-gate transistor sensor of claim 23, wherein the reference electrode is structured to electrically bias a sample within the liquid chamber with respect to the sensing layer.

27. The multi-gate transistor sensor of claim 23, wherein the reference electrode electrically biases a sample within the liquid chamber with respect to the sensing layer.

* * * * *